US009388436B2

(12) United States Patent
Bauer et al.

(10) Patent No.: US 9,388,436 B2
(45) Date of Patent: Jul. 12, 2016

(54) FATTY ACID DESATURASE AND USES THEREOF

(75) Inventors: Jörg Bauer, Teltow (DE); Xiao Qiu, Saskatoon (CA); Patricia Vrinten, Saskatoon (CA)

(73) Assignee: BASF Plant Science Company GmbH, Ludwigshafen (DE)

( * ) Notice: Subject to any disclaimer, the term of this patent is extended or adjusted under 35 U.S.C. 154(b) by 653 days.

(21) Appl. No.: 13/511,069

(22) PCT Filed: Nov. 23, 2010

(86) PCT No.: PCT/EP2010/067979
§ 371 (c)(1),
(2), (4) Date: May 21, 2012

(87) PCT Pub. No.: WO2011/064181
PCT Pub. Date: Jun. 3, 2011

(65) Prior Publication Data
US 2012/0240248 A1    Sep. 20, 2012

Related U.S. Application Data

(60) Provisional application No. 61/263,838, filed on Nov. 24, 2009.

(30) Foreign Application Priority Data

Nov. 24, 2009    (EP) .................................... 09176869

(51) Int. Cl.
*C12P 7/64*       (2006.01)
*C12N 9/02*       (2006.01)
*C12N 15/82*      (2006.01)

(52) U.S. Cl.
CPC ............. *C12P 7/6427* (2013.01); *C12N 9/0071* (2013.01); *C12N 15/8247* (2013.01); *Y02P 20/52* (2015.11)

(58) Field of Classification Search
None
See application file for complete search history.

(56) References Cited

U.S. PATENT DOCUMENTS

| | | |
|---|---|---|
| 2010/0199365 A1 | 8/2010 | Senger et al. |
| 2010/0263088 A1 | 10/2010 | Bauer et al. |
| 2011/0039010 A1 | 2/2011 | Rein et al. |
| 2011/0088123 A1 | 4/2011 | Bauer et al. |
| 2011/0113510 A1 | 5/2011 | Bauer et al. |
| 2011/0138490 A1 | 6/2011 | Bauer et al. |
| 2011/0162105 A1 | 6/2011 | Bauer et al. |
| 2011/0277043 A1 | 11/2011 | Senger et al. |
| 2012/0124705 A1 | 5/2012 | Bauer et al. |
| 2012/0185965 A1 | 7/2012 | Senger et al. |
| 2012/0233716 A1 | 9/2012 | Bauer et al. |

FOREIGN PATENT DOCUMENTS

| | | |
|---|---|---|
| WO | WO-2005/047480 A2 | 5/2005 |
| WO | WO-2009/016202 A2 | 2/2009 |

OTHER PUBLICATIONS

International Search Report for PCT/EP2010/067969 mailed Feb. 24, 2011.
Okuley, J., et al., "Arabidopsis FAD2 Gene Encodes the Enzyme that is Essential for Polyunsaturated Lipid Synthesis", The Plant Cell, 1994, vol. 6, pp. 147-158.
Tudzynski, P., et al., "Biotechnology and Genetics of Ergot Alkaloids", Appl. Microbiol. Biotechnol., 2001, vol. 57, pp. 593-605.
Qiu, X., et al., "Identification of a Δ4 Fatty Acid Desaturase from *Thraustochytrium* sp. Involved in the Biosynthesis of Docosahexanoic Acid by Heterologous Expression in *Saccharomyces cerevisiae* and *Brassica juncea*", The Journal of Biological Chemistry, 2001, vol. 276, No. 34, pp. 31561-31566.
Arondel, V., et al., "Map-Based Cloning of a Gene Controlling Omega-3 Fatty Acid Desaturation in *Arabidopsis*", Science, 1992, vol. 258, pp. 1353-1355.
Broadwater, J. A., et al,, "Desaturation and Hydroxylation: Residues 148 and 324 of *Arabidopsis* FAD2, in Addition to Substrate Chain Length, Exert a Major Influence in Partitioning of Catalytic Specificity", The Journal of Biological Chemistry, 2002, vol. 277, No. 18, pp. 15613-15620.
Calvo, A. M., et al., "Genetic Connection between Fatty Acid Metabolism and Sporulation in *Aspergillus nidulans*", The Journal of Biological Chemistry, 2001, vol. 276, No. 28, pp. 25766-25774.
Shanklin, J., et al., "Desaturation and Related Modifications of Fatty Acids", Annu. Rev. Plant Physiol. Plant Mol. Biol., 1998, vol. 49, pp. 611-641.
Broun, P., et al., "Catalytic Plasticity of Fatty Acid Modification Enzymes Underlying Chemical Diversity of Plant Lipids", Science, 1998, vol. 282, pp. 1315-1317.
Mey, G., et al., "The Biotrophic, Non-Appressorium-Forming Grass Pathogen *Claviceps purpurea* Needs a Fus3/Pmk1 Homologous Mitogen-Activated Protein Kinase for Colonization of Rye Ovarian Tissue", Molecular Plant-Microbe Interactions, 2002, vol. 15, No. 4, pp. 303-312.
Mantle, P. G., et al., "Differentiation of *Claviceps purpurea* in Axenic Culture", Journal of General Microbiology, 1976, vol. 93, pp. 321-334.
Knutzon, D. S., et al., "Identification of Δ5-Desaturase from *Mortierella alpina* by Heterologous Expression in Bakers' Yeast and Canola", Journal of Biological Chemistry, 1998, vol. 273, No. 45, pp. 29360-29366.
Qi, B., et al., "Production of Very Long Chain Polyunsaturated Omega-3 and Omega-6 Fatty Acids in Plants", Nature Biotechnology, 2004, vol. 22, No. 6, pp. 739-745.
Sakuradani, E., et al., "A Novel Fungal ω3-Desaturase with Wide Substrate Specificity from Arachidonic Acid-Producing *Mortierella alpine* 1S-4", Appl. Microbiol. Biotechnol., 2005, vol. 66, pp. 648-654.
International Preliminary Report on Patentability for PCT/EP2010/067969 issued on May 30, 2012.

*Primary Examiner* — Elizabeth McElwain
(74) *Attorney, Agent, or Firm* — Drinker Biddle & Reath LLP

(57)    ABSTRACT

The present invention relates to nucleic acids derived from *Limonomyces roseipellis*. The invention also relates to the individual coding sequences and to proteins encoded by these sequences as well to a process for converting oleic acid to linoleic acid to linoleic acid and the production of arachidonic acid, eicosapentaenoic acid and/or docosahexaenoic acid in a plant.

20 Claims, 14 Drawing Sheets

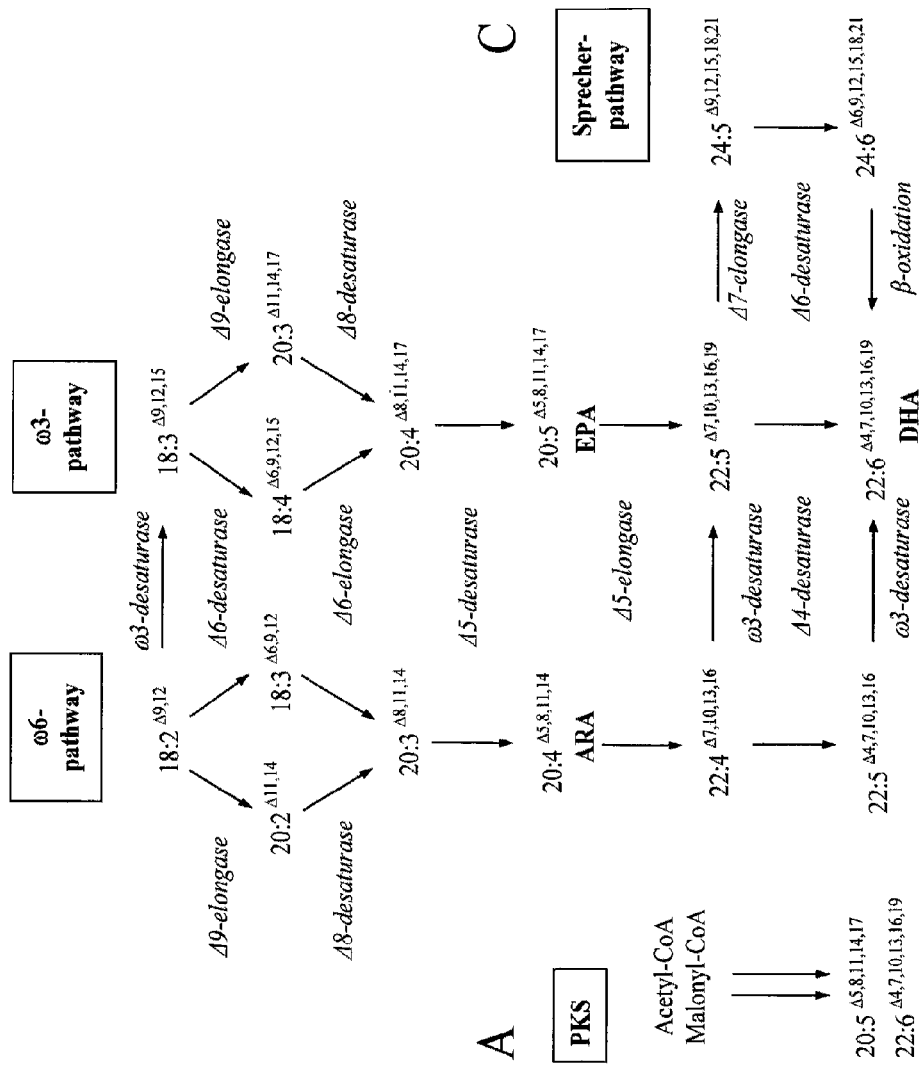
Figure 1: Schematical overview of the different enzymatic activities leading to the production of ARA, EPA and DHA.

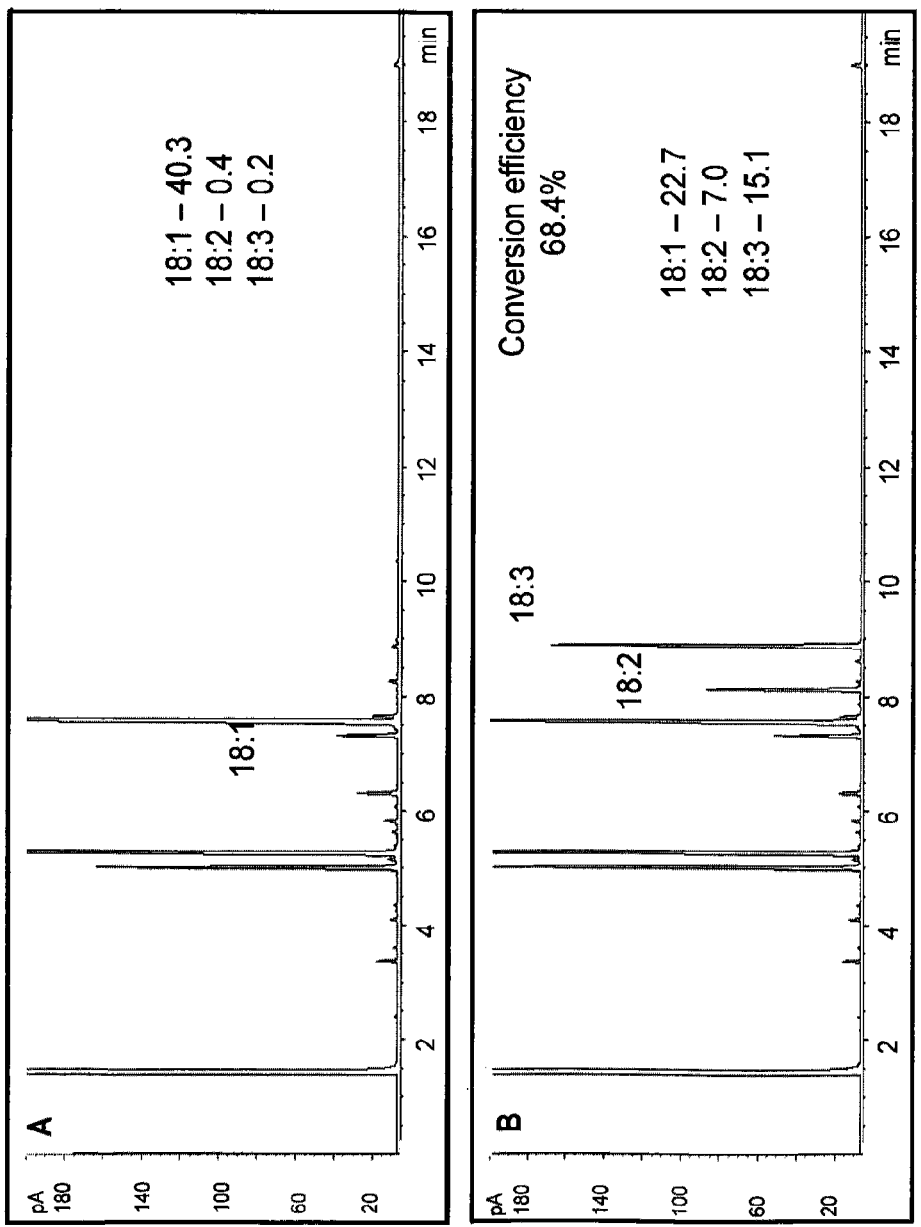
Figure 2: Functionality of Δ15-desaturase from *L. roseipellis* in a yeast feeding experiment in the presence of 18:1 (A) and 18:2 (B).

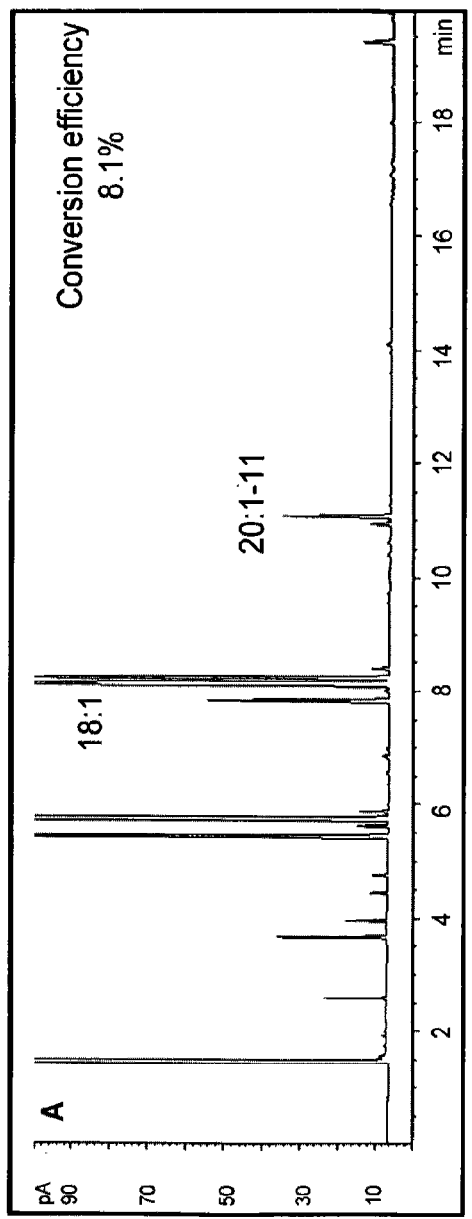
Figure 3 (A): Functionality of multi-elongase Δ6Elo(Sa) from *S. arctica* in yeast feeding experiments in the presence of no added fatty acids (A).

Figure 3 (B), (C): Functionality of multi-elongase Δ6Elo(Sa) from *S. arctica* in yeast feeding experiments in the presence of GLA added (B), SDA added (C).
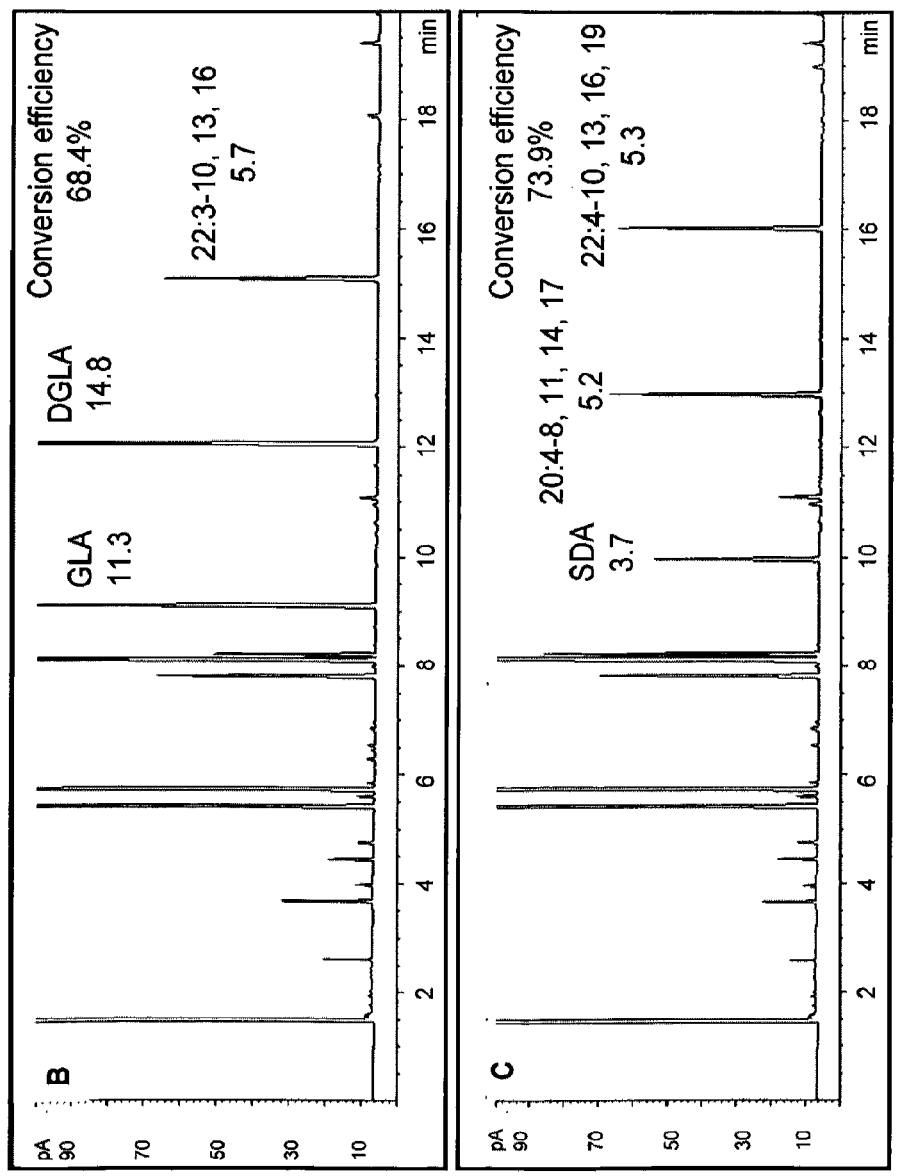

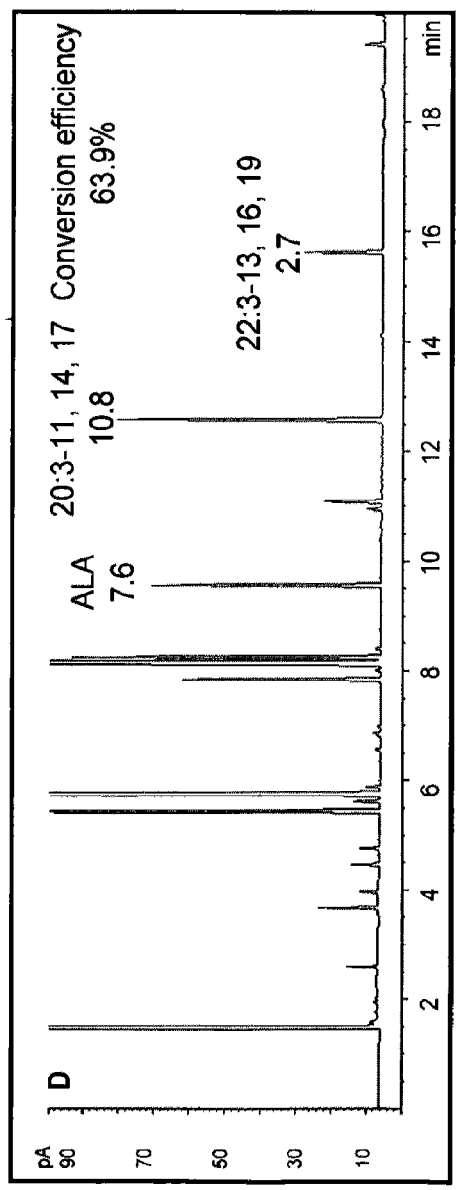
Figure 3 (D): Functionality of multi-elongase Δ6Elo(Sa) from *S. arctica* in yeast feeding experiments in the presence of ALA added (D).

Figure 3 (E), (F): Functionality of multi-elongase Δ6Elo(Sa) from *S. arctica* in yeast feeding experiments in the presentce of ARA added (E) and EPA added (F).
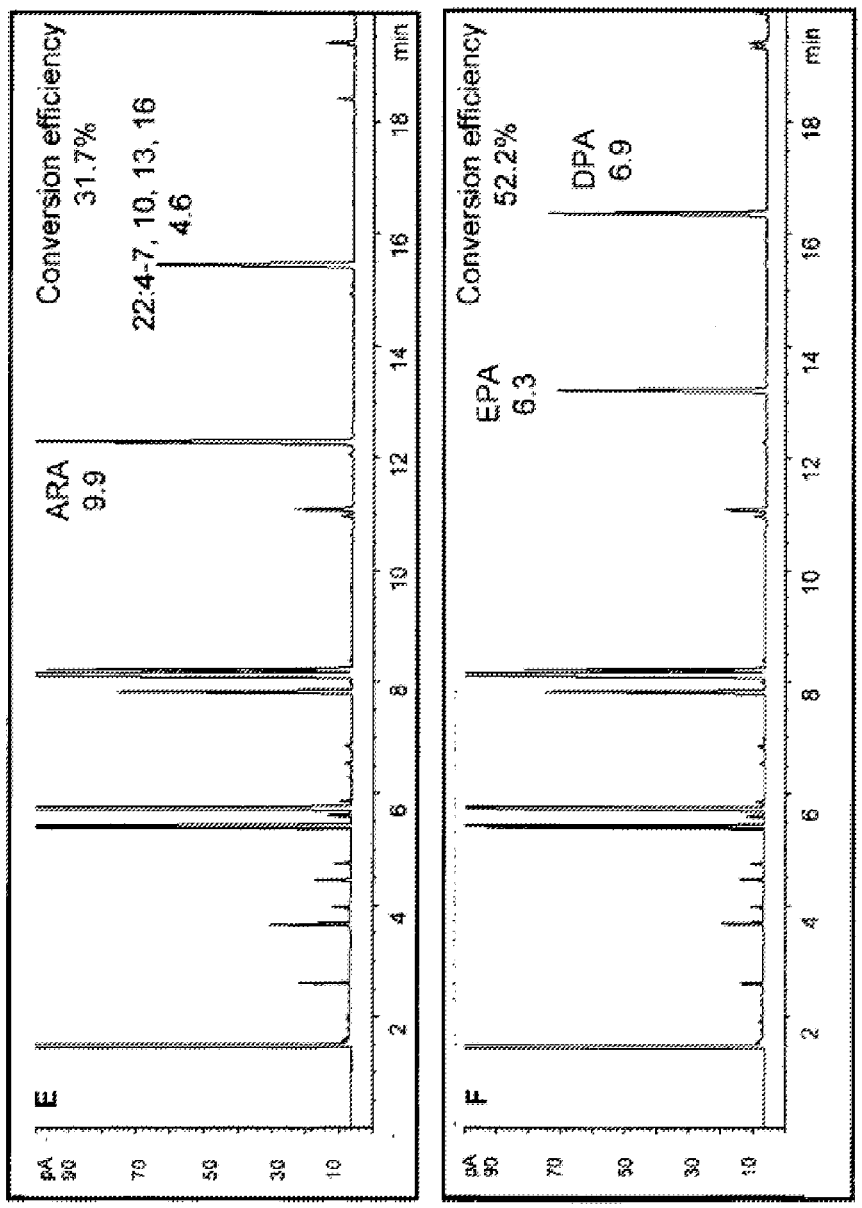

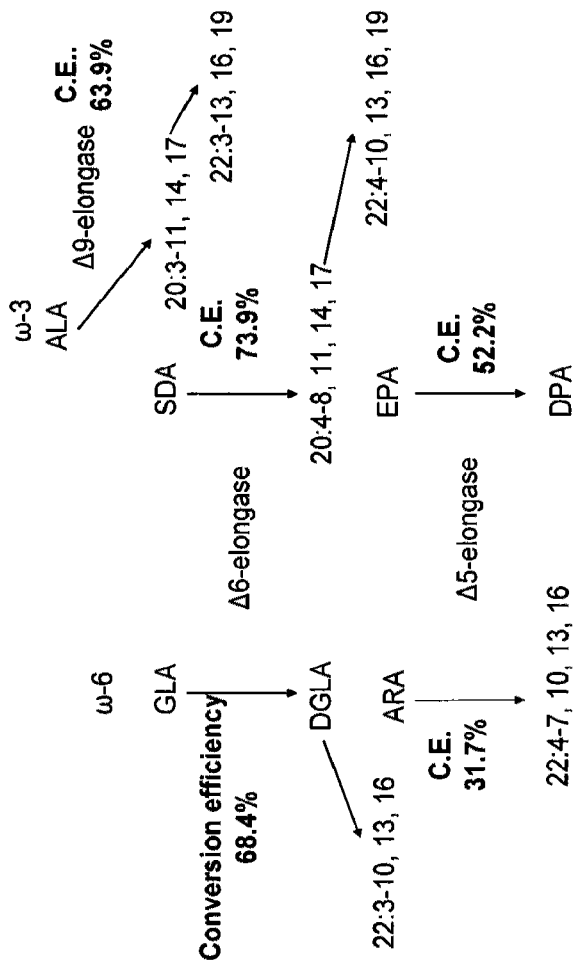
Figure 4: Overview of the activities of the Δ6Elo(Sa). The numbers in percentage give the different conversion rates.

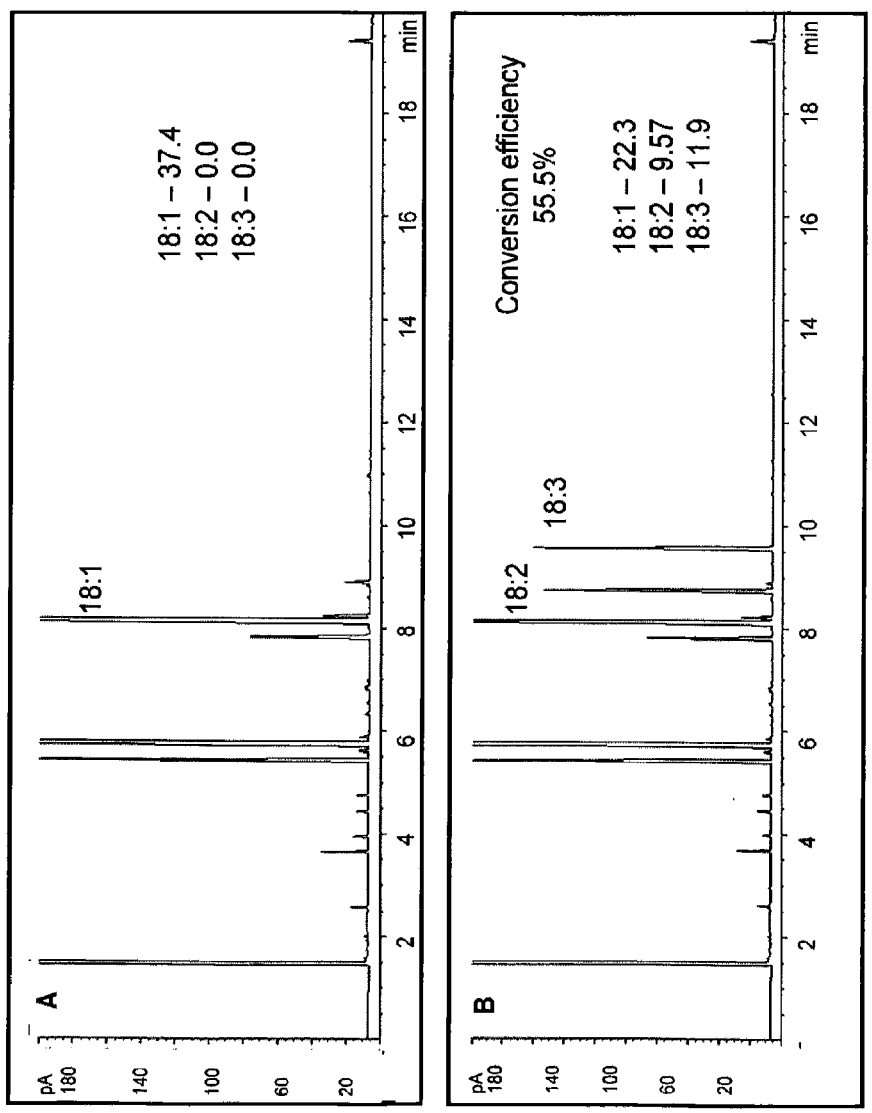
Figure 5: Functionality of Δ15-desaturase from S. arctica in a yeast feeding experiment in the presence of 18:1 (A) and 18:2 (B).

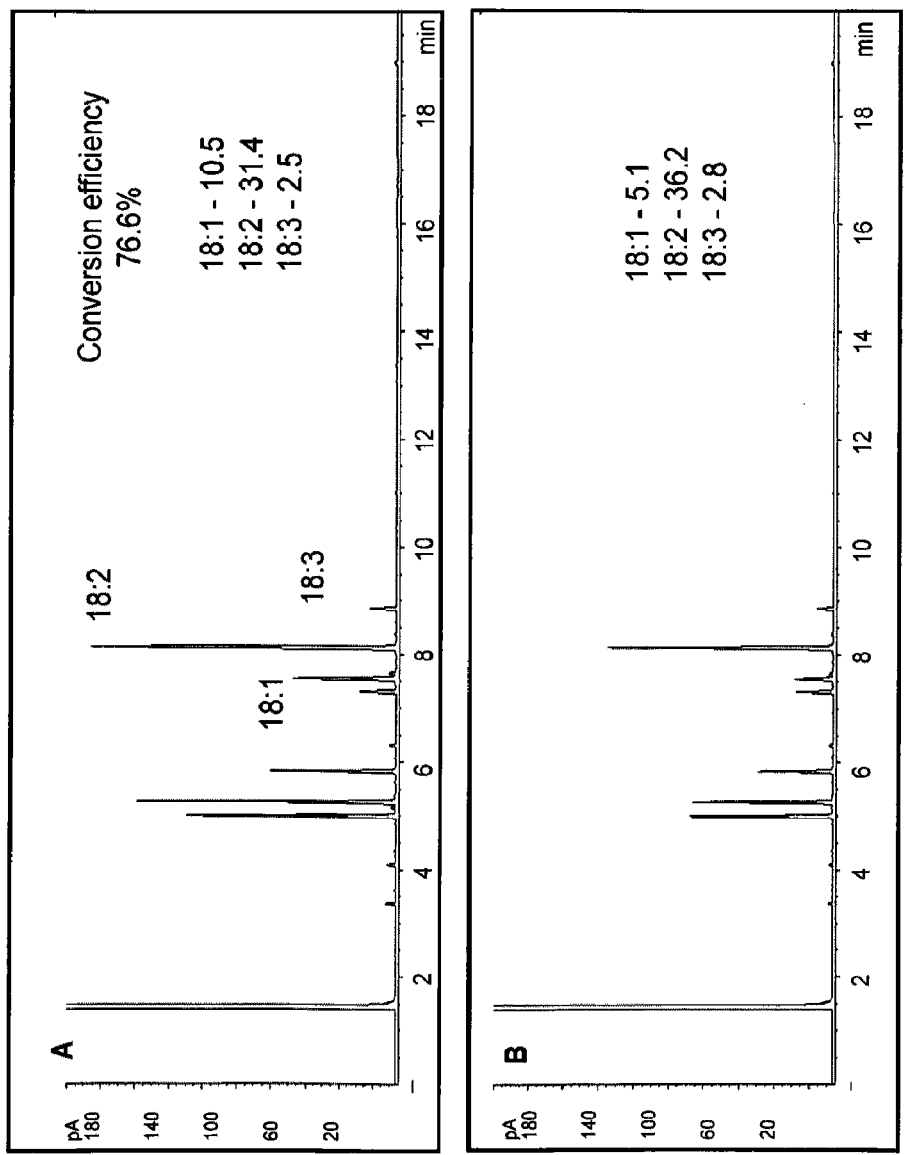
Figure 6: Functionality of Δ12/Δ15-desaturase from *L. fuciformis* in a yeast feeding experiment in the presence of 18:1 (A) and 18:2 (B).

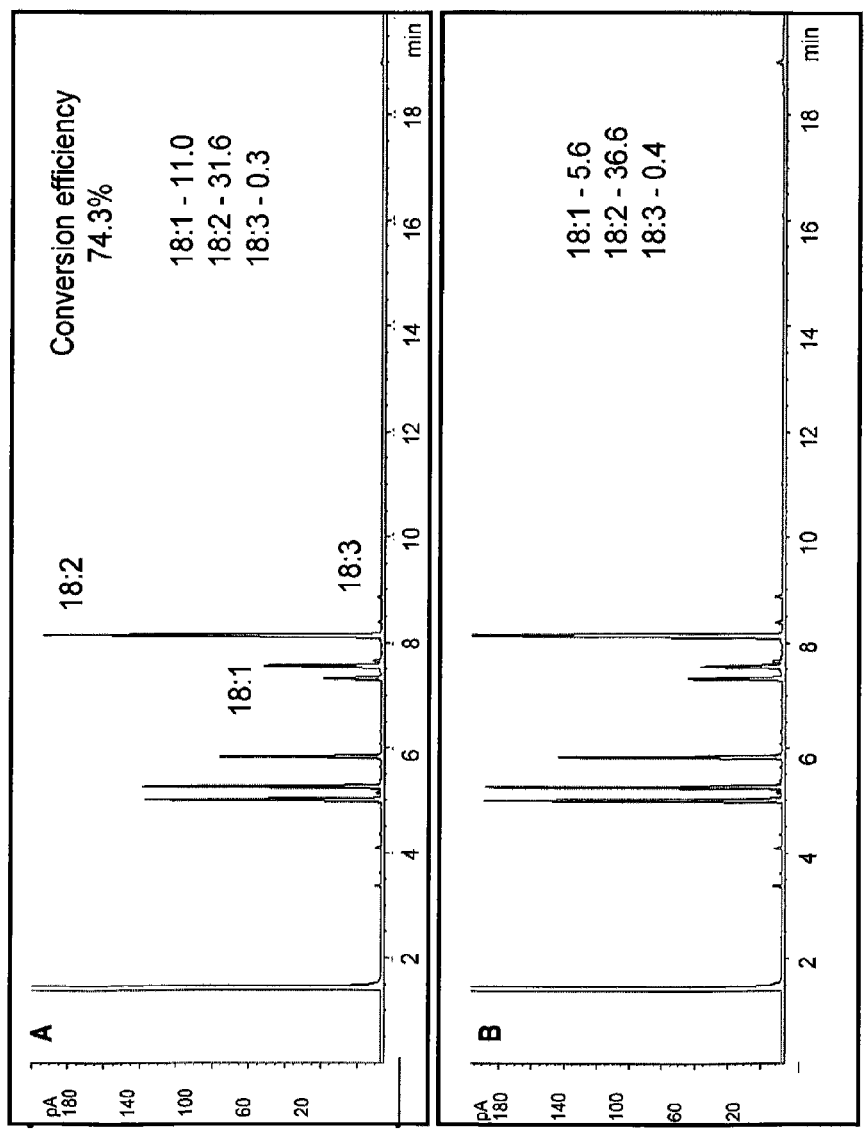
Figure 7: Functionality of Δ12-desaturase from *L. fuciformis* in a yeast feeding experiment in the presence of 18:1 (A) and 18:2 (B).

Figure 8: Functionality of Δ12-desaturase from *T. brevicollis* in a yeast feeding experiment in the presence of 18:1 (A) and 18:2 (B).
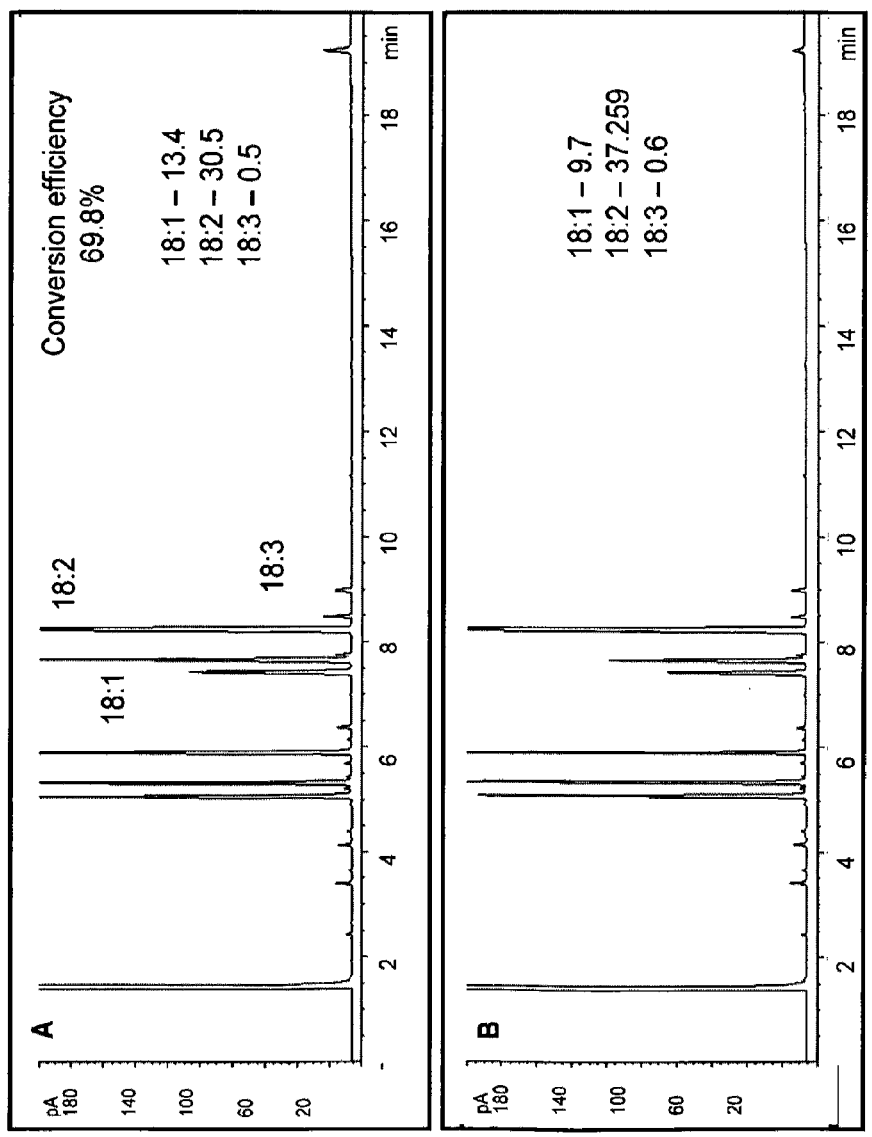

Figure 9 (A): Functionality of Δ8-desaturase from *S. arctica* in a yeast feeding experiment. Table (A) shows the used substrates and found products. The chromatograms (B) give the details for the found products.

A

| Fed | Substrate | Product | Conversion |
|---|---|---|---|
| DPA n-3 | 9.641 | - | - |
| ALA | 19.609 | - | - |
| 18:2 (LA) | 15.579 | - | - |
| HGLA | 12.212 | - | - |
| GLA | 25.212 | - | - |
| 20:3n-3 | 8.852 | 3.234 | 27% |
| 20:2n-6 | 4.367 | 1.097 | 20% |

Figure 10: Functionality of Δ5-desaturase from *S. arctica* in a yeast feeding experiment. Table (A) shows the used substrates and found products. The chromatograms (B) give the details for the found products.
A
| Fed | Substrate | Product | Conversion |
|---|---|---|---|
| DPA n-3 | 8.142 | - | - |
| HGLA | 3.662 | 1.975 | 35 % |
B
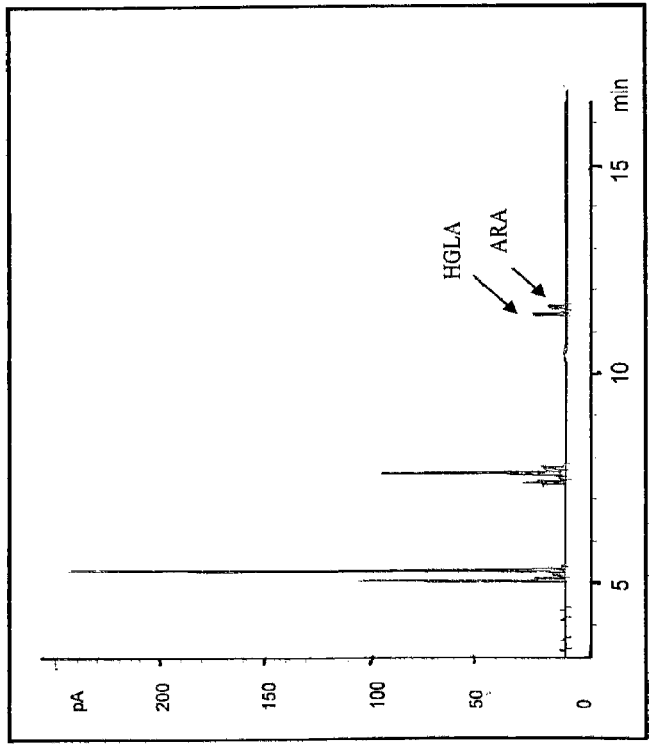

SEQUENCE LISTING

```
<160> NUMBER OF SEQ ID NOS: 56

<210> SEQ ID NO 1
<211> LENGTH: 1320
<212> TYPE: DNA
<213> ORGANISM: Limonomyces roseipellis

<400> SEQUENCE: 1
atggacacca cagatgcacg attcgggaag acggctaagc tgcaggaagt tactatccct      60
gacattacca taaaggatct cttgtcggcg atccctgcac actgctttaa acggtctgct     120
ctacgctctt gcagctatgt cgtttgggac ttctttctcc tcggttgctt ctacaaggca     180
gtcaaatctg tcgactcgct gattgacgcc gttacgtggt cccatccgtg gctcccaaca     240
ttggctcggg tttctctctg gtctgtctac ggtctcgcag ccggactcgt cggtaccggt     300
atttggatcc ttgcacatga atgtggtcac caggctttct cggagtcgaa gactctcaat     360
aatattatgg gctggttctt gcactcttcg gtcggggtcc cttaccactc gtggcgtata     420
tcgcatgcca aacatcatgc acaaacctcc cacatgaccg aagatcaggc ttatgttccc     480
cggacacgtt cggatcgcca gctcccggcg ttcaaccctg aacaggaaac cctcgagggc     540
tcacgagtct cgaccgaggt tatgcatgcg ttccatgagg ctctgagcga ctccctatc      600 agtgctgcac taggcggttt caaatatctt ctcttcggat ggccttctta tcttctctat     660
aatgcatctg gcaacgccg ttaccctgcg ggcaccaacc acttcaatcc taattctaag      720
gccatcttcc gcgataatca atatgggcag atcgtcattt ctgacatagg tatccttctt     780
tggctgggcg ctattgttac cttcggttat taccaaggat tcttggaagt attccgagtt     840
tacctggtgc catatctgtg ggtcaatcac tggatcgttc ttatcacttt ccttcagcac     900
acagaccctg tactgccaca ctaccgtgcc gctgagcaca cgttcccgcg tggagctttg     960
tccactctcg accgtactct tctcggcgac ttgggcagta ttgcgggctg gatcggcgag    1020
actgccacgc acggtatctc cgccacacac gttgtgcacc acgtcagctc gaagatcccc    1080
cactaccacg cctgggatgc cacatacgca ctccgggctc gtcttgctca ggacggcatc    1140
cacctcgagg gtcggcccgg tggttgggct gaggttgtcc gcgtgtatcg ttcctgtcaa    1200
ttcgttgagg atgaaggcga tattctgttc tacagaacg cacacggcct ggcggcggct      1260
aagcctgcga tcaccgaggt gactgactcc ggcgtcgaag tggacaggga ttcggattga    1320

<210> SEQ ID NO 2
<211> LENGTH: 439
<212> TYPE: PRT
<213> ORGANISM: Limonomyces roseipellis

<400> SEQUENCE: 2

Met Asp Thr Thr Asp Ala Arg Phe Gly Lys Thr Ala Lys Leu Gln Glu
1               5                   10                  15

Val Thr Ile Pro Asp Ile Thr Ile Lys Asp Leu Leu Ser Ala Ile Pro
            20                  25                  30
```

-continued

```
Ala His Cys Phe Lys Arg Ser Ala Leu Arg Ser Cys Ser Tyr Val Val
     35                  40                  45

Trp Asp Phe Phe Leu Leu Gly Cys Phe Tyr Lys Ala Val Lys Ser Val
50                  55                  60

Asp Ser Leu Ile Asp Ala Val Thr Trp Ser His Pro Trp Leu Pro Thr
65                  70                  75                  80

Leu Ala Arg Val Ser Leu Trp Ser Val Tyr Gly Leu Ala Ala Gly Leu
                 85                  90                  95

Val Gly Thr Gly Ile Trp Ile Leu Ala His Glu Cys Gly His Gln Ala
             100                 105                 110

Phe Ser Glu Ser Lys Thr Leu Asn Asn Ile Met Gly Trp Phe Leu His
         115                 120                 125

Ser Ser Val Gly Val Pro Tyr His Ser Trp Arg Ile Ser His Ala Lys
130                 135                 140

His His Ala Gln Thr Ser His Met Thr Glu Asp Gln Ala Tyr Val Pro
145                 150                 155                 160

Arg Thr Arg Ser Asp Arg Gln Leu Pro Ala Phe Asn Pro Glu Gln Glu
                165                 170                 175

Thr Leu Glu Gly Ser Arg Val Ser Thr Glu Val Met His Ala Phe His
             180                 185                 190

Glu Ala Leu Ser Asp Ser Pro Ile Ser Ala Ala Leu Gly Gly Phe Lys
         195                 200                 205

Tyr Leu Leu Phe Gly Trp Pro Ser Tyr Leu Leu Tyr Asn Ala Ser Gly
210                 215                 220

Gln Arg Arg Tyr Pro Ala Gly Thr Asn His Phe Asn Pro Asn Ser Lys
225                 230                 235                 240

Ala Ile Phe Arg Asp Asn Gln Tyr Gly Gln Ile Val Ile Ser Asp Ile
                245                 250                 255

Gly Ile Leu Leu Trp Leu Gly Ala Ile Val Thr Phe Gly Tyr Tyr Gln
             260                 265                 270

Gly Phe Leu Glu Val Phe Arg Val Tyr Leu Val Pro Tyr Leu Trp Val
         275                 280                 285

Asn His Trp Ile Val Leu Ile Thr Phe Leu Gln His Thr Asp Pro Val
290                 295                 300

Leu Pro His Tyr Arg Ala Ala Glu His Thr Phe Pro Arg Gly Ala Leu
305                 310                 315                 320

Ser Thr Leu Asp Arg Thr Leu Leu Gly Asp Leu Gly Ser Ile Ala Gly
                325                 330                 335

Trp Ile Gly Glu Thr Ala Thr His Gly Ile Ser Ala Thr His Val Val
             340                 345                 350

His His Val Ser Ser Lys Ile Pro His Tyr His Ala Trp Asp Ala Thr
         355                 360                 365

Tyr Ala Leu Arg Ala Arg Leu Ala Gln Asp Gly Ile His Leu Glu Gly
370                 375                 380

Arg Pro Gly Gly Trp Ala Glu Val Val Arg Val Tyr Arg Ser Cys Gln
385                 390                 395                 400

Phe Val Glu Asp Glu Gly Asp Ile Leu Phe Tyr Lys Asn Ala His Gly
                405                 410                 415

Leu Ala Ala Ala Lys Pro Ala Ile Thr Glu Val Thr Asp Ser Gly Val
             420                 425                 430

Glu Val Asp Arg Asp Ser Asp
             435
```

<210> SEQ ID NO 3
<211> LENGTH: 870
<212> TYPE: DNA
<213> ORGANISM: Sphaeroforma arctica

<400> SEQUENCE: 3

```
atggctcaaa tacaaaatat tacacggtcg ttcgccgatt tccaagggga ggatggagat      60
tacaccaatg ccccactcat gtcatttcag gcgcttatcg tcatggcaat cgtatactta     120
gtattacgat ttggacttga aaagtatatg gtagacaaaa aaccagttga tacgcagttt     180
cctgctatgg tttctaacgc gctcctggca gtaggttcgg catggatgtt ttggggattt     240
gcttcacaat tatacgagaa ctggtcggca gaaaactggg atcttaatct cctcgtgtgt     300
gatcctgatc tgaagctgca aaacagcatg gacaagttca tacgtgttt ctaccttagc     360
aagttttggg aatatatcga taccctattc ctgatcttgg gcaagaagca ggtcatcgga     420
cttcactggt tccaccactt gattactcca tctatctgct gggttgccta ccagtaccct     480
ggtgcttgtg catggatggg accgctttca aatgcgttcg tccatgtctg catgtatact     540
tactatacac tgacttactt ctctatgccg agaactttcg ggaaatacat cactcagatt     600
caaatcacac agttccttgg caatgttatg ctgtttacgg tcatattcgc gaacttgttg     660
tttggccagg ggcatcagca atgcggtgga tcgtggttat tctacattta cgtgatggcc     720
aattatgtaa acttcttgtt tatgttcaaa tcattcaaca cggcacgctt ggccaagctg     780
aataagaaga aacgtgccgc gcaactggaa cgtgagtcaa aggctgcgtt tgctgaggcg     840
gcacttgatg agcagaagaa gagtaggtaa                                       870
```

<210> SEQ ID NO 4
<211> LENGTH: 289
<212> TYPE: PRT
<213> ORGANISM: Sphaeroforma arctica

<400> SEQUENCE: 4

```
Met Ala Gln Ile Gln Asn Ile Thr Arg Ser Phe Ala Asp Phe Gln Gly
1               5                   10                  15

Glu Asp Gly Asp Tyr Thr Asn Ala Pro Leu Met Ser Phe Gln Ala Leu
            20                  25                  30

Ile Val Met Ala Ile Val Tyr Leu Val Leu Arg Phe Gly Leu Glu Lys
        35                  40                  45

Tyr Met Val Asp Lys Lys Pro Val Asp Thr Gln Phe Pro Ala Met Val
    50                  55                  60

Ser Asn Ala Leu Leu Ala Val Gly Ser Ala Trp Met Phe Trp Gly Phe
65                  70                  75                  80

Ala Ser Gln Leu Tyr Glu Asn Trp Ser Ala Glu Asn Trp Asp Leu Asn
                85                  90                  95

Leu Leu Val Cys Asp Pro Asp Leu Lys Leu Gln Asn Ser Met Asp Lys
            100                 105                 110

Phe Ile Tyr Val Phe Tyr Leu Ser Lys Phe Trp Glu Tyr Ile Asp Thr
        115                 120                 125

Leu Phe Leu Ile Leu Gly Lys Lys Gln Val Ile Gly Leu His Trp Phe
    130                 135                 140

His His Leu Ile Thr Pro Ser Ile Cys Trp Val Ala Tyr Gln Tyr Pro
145                 150                 155                 160

Gly Ala Cys Ala Trp Met Gly Pro Leu Ser Asn Ala Phe Val His Val
                165                 170                 175

Cys Met Tyr Thr Tyr Tyr Thr Leu Thr Tyr Phe Ser Met Pro Arg Thr
```

```
            180                 185                 190
Phe Gly Lys Tyr Ile Thr Gln Ile Gln Ile Thr Gln Phe Leu Gly Asn
                195                 200                 205
Val Met Leu Phe Thr Val Ile Phe Ala Asn Leu Leu Phe Gly Gln Gly
            210                 215                 220
His Gln Gln Cys Gly Gly Ser Trp Leu Phe Tyr Ile Tyr Val Met Ala
225                 230                 235                 240
Asn Tyr Val Asn Phe Leu Phe Met Phe Lys Ser Phe Asn Thr Ala Arg
                245                 250                 255
Leu Ala Lys Leu Asn Lys Lys Arg Ala Ala Gln Leu Glu Arg Glu
            260                 265                 270
Ser Lys Ala Ala Phe Ala Glu Ala Ala Leu Asp Glu Gln Lys Lys Ser
            275                 280                 285
Arg
```

<210> SEQ ID NO 5
<211> LENGTH: 1104
<212> TYPE: DNA
<213> ORGANISM: Sphaeroforma arctica

<400> SEQUENCE: 5

```
atggctaagg tgcgtgctgc tatccctcct cactgctggg agatcagcac cgtcaaggga    60
ttgacctact agtacaaga tattgtttta atcggacttt gtatgcact gcgtgtgtac    120
ttgctttcag atttcatgtc tggtgcatac ggatcattgg tgtcagtatt tacaagacta    180
gtatggtgga atttaatggg tttccagttg tggtgcttgt ttatgattgg acacgacgcc    240
ggtcacggaa cattctccac cagcccggcg atcaacatga ttgtaggtca tgtggcgcac    300
gttccactat tagtaccgta ccacggctgg cgacaatcgc accgtattca ccatatgtac    360
cacaatgatc ttgatcggga taagacttgg acacctgtga aggagtctac agcaaagggc    420
tggaaggacg acaacacttg gtatggatca atacgtttca ctgcgttatc cttgctgatg    480
ttcccatact atctacttgt ggccgaggct ggagacttgg tctatggatc acacttcaat    540
ccgttcaatg aagtgctttt taaaaccacg cacgacagga tatgcgcaac agtaggaacc    600
gcatcgatcg ctgccttcct tatgtcggtt ttcagcttct ctgtggcgca cacgcctact    660
gtcctagcag gatttttgc attcgtagat tggtatttca tccctatat aatcttctca    720
atgtggctct ctctggtcac taatctgcac cacacacacc ccgagtcact attctaccgc    780
aacgctcagt ggtctttgt gaagggtgct gcgactactg ttgaccgtga ctttgggcct    840
ataatcaact actttatgca ccacatcgag acacacgtgt tgcaccatct cttcttcacc    900
aagatagcac attacaacct agtggaagcc acagagtacg ctaaaccggc tctgggtcat    960
cactacaaga aggatgtgcg aaatcctatt ctcgccttta tgtccgatat ggattactgc    1020
aagacagtca aggacgaagg agatgtgttg cacctcaacg agttcgtaag ctacaaggct    1080
aaatatatgc caaggagga atga                                          1104
```

<210> SEQ ID NO 6
<211> LENGTH: 367
<212> TYPE: PRT
<213> ORGANISM: Sphaeroforma arctica

<400> SEQUENCE: 6

```
Met Ala Lys Val Arg Ala Ala Ile Pro Pro His Cys Trp Glu Ile Ser
1               5                   10                  15
```

```
Thr Val Lys Gly Leu Thr Tyr Leu Val Gln Asp Ile Val Leu Ile Gly
             20                  25                  30
Leu Leu Tyr Ala Leu Arg Val Tyr Leu Leu Ser Asp Phe Met Ser Gly
         35                  40                  45
Ala Tyr Gly Ser Leu Val Ser Val Phe Thr Arg Leu Val Trp Trp Asn
     50                  55                  60
Leu Met Gly Phe Gln Leu Trp Cys Leu Phe Met Ile Gly His Asp Ala
 65                  70                  75                  80
Gly His Gly Thr Phe Ser Thr Ser Pro Ala Ile Asn Met Ile Val Gly
                 85                  90                  95
His Val Ala His Val Pro Leu Leu Val Pro Tyr His Gly Trp Arg Gln
            100                 105                 110
Ser His Arg Ile His His Met Tyr His Asn Asp Leu Asp Arg Asp Lys
        115                 120                 125
Thr Trp Thr Pro Val Lys Glu Ser Thr Ala Lys Gly Trp Lys Asp Asp
    130                 135                 140
Asn Thr Trp Tyr Gly Ser Ile Arg Phe Thr Ala Leu Ser Leu Leu Met
145                 150                 155                 160
Phe Pro Tyr Tyr Leu Leu Val Ala Glu Ala Gly Asp Leu Val Tyr Gly
                165                 170                 175
Ser His Phe Asn Pro Phe Asn Glu Val Leu Phe Lys Thr Thr His Asp
            180                 185                 190
Arg Ile Cys Ala Thr Val Gly Thr Ala Ser Ile Ala Ala Phe Leu Met
        195                 200                 205
Ser Val Phe Ser Phe Ser Val Ala His Thr Pro Thr Val Leu Ala Gly
    210                 215                 220
Phe Phe Ala Phe Val Asp Trp Tyr Phe Ile Pro Tyr Ile Ile Phe Ser
225                 230                 235                 240
Met Trp Leu Ser Leu Val Thr Asn Leu His His Thr His Pro Glu Ser
                245                 250                 255
Leu Phe Tyr Arg Asn Ala Gln Trp Ser Phe Val Lys Gly Ala Ala Thr
            260                 265                 270
Thr Val Asp Arg Asp Phe Gly Pro Ile Ile Asn Tyr Phe Met His His
        275                 280                 285
Ile Glu Thr His Val Leu His His Leu Phe Pro Thr Lys Ile Ala His
    290                 295                 300
Tyr Asn Leu Val Glu Ala Thr Glu Tyr Ala Lys Pro Ala Leu Gly His
305                 310                 315                 320
His Tyr Lys Lys Asp Val Arg Asn Pro Ile Leu Ala Phe Met Ser Asp
                325                 330                 335
Met Asp Tyr Cys Lys Thr Val Lys Asp Glu Gly Asp Val Leu His Leu
            340                 345                 350
Asn Glu Phe Val Ser Tyr Lys Ala Lys Tyr Met Pro Lys Glu Glu
        355                 360                 365

<210> SEQ ID NO 7
<211> LENGTH: 1320
<212> TYPE: DNA
<213> ORGANISM: Laetisaria fuciformis

<400> SEQUENCE: 7
atggccacca cggatgcatc ttttggcaag gctgtgaagc ttcaagaggt cactatccca      60
aatttgacca tcaaggacct tctctcagct attccttccc attgctttaa gcatctgct      120 cttcggtctg gtagctatgt tgcatgggac ttctgccttc tcgccgggtt ttacaaggct     180
```

```
gtgaaatatg tcgatcctct gattgatact ctatccctgc ccaacccatg gttaaacact    240
gctgctcgcg tgtcactttg gtcggtgtat ggcttcgcgg ccggacttgt gggcactggt    300
ctctgggtca ttgcccacga atgcggacac caggccttct cagagtcgaa atccatcaac    360
aatgcggtcg gctgggttct tcactcagca cttggtgtgc catatcactc gtggagaatc    420
acacacgcga acatcatgc ctcaacggct cacatgaccg aggatcaggt cttcgttccc    480
cggacccgct ctcaaaagaa gctgccgccc ttcaggcctg atcaagaaaa cctggaagga    540
tctcaggtat ccgcacaagt catgcatgaa ttgcgcgatg cactgggtga ttcgcctatt    600
ggggccgccc ttggtggttt cacctatctg cttgccggat ggccatcata tctcattcgc    660
aacgcctctg gtcaaaaacg ctatgcctct ggaactaacc acttcaaccc ggatgccaag    720
gagattttcc gtgacaatca atacggacaa gtggtcattt ctgacatcgg catcctcctc    780
tggcttgcag gaatgggtac attcgcgtac tctcagggct tctttgagct gttccgagtg    840
tatctcgttc catatctttg ggtaaaccat tggctggtct tgatcacctt ccttcagcac    900
accgatccgg tccttcctca ctaccgtgct gctgagcaca cttttccctcg cggagccctg    960 gctaccctcg atcgcacact tcttggtgac ttgggcagcg tggccggctg gatcggagag   1020
accgctactc atggcatttc tgccacgcac gtgttgcatc atgtcagctc caagatcccc   1080
cattacaacg catgggaggc aaccgacact cttcgggcac gtctcgctca ggacggcgtc   1140
aagcttcagg gtcgacctgg tggatggact gaagttggac gtgtgttccg cgcttgccgc   1200
ttcgtcgagg atgaggggga tatcgtgttc tacaagaacg ggctgggtct ggcggcttcg   1260
aagccagcag tccaggatgt gactgactcg ggagtcgagg ttgacaagga ttcggattaa   1320
```

<210> SEQ ID NO 8
<211> LENGTH: 439
<212> TYPE: PRT
<213> ORGANISM: Laetisaria fuciformis

<400> SEQUENCE: 8

```
Met Ala Thr Thr Asp Ala Ser Phe Gly Lys Ala Val Lys Leu Gln Glu
1               5                   10                  15

Val Thr Ile Pro Asn Leu Thr Ile Lys Asp Leu Leu Ser Ala Ile Pro
                20                  25                  30

Ser His Cys Phe Lys Arg Ser Ala Leu Arg Ser Gly Ser Tyr Val Ala
            35                  40                  45

Trp Asp Phe Cys Leu Leu Ala Gly Phe Tyr Lys Ala Val Lys Tyr Val
        50                  55                  60

Asp Pro Leu Ile Asp Thr Leu Ser Leu Pro Asn Pro Trp Leu Asn Thr
65                  70                  75                  80

Ala Ala Arg Val Ser Leu Trp Ser Val Tyr Gly Phe Ala Ala Gly Leu
                85                  90                  95

Val Gly Thr Gly Leu Trp Val Ile Ala His Glu Cys Gly His Gln Ala
            100                 105                 110

Phe Ser Glu Ser Lys Ser Ile Asn Asn Ala Val Gly Trp Val Leu His
        115                 120                 125

Ser Ala Leu Gly Val Pro Tyr His Ser Trp Arg Ile Thr His Ala Lys
    130                 135                 140

His His Ala Ser Thr Ala His Met Thr Glu Asp Gln Val Phe Val Pro
145                 150                 155                 160

Arg Thr Arg Ser Gln Lys Lys Leu Pro Pro Phe Arg Pro Asp Gln Glu
                165                 170                 175
```

```
Asn Leu Glu Gly Ser Gln Val Ser Ala Gln Val Met His Glu Leu Arg
            180                 185                 190

Asp Ala Leu Gly Asp Ser Pro Ile Gly Ala Ala Leu Gly Gly Phe Thr
        195                 200                 205

Tyr Leu Leu Ala Gly Trp Pro Ser Tyr Leu Ile Arg Asn Ala Ser Gly
    210                 215                 220

Gln Lys Arg Tyr Ala Ser Gly Thr Asn His Phe Asn Pro Asp Ala Lys
225                 230                 235                 240

Glu Ile Phe Arg Asp Asn Gln Tyr Gly Gln Val Val Ile Ser Asp Ile
                245                 250                 255

Gly Ile Leu Leu Trp Leu Ala Gly Met Gly Thr Phe Ala Tyr Ser Gln
            260                 265                 270

Gly Phe Phe Glu Leu Phe Arg Val Tyr Leu Val Pro Tyr Leu Trp Val
        275                 280                 285

Asn His Trp Leu Val Leu Ile Thr Phe Leu Gln His Thr Asp Pro Val
    290                 295                 300

Leu Pro His Tyr Arg Ala Ala Glu His Thr Phe Pro Arg Gly Ala Leu
305                 310                 315                 320

Ala Thr Leu Asp Arg Thr Leu Leu Gly Asp Leu Gly Ser Val Ala Gly
                325                 330                 335

Trp Ile Gly Glu Thr Ala Thr His Gly Ile Ser Ala Thr His Val Leu
            340                 345                 350

His His Val Ser Ser Lys Ile Pro His Tyr Asn Ala Trp Glu Ala Thr
        355                 360                 365

Asp Thr Leu Arg Ala Arg Leu Ala Gln Asp Gly Val Lys Leu Gln Gly
    370                 375                 380

Arg Pro Gly Gly Trp Thr Glu Val Gly Arg Val Phe Arg Ala Cys Arg
385                 390                 395                 400

Phe Val Glu Asp Glu Gly Asp Ile Val Phe Tyr Lys Asn Gly Leu Gly
                405                 410                 415

Leu Ala Ala Ser Lys Pro Ala Val Gln Asp Val Thr Asp Ser Gly Val
            420                 425                 430

Glu Val Asp Lys Asp Ser Asp
        435

<210> SEQ ID NO 9
<211> LENGTH: 1335
<212> TYPE: DNA
<213> ORGANISM: Laetisaria fuciformis

<400> SEQUENCE: 9
atggccacta ctaccaccac cacgacgaat gctgcgtatg caaaagtcat aaagcaggag    60
gagatcgtta ttcctgactt gtcggtcaag gatcttctgt ccgctatccc ggcccactgc   120
ttcaaacgct cagctctccg ctccggtagc tacgtggtat gggacgcgat ccttctcgct   180
tgcttctaca aggccgtcaa atccgccgac ccactcattg acacccttcc attgcccagc   240
ccataccttt acaccgccgc ccgattcgct ttgtggtcgg tgtacgggtt cgctgctggc   300
ttggtcgcga ccggactgtg ggtgattgcc catgagtgtg gtcatcaggc attctcagag   360
agcaagacta ttaataacac cgttggatgg attttgcact ctgcccttgg tgttccttac   420
cactcatggc gtatcaccca tgctaaacat cacgctgcca atgctcacat gactgaggac   480
caagtctttg tccacggac ccggtcagag cgtgggctgc ctgctttcaa gcccgagcag   540
gagacccttg agggatctaa ggtctccacc gctgtcatga acgagctgta cgaggctctc   600
```

```
ggtgactctc ccattggtgc cttccttggt ggaatgactt acactatctt cggctggccc    660
ttgtacctgc tcctcaacgc atccggccaa agccgctacc cagctggcac ccatcactac    720
aacccgaacg ccaagtcgat tttccgtgac aaccaataca gccaaatcat catctcggac    780
gttggcattc tgctctggct cgcaggcatc gctacgtaca tctacaaggc cggcttcgtc    840
gaatgtctcc gggtgtacct cgtgccttac ctgtgggtga accactggct cgtcctaatt    900
gtcttcctcc aacacaccga ccccgtcgtc ccgcactacc gcgccgggga atttacattc    960
ccccgcggtg cgctcgccac gctcgaccgc accctgctcg ccgaccttgg ctctgtcgca   1020
ggctggatcg gcgagaccgt cacccacggc atctcgtcca cccacgtcct gcaccacgtc   1080
agctcgaaga tcccgcacta taacgctttt gaggctacag atgctctccg cgctcgtttg   1140
gctaaggatg gtatcgtctt gcagggtcgg cctgggggat gggcagaact cgcgaggatc   1200
tacaaggagt gcaagtttgt tgaggacgaa ggcgagatcg tgttctacaa gaatgcgtat   1260
gggcttgcgc catgcaaggc ggctgtgact gtcgtgtctg attcgggtgt ggaagttgat   1320
cgggattcgg agtaa                                                    1335
```

```
<210> SEQ ID NO 10
<211> LENGTH: 444
<212> TYPE: PRT
<213> ORGANISM: Laetisaria fuciformis

<400> SEQUENCE: 10
```

Met Ala Thr Thr Thr Thr Thr Thr Asn Ala Ala Tyr Gly Lys Val
1               5                   10                  15

Ile Lys Gln Glu Glu Ile Val Ile Pro Asp Leu Ser Val Lys Asp Leu
            20                  25                  30

Leu Ser Ala Ile Pro Ala His Cys Phe Lys Arg Ser Ala Leu Arg Ser
        35                  40                  45

Gly Ser Tyr Val Val Trp Asp Ala Ile Leu Leu Ala Cys Phe Tyr Lys
    50                  55                  60

Ala Val Lys Ser Ala Asp Pro Leu Ile Asp Thr Leu Pro Leu Pro Ser
65                  70                  75                  80

Pro Tyr Leu Tyr Thr Ala Ala Arg Phe Ala Leu Trp Ser Val Tyr Gly
                85                  90                  95

Phe Ala Ala Gly Leu Val Ala Thr Gly Leu Trp Val Ile Ala His Glu
            100                 105                 110

Cys Gly His Gln Ala Phe Ser Glu Ser Lys Thr Ile Asn Asn Thr Val
        115                 120                 125

Gly Trp Ile Leu His Ser Ala Leu Gly Val Pro Tyr His Ser Trp Arg
    130                 135                 140

Ile Thr His Ala Lys His His Ala Ala Asn Ala His Met Thr Glu Asp
145                 150                 155                 160

Gln Val Phe Val Pro Arg Thr Arg Ser Glu Arg Gly Leu Pro Ala Phe
                165                 170                 175

Lys Pro Glu Gln Glu Thr Leu Glu Gly Ser Lys Val Ser Thr Ala Val
            180                 185                 190

Met Asn Glu Leu Tyr Glu Ala Leu Gly Asp Ser Pro Ile Gly Ala Phe
        195                 200                 205

Leu Gly Gly Met Thr Tyr Thr Ile Phe Gly Trp Pro Leu Tyr Leu Leu
    210                 215                 220

Leu Asn Ala Ser Gly Gln Ser Arg Tyr Pro Ala Gly Thr His His Tyr
225                 230                 235                 240

```
Asn Pro Asn Ala Lys Ser Ile Phe Arg Asp Asn Gln Tyr Ser Gln Ile
            245                 250                 255

Ile Ile Ser Asp Val Gly Ile Leu Leu Trp Leu Ala Gly Ile Ala Thr
            260                 265                 270

Tyr Ile Tyr Lys Ala Gly Phe Val Glu Cys Leu Arg Val Tyr Leu Val
            275                 280                 285

Pro Tyr Leu Trp Val Asn His Trp Leu Val Leu Ile Val Phe Leu Gln
            290                 295                 300

His Thr Asp Pro Val Val Pro His Tyr Arg Ala Gly Glu Phe Thr Phe
305                 310                 315                 320

Pro Arg Gly Ala Leu Ala Thr Leu Asp Arg Thr Leu Leu Ala Asp Leu
            325                 330                 335

Gly Ser Val Ala Gly Trp Ile Gly Glu Thr Val Thr His Gly Ile Ser
            340                 345                 350

Ser Thr His Val Leu His His Val Ser Ser Lys Ile Pro His Tyr Asn
            355                 360                 365

Ala Phe Glu Ala Thr Asp Ala Leu Arg Ala Arg Leu Ala Lys Asp Gly
            370                 375                 380

Ile Val Leu Gln Gly Arg Pro Gly Gly Trp Ala Glu Leu Ala Arg Ile
385                 390                 395                 400

Tyr Lys Glu Cys Lys Phe Val Glu Asp Glu Gly Glu Ile Val Phe Tyr
            405                 410                 415

Lys Asn Ala Tyr Gly Leu Ala Pro Cys Lys Ala Ala Val Thr Val Val
            420                 425                 430

Ser Asp Ser Gly Val Glu Val Asp Arg Asp Ser Glu
            435                 440

<210> SEQ ID NO 11
<211> LENGTH: 1437
<212> TYPE: DNA
<213> ORGANISM: Thielaviopsis basicola

<400> SEQUENCE: 11
atgacatcca ccgctctccc taagcgcgtt gcgctgcacc gcaaccctac caccgactcc      60
agcaacgtct cggcctctcc ctctcccttg acagccctc gtcactcgcc ctcatccacc      120
tctctctcgt ccatggagtc ggatgctgaa aaggagaatc agggcaagat gatcgacacc      180
tatggcaacg agttcaaaat ccccgactac accatcaagc agattcgtga tgctatccct      240
gctcactgct cgagcgctc cgccgtcaag agtttgtcct atgtggcccg ggatattgtc       300
gtcatcgcct ccatcttcta tgtctttcag aactttgtga ccccgaaaa cgtgccttct       360 taccctctcc ggtttgccct gtggggcctg tacactattc ttcagggtct cttcggtacc      420
ggtatctggg ttttggctca cgagtgtggt caccaggcgt tctcgccttc caagaggctg      480
aacgacactg tcggttggat ctgccactct gctctgctcg tcccttactt ctcgtggaag      540
atctcccacg gaaagcacca caaggccact ggtaacatcg tcgtgacat ggttttcgtc       600 cccaagacgc gtcctgagta tgcctcccgc gttggcaagg ctatccatga attgaacgag      660
ctgctcgaag agaccccctt cctgaccgcc agcaacgtta tcatgcaaca gctgttcggt      720
tggcccatgt acctcctcac caacgttact ggccacaaca accatgagaa ccagcccgag      780
ggccgtggca gggcaagcg caacggctac tttagcggtg tcaaccactt caaccccctcc      840 agccctctct atgaggccaa ggacgccaaa ctcattctcc tgagtgacct cggtctcgct      900
atcaccggtt cagtcctgta cttcatcggt accaactatg gctggctcaa cttgctcgtg      960
```

```
tggtatggaa ttccttacct ctgggtgaac cactggcttg tggccatcac ttacctccaa      1020
cacaccgacc cctccctccc ccactaccag cctgaggtct ggaactttgc ccgtggtgct      1080
gctgccacca tcgaccgtga ttttggtttc gtcggccgcc acatcctcca cggaatcatc      1140
gagacccacg tcctccacca ctatgtcagc accatcccct tctacaacgc cgacgaagcc      1200
agcgaggcca tcaagaaggt catgggcagc cactaccgca ccgaggcccc caccggctgg      1260
actggattct tcaaggctat gtggactagc gctcgcacct gccagtgggt tgagcccacc      1320
gagggtgcca agggcgaggg ccaaggtgtg ctcttctacc gcaacaccaa cggcattggt      1380
tccctccggc caaggttgct gccaattaag tcaagagaaa gcaaagggcg agcttaa        1437
```

<210> SEQ ID NO 12
<211> LENGTH: 478
<212> TYPE: PRT
<213> ORGANISM: Thielaviopsis basicola

<400> SEQUENCE: 12

```
Met Thr Ser Thr Ala Leu Pro Lys Arg Val Ala Leu His Arg Asn Pro
1               5                   10                  15

Thr Thr Asp Ser Ser Asn Val Ser Ala Ser Pro Ser Pro Leu Asp Ser
            20                  25                  30

Pro Arg His Ser Pro Ser Ser Thr Ser Leu Ser Ser Met Glu Ser Asp
        35                  40                  45

Ala Glu Lys Glu Asn Gln Gly Lys Met Ile Asp Thr Tyr Gly Asn Glu
    50                  55                  60

Phe Lys Ile Pro Asp Tyr Thr Ile Lys Gln Ile Arg Asp Ala Ile Pro
65                  70                  75                  80

Ala His Cys Phe Glu Arg Ser Ala Val Lys Ser Leu Ser Tyr Val Ala
                85                  90                  95

Arg Asp Ile Val Val Ile Ala Ser Ile Phe Tyr Val Phe Gln Asn Phe
            100                 105                 110

Val Thr Pro Glu Asn Val Pro Ser Tyr Pro Leu Arg Phe Ala Leu Trp
        115                 120                 125

Gly Leu Tyr Thr Ile Leu Gln Gly Leu Phe Gly Thr Gly Ile Trp Val
    130                 135                 140

Leu Ala His Glu Cys Gly His Gln Ala Phe Ser Pro Ser Lys Arg Leu
145                 150                 155                 160

Asn Asp Thr Val Gly Trp Ile Cys His Ser Ala Leu Leu Val Pro Tyr
                165                 170                 175

Phe Ser Trp Lys Ile Ser His Gly Lys His His Lys Ala Thr Gly Asn
            180                 185                 190

Ile Ala Arg Asp Met Val Phe Val Pro Lys Thr Arg Pro Glu Tyr Ala
        195                 200                 205

Ser Arg Val Gly Lys Ala Ile His Glu Leu Asn Glu Leu Leu Glu Glu
    210                 215                 220

Thr Pro Phe Leu Thr Ala Ser Asn Val Ile Met Gln Gln Leu Phe Gly
225                 230                 235                 240

Trp Pro Met Tyr Leu Leu Thr Asn Val Thr Gly His Asn Asn His Glu
                245                 250                 255

Asn Gln Pro Glu Gly Arg Gly Lys Gly Lys Arg Asn Gly Tyr Phe Ser
            260                 265                 270

Gly Val Asn His Phe Asn Pro Ser Ser Pro Leu Tyr Glu Ala Lys Asp
        275                 280                 285
```

```
Ala Lys Leu Ile Leu Leu Ser Asp Leu Gly Leu Ala Ile Thr Gly Ser
        290                 295                 300

Val Leu Tyr Phe Ile Gly Thr Asn Tyr Gly Trp Leu Asn Leu Val
305                 310                 315                 320

Trp Tyr Gly Ile Pro Tyr Leu Trp Val Asn His Trp Leu Val Ala Ile
                325                 330                 335

Thr Tyr Leu Gln His Thr Asp Pro Ser Leu Pro His Tyr Gln Pro Glu
            340                 345                 350

Val Trp Asn Phe Ala Arg Gly Ala Ala Thr Ile Asp Arg Asp Phe
                355                 360                 365

Gly Phe Val Gly Arg His Ile Leu His Gly Ile Glu Thr His Val
370                 375                 380

Leu His His Tyr Val Ser Thr Ile Pro Phe Tyr Asn Ala Asp Glu Ala
385                 390                 395                 400

Ser Glu Ala Ile Lys Lys Val Met Gly Ser His Tyr Arg Thr Glu Ala
                405                 410                 415

Pro Thr Gly Trp Thr Gly Phe Phe Lys Ala Met Trp Ser Ala Arg
            420                 425                 430

Thr Cys Gln Trp Val Glu Pro Thr Glu Gly Ala Lys Gly Glu Gly Gln
            435                 440                 445

Gly Val Leu Phe Tyr Arg Asn Thr Asn Gly Ile Gly Ser Leu Arg Pro
450                 455                 460

Arg Leu Leu Pro Ile Lys Ser Arg Glu Ser Lys Gly Arg Ala
465                 470                 475

<210> SEQ ID NO 13
<211> LENGTH: 1323
<212> TYPE: DNA
<213> ORGANISM: Sphaeroforma arctica

<400> SEQUENCE: 13
atgtgtaaat cacagaaaca gtacacctgg gaagaggtcg ccgagcacaa cagtgcggat      60
gatctttatg tcgctatccg aggaaaggta tacgatgtca cgaagttcaa agatacgcac     120
cccgggggtt tagagacatt acttgcagcg gggggccgtg atgccacaca ggttttcgag     180
acgtaccact cctttcgagt gaaggagctc cttcataaat acgaagtcgg ccatttggtg     240
accaatgagt tgcccacctt ccctgcacct aacgagttct tcgtagctgt caagtcgcga     300
gttgacgact acttcaagaa gacaaagcaa acccctaagt acaaccactg gatgctggtg     360
cgatacttcg caatcttcgg tactatcttt ggctcgtggg ctatcacctt aaacaccgat     420
tcactacctc tgcagctact gctttgcttg ccgctcggtc ttgcctgtgc tatggtaggc     480
ctgatgccaa tgcatgacag ctcgcacttc tccttcacac acaacccccac agtatggttt     540
gcgctcggcg ccacccacga ttttgtcaac ggagcgtcct atctgtgctg gttgtaccag     600
cacatgttag gtcaccatcc ctacacaaat atcgatggtg ctgatcctga tattgtcaca     660
agtgaaaatg acgtgcggag aatcaagaca tctcagccat ggtacagctt ctatgttaat     720
cagcacatct atgtgcccat cctgtacgcc gtgctgggac tcaagacccg tttccaggac     780
gtcaccatcg tattcggttc caagatgaac ggtgccatcc gcgtcaacaa tccgtcaccc     840
gcccagacct acgtcttttg gggtggcaaa gtgttttttg ccctgtatcg gcttgtgcta     900
cctctggcat tgggcatgag tttattgcgt gttattggtc ttttcctgct gtccgatgcc     960
gtgacctcgt actggctggc gttgacattc aggctaacc atgtggtgga ggatgtggcg    1020
tggcctgagc tggactcaaa gggaaacatc ctaagggact gggctgagca ccaggtggac    1080
```

```
acaacgcaag actacgcaca cgaatcctgg ttctggaatg tgttctccgg tgcactaaac   1140
catcagacca ctcaccatat agtaccacag gtcaatcagt actactatcc agagatcagt   1200
cccatcgtgc gacaggctgc caaggaattt aacatcccgt accattacaa agagacttac   1260
tcagaggcca taggtggaca cctgcagcat ctatacaatc tgggccataa gacaaaggaa   1320
tga                                                                 1323
```

<210> SEQ ID NO 14
<211> LENGTH: 440
<212> TYPE: PRT
<213> ORGANISM: Sphaeroforma arctica

<400> SEQUENCE: 14

```
Met Cys Lys Ser Gln Lys Gln Tyr Thr Trp Glu Glu Val Ala Glu His
1               5                   10                  15

Asn Ser Ala Asp Asp Leu Tyr Val Ala Ile Arg Gly Lys Val Tyr Asp
            20                  25                  30

Val Thr Lys Phe Lys Asp Thr His Pro Gly Gly Leu Glu Thr Leu Leu
        35                  40                  45

Ala Ala Gly Gly Arg Asp Ala Thr Gln Val Phe Glu Thr Tyr His Ser
    50                  55                  60

Phe Arg Val Lys Glu Leu Leu His Lys Tyr Glu Val Gly His Leu Val
65                  70                  75                  80

Thr Asn Glu Leu Pro Thr Phe Pro Ala Pro Asn Glu Phe Phe Val Ala
                85                  90                  95

Val Lys Ser Arg Val Asp Asp Tyr Phe Lys Lys Thr Lys Gln Asn Pro
            100                 105                 110

Lys Tyr Asn His Trp Met Leu Val Arg Tyr Phe Ala Ile Phe Gly Thr
        115                 120                 125

Ile Phe Gly Ser Trp Ala Ile Thr Leu Asn Thr Asp Ser Leu Pro Leu
    130                 135                 140

Gln Leu Leu Leu Cys Leu Pro Leu Gly Leu Ala Cys Ala Met Val Gly
145                 150                 155                 160

Leu Met Pro Met His Asp Ser Ser His Phe Ser Phe Thr His Asn Pro
                165                 170                 175

Thr Val Trp Phe Ala Leu Gly Ala Thr His Asp Phe Val Asn Gly Ala
            180                 185                 190

Ser Tyr Leu Cys Trp Leu Tyr Gln His Met Leu Gly His His Pro Tyr
        195                 200                 205

Thr Asn Ile Asp Gly Ala Asp Pro Asp Ile Val Thr Ser Glu Asn Asp
    210                 215                 220

Val Arg Arg Ile Lys Thr Ser Gln Pro Trp Tyr Ser Phe Tyr Val Asn
225                 230                 235                 240

Gln His Ile Tyr Val Pro Ile Leu Tyr Ala Val Leu Gly Leu Lys Thr
                245                 250                 255

Arg Phe Gln Asp Val Thr Ile Val Phe Gly Ser Lys Met Asn Gly Ala
            260                 265                 270

Ile Arg Val Asn Asn Pro Ser Pro Ala Gln Thr Tyr Val Phe Trp Gly
        275                 280                 285

Gly Lys Val Phe Phe Ala Leu Tyr Arg Leu Val Leu Pro Leu Ala Leu
    290                 295                 300

Gly Met Ser Leu Leu Arg Val Ile Gly Leu Phe Leu Leu Ser Asp Ala
305                 310                 315                 320
```

```
Val Thr Ser Tyr Trp Leu Ala Leu Thr Phe Gln Ala Asn His Val Val
            325                 330                 335

Glu Asp Val Ala Trp Pro Glu Leu Asp Ser Lys Gly Asn Ile Leu Arg
        340                 345                 350

Asp Trp Ala Glu His Gln Val Asp Thr Thr Gln Asp Tyr Ala His Glu
        355                 360                 365

Ser Trp Phe Trp Asn Val Phe Ser Gly Ala Leu Asn His Gln Thr Thr
    370                 375                 380

His His Ile Val Pro Gln Val Asn Gln Tyr Tyr Tyr Pro Glu Ile Ser
385                 390                 395                 400

Pro Ile Val Arg Gln Ala Ala Lys Glu Phe Asn Ile Pro Tyr His Tyr
                405                 410                 415

Lys Glu Thr Tyr Ser Glu Ala Ile Gly Gly His Leu Gln His Leu Tyr
            420                 425                 430

Asn Leu Gly His Lys Thr Lys Glu
        435                 440

<210> SEQ ID NO 15
<211> LENGTH: 1431
<212> TYPE: DNA
<213> ORGANISM: Sphaeroforma arctica

<400> SEQUENCE: 15
atggtacccc gagagcgctt gtctcacgat cctaccctga tggacgagac tgataactgc      60
gacagtacag tacaaaagaa aggtccctgc atagctgacc catcgcagcc aagcacattg     120
aatccgaatg tgtggtatct acatggtaaa gcctacgatt tcacagactt cgttaaaaga     180
catcccggag gcgaaaaagc catcttgatc ggacaagggc gtgactgtac tgaactcttc     240
gagtcgtatc acacattttt gccatccgac aaactactgg ccaagtacgc cctcgataaa     300
gaaggctctc tgggagatgg tagcaatgtg ctacaactgg ctcctgagat ggtacaattc     360
actttcaaag acgatggctt ttaccgcaca ctcaaacgaa gagctgcaga gcatttccgg     420
aaaacaaagt cgggaaccaa ggctggtata ttccataaaa ccgtaggcgt ggcgactatc     480
acgcttctgt ttgtgctggc ttattacggg ttttaccagg gagtgttctg ggccgcagca     540
ctacacggct tcctgagagc gatgataatt gtgcgcgatt gtcatgcgtc atcacactat     600
gcctggtcgt acaaccccac gatgaatcaa tggatgtatc gcatatctat ggcatttgcc     660
ggcagcagtc cctcacagtg gactgctaag cacgtggtgg ctcatcatgt ctccaccaac     720
atcacacccg tggatgatga taccatgtac cccatgaagc gtgtgctacc tgaactaccc     780
cgccggtcgt ggcacgcgtt ccagcaccta tacatctggg tattctactg tctgactatc     840
atgttctgga cattgtcgga tgtggtcaag ctggcaatcg tcactacta cgagggcacc     900 acacaggtgt cacactggag cactattgac tgggaggaga cgtacggggt gtatatattc     960
cacatagcgc acagatgggt gctgccgttc gtgtccctgc ccttctctca cgcaatgggt    1020
attgtgttgc tcaatgaagt cttcgccagt ctaccgtttg tgctacagtt cgtggtcaat    1080
cacgaggtgg agaccagcgt tgagcaggtg tctgtggact aaatgcgca gcagccgacc    1140 tcagagctat caggcacaga ttggggcgca catcaagtgc gtacatctca aactatggc    1200 gtgggcagcc cactgtggct gaactcctca ggtggcctga atatgcagat tgagcatcac    1260
ctgttcccgt ccgttcatca cagccactac caagcgctcg gcgaattgac aaggcgtaca    1320
tgcaaggagt tcaacgtccc atataacaca tctggaggtt tggcggaagc tttgggaaag    1380
cactatgact tgctcgtcaa gatgggccgt tcaccggaga tgaccacgta a             1431
```

<210> SEQ ID NO 16
<211> LENGTH: 476
<212> TYPE: PRT
<213> ORGANISM: Sphaeroforma arctica

<400> SEQUENCE: 16

```
Met Val Pro Arg Glu Arg Leu Ser His Asp Pro Thr Leu Met Asp Glu
1               5                   10                  15

Thr Asp Asn Cys Asp Ser Thr Val Gln Lys Lys Gly Pro Cys Ile Ala
            20                  25                  30

Asp Pro Ser Gln Pro Ser Thr Leu Asn Pro Asn Val Trp Tyr Leu His
        35                  40                  45

Gly Lys Ala Tyr Asp Phe Thr Asp Phe Val Lys Arg His Pro Gly Gly
    50                  55                  60

Glu Lys Ala Ile Leu Ile Gly Gln Gly Arg Asp Cys Thr Glu Leu Phe
65                  70                  75                  80

Glu Ser Tyr His Thr Phe Leu Pro Ser Asp Lys Leu Leu Ala Lys Tyr
                85                  90                  95

Ala Leu Asp Lys Glu Gly Ser Leu Gly Asp Gly Ser Asn Val Leu Gln
            100                 105                 110

Leu Ala Pro Glu Met Val Gln Phe Thr Phe Lys Asp Asp Gly Phe Tyr
        115                 120                 125

Arg Thr Leu Lys Arg Arg Ala Glu His Phe Arg Lys Thr Lys Ser
    130                 135                 140

Gly Thr Lys Ala Gly Ile Phe His Lys Thr Val Gly Val Ala Thr Ile
145                 150                 155                 160

Thr Leu Leu Phe Val Leu Ala Tyr Tyr Gly Phe Tyr Gln Gly Val Phe
                165                 170                 175

Trp Ala Ala Ala Leu His Gly Phe Leu Arg Ala Met Ile Ile Val Arg
            180                 185                 190

Asp Cys His Ala Ser Ser His Tyr Ala Trp Ser Tyr Asn Pro Thr Met
        195                 200                 205

Asn Gln Trp Met Tyr Arg Ile Ser Met Ala Phe Ala Gly Ser Ser Pro
    210                 215                 220

Ser Gln Trp Thr Ala Lys His Val Val Ala His His Val Ser Thr Asn
225                 230                 235                 240

Ile Thr Pro Val Asp Asp Thr Met Tyr Pro Met Lys Arg Val Leu
                245                 250                 255

Pro Glu Leu Pro Arg Arg Ser Trp His Ala Phe Gln His Leu Tyr Ile
            260                 265                 270

Trp Val Phe Tyr Cys Leu Thr Ile Met Phe Trp Thr Leu Ser Asp Val
        275                 280                 285

Val Lys Leu Ala Ile Gly His Tyr Tyr Glu Gly Thr Gln Val Ser
    290                 295                 300

His Trp Ser Thr Ile Asp Trp Glu Glu Thr Tyr Gly Val Tyr Ile Phe
305                 310                 315                 320

His Ile Ala His Arg Trp Val Leu Pro Phe Val Ser Leu Pro Phe Ser
                325                 330                 335

His Ala Met Gly Ile Val Leu Leu Asn Glu Val Phe Ala Ser Leu Pro
            340                 345                 350

Phe Val Leu Gln Phe Val Asn His Glu Val Glu Thr Ser Val Glu
        355                 360                 365

Gln Val Ser Val Asp Leu Asn Ala Gln Gln Pro Thr Ser Glu Leu Ser
```

```
                370                 375                 380
Gly Thr Asp Trp Gly Ala His Gln Val Arg Thr Ser His Asn Tyr Gly
385                 390                 395                 400

Val Gly Ser Pro Leu Trp Leu Asn Ser Ser Gly Gly Leu Asn Met Gln
                405                 410                 415

Ile Glu His His Leu Phe Pro Ser Val His His Ser His Tyr Gln Ala
            420                 425                 430

Leu Gly Glu Leu Thr Arg Arg Thr Cys Lys Glu Phe Asn Val Pro Tyr
        435                 440                 445

Asn Thr Ser Gly Gly Leu Ala Glu Ala Leu Gly Lys His Tyr Asp Leu
    450                 455                 460

Leu Val Lys Met Gly Arg Ser Pro Glu Met Thr Thr
465                 470                 475

<210> SEQ ID NO 17
<211> LENGTH: 18
<212> TYPE: DNA
<213> ORGANISM: Artificial sequence
<220> FEATURE:
<223> OTHER INFORMATION: Primer sequence (IUPAC standard nomenclature)

<400> SEQUENCE: 17
acggbttggr tbtgscay                                                   18

<210> SEQ ID NO 18
<211> LENGTH: 16
<212> TYPE: DNA
<213> ORGANISM: Artificial sequence
<220> FEATURE:
<223> OTHER INFORMATION: Primer sequence (IUPAC standard nomenclature)

<400> SEQUENCE: 18
sagarytkbg gtggsm                                                     16

<210> SEQ ID NO 19
<211> LENGTH: 17
<212> TYPE: DNA
<213> ORGANISM: Artificial sequence
<220> FEATURE:
<223> OTHER INFORMATION: Primer sequence (IUPAC standard nomenclature)

<400> SEQUENCE: 19
gtdatrvaca rccartg                                                    17

<210> SEQ ID NO 20
<211> LENGTH: 17
<212> TYPE: DNA
<213> ORGANISM: Artificial sequence
<220> FEATURE:
<223> OTHER INFORMATION: Primer sequence (IUPAC standard nomenclature)

<400> SEQUENCE: 20
rtgdwysayd atccrtg                                                    17

<210> SEQ ID NO 21
<211> LENGTH: 20
<212> TYPE: DNA
<213> ORGANISM: Artificial sequence
<220> FEATURE:
<223> OTHER INFORMATION: Primer sequence (IUPAC standard nomenclature)

<400> SEQUENCE: 21
atggacacca cagatgcacg                                                 20
```

```
<210> SEQ ID NO 22
<211> LENGTH: 21
<212> TYPE: DNA
<213> ORGANISM: Artificial sequence
<220> FEATURE:
<223> OTHER INFORMATION: Primer sequence (IUPAC standard nomenclature)

<400> SEQUENCE: 22
tcaatccgaa tccctgtcca c                                             21

<210> SEQ ID NO 23
<211> LENGTH: 20
<212> TYPE: DNA
<213> ORGANISM: Artificial sequence
<220> FEATURE:
<223> OTHER INFORMATION: Primer sequence (IUPAC standard nomenclature)

<400> SEQUENCE: 23
atggctcaaa tacaaaatat                                               20

<210> SEQ ID NO 24
<211> LENGTH: 21
<212> TYPE: DNA
<213> ORGANISM: Artificial sequence
<220> FEATURE:
<223> OTHER INFORMATION: Primer sequence (IUPAC standard nomenclature)

<400> SEQUENCE: 24
ttacctactc ttcttctgct c                                             21

<210> SEQ ID NO 25
<211> LENGTH: 21
<212> TYPE: DNA
<213> ORGANISM: Artificial sequence
<220> FEATURE:
<223> OTHER INFORMATION: Primer sequence (IUPAC standard nomenclature)

<400> SEQUENCE: 25
ttacctactc ttcttctgct c                                             21

<210> SEQ ID NO 26
<211> LENGTH: 26
<212> TYPE: DNA
<213> ORGANISM: Artificial sequence
<220> FEATURE:
<223> OTHER INFORMATION: Primer sequence (IUPAC standard nomenclature)

<400> SEQUENCE: 26
tcattcctcc tttggcatat atttag                                        26

<210> SEQ ID NO 27
<211> LENGTH: 20
<212> TYPE: DNA
<213> ORGANISM: Artificial sequence
<220> FEATURE:
<223> OTHER INFORMATION: Primer sequence (IUPAC standard nomenclature)

<400> SEQUENCE: 27
atggccacca cggatgcatc                                               20

<210> SEQ ID NO 28
<211> LENGTH: 21
<212> TYPE: DNA
<213> ORGANISM: Artificial sequence
<220> FEATURE:
```

```
<223> OTHER INFORMATION: Primer sequence (IUPAC standard nomenclature)

<400> SEQUENCE: 28
ttaatccgaa tccttgtcaa c                                              21

<210> SEQ ID NO 29
<211> LENGTH: 20
<212> TYPE: DNA
<213> ORGANISM: Artificial sequence
<220> FEATURE:
<223> OTHER INFORMATION: Primer sequence (IUPAC standard nomenclature)

<400> SEQUENCE: 29
atggccacta ctaccaccac                                                20

<210> SEQ ID NO 30
<211> LENGTH: 21
<212> TYPE: DNA
<213> ORGANISM: Artificial sequence
<220> FEATURE:
<223> OTHER INFORMATION: Primer sequence (IUPAC standard nomenclature)

<400> SEQUENCE: 30
ttactccgaa tcccgatcaa c                                              21

<210> SEQ ID NO 31
<211> LENGTH: 20
<212> TYPE: DNA
<213> ORGANISM: Artificial sequence
<220> FEATURE:
<223> OTHER INFORMATION: Primer sequence (IUPAC standard nomenclature)

<400> SEQUENCE: 31
atgacatcca ccgctctccc                                                20

<210> SEQ ID NO 32
<211> LENGTH: 21
<212> TYPE: DNA
<213> ORGANISM: Artificial sequence
<220> FEATURE:
<223> OTHER INFORMATION: Primer sequence (IUPAC standard nomenclature)

<400> SEQUENCE: 32
ttaagctcgc cctttgcttt c                                              21

<210> SEQ ID NO 33
<211> LENGTH: 20
<212> TYPE: DNA
<213> ORGANISM: Artificial sequence
<220> FEATURE:
<223> OTHER INFORMATION: Primer sequence (IUPAC standard nomenclature)

<400> SEQUENCE: 33
atgtgtaaat cacagaaaca                                                20

<210> SEQ ID NO 34
<211> LENGTH: 22
<212> TYPE: DNA
<213> ORGANISM: Artificial sequence
<220> FEATURE:
<223> OTHER INFORMATION: Primer sequence (IUPAC standard nomenclature)

<400> SEQUENCE: 34 tcattcctttt gtcttatggc cc                                            22
```

```
<210> SEQ ID NO 35
<211> LENGTH: 20
<212> TYPE: DNA
<213> ORGANISM: Artificial sequence
<220> FEATURE:
<223> OTHER INFORMATION: Primer sequence (IUPAC standard nomenclature)

<400> SEQUENCE: 35
tggtaccccg agagcgcttg                                                   20

<210> SEQ ID NO 36
<211> LENGTH: 23
<212> TYPE: DNA
<213> ORGANISM: Artificial sequence
<220> FEATURE:
<223> OTHER INFORMATION: Primer sequence (IUPAC standard nomenclature)

<400> SEQUENCE: 36
ttacgtggtc atctccggtg aac                                               23

<210> SEQ ID NO 37
<211> LENGTH: 1371
<212> TYPE: DNA
<213> ORGANISM: Ostreococcus tauri

<400> SEQUENCE: 37
atgtgtgttg agaccgagaa caacgatgga atccctactg tggagatcgc tttcgatgga       60
gagagagaaa gagctgaggc taacgtgaag ttgtctgctg agaagatgga acctgctgct      120
ttggctaaga ccttcgctag aagatacgtg gttatcgagg agttgagtac gatgtgacc       180 gatttcaaac atcctggagg aaccgtgatt ttctacgctc tctctaacac tggagctgat      240
gctactgagg ctttcaagga gttccaccac agatctagaa aggctaggaa ggctttggct      300
gctttgcctt ctagacctgc taagaccgct aaagtggatg atgctgagat gctccaggat      360
ttcgctaagt ggagaaagga gttggagagg gacggattct tcaagccttc tcctgctcat      420
gttgcttaca gattcgctga gttggctgct atgtacgctt gggaaccta cttgatgtac       480 gctagatacg ttgtgtcctc tgtgttggtt tacgcttgct tcttcggagc tagatgtgga      540
tgggttcaac acgagggagg acactcttct ttgaccggaa acatctggtg gataagaga       600 atccaagctt tcactgctgg attcggattg gctggatctg agatatgtg aactccatg        660 cacaacaagc accacgctac tcctcaaaaa gtgaggcacg atatggattt ggataccact      720
cctgctgttg cttttcttcaa caccgctgtg gaggataata gacctagggg attctctaag    780
tactggctca gattgcaagc ttggaccttc attcctgtga cttctggatt ggtgttgctc      840
ttctggatgt tcttcctcca cccttctaag gctttgaagg aggaaagta cgaggagctt       900 gtgtggatgt tggctgctca cgtgattaga acctggacca ttaaggctgt tactggattc      960
accgctatgc aatcctacgg actcttcttg gctacttctt gggtttccgg atgctacttg     1020
ttcgctcact tctctacttc tcacacccac ttggatgttg ttcctgctga tgagcacttg     1080
tcttgggtta ggtacgctgt ggatcacacc attgatatcg atccttctca gggatgggtt     1140
aactggttga tgggatactt gaactgccaa gtgattcacc acctcttccc ttctatgcct     1200
caattcagac aacctgaggt gtccagaaga ttcgttgctt cgctaagaa gtggaaccct      1260 aactacaagg tgatgactta tgctggagct tggaaggcta ctttgggaaa cctcgataat    1320
gtgggaaagc actactacgt gcacggacaa cactctggaa agaccgcttg a             1371

<210> SEQ ID NO 38
```

<211> LENGTH: 456
<212> TYPE: PRT
<213> ORGANISM: Ostreococcus tauri

<400> SEQUENCE: 38

```
Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
        275                 280                 285

Ser Lys Ala Leu Lys Gly Gly Lys Tyr Glu Glu Leu Val Trp Met Leu
    290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
            340                 345                 350

Val Val Pro Ala Asp Glu His Leu Ser Trp Val Arg Tyr Ala Val Asp
        355                 360                 365

His Thr Ile Asp Ile Asp Pro Ser Gln Gly Trp Val Asn Trp Leu Met
    370                 375                 380

Gly Tyr Leu Asn Cys Gln Val Ile His His Leu Phe Pro Ser Met Pro
```

```
                385                 390                 395                 400
Gln Phe Arg Gln Pro Glu Val Ser Arg Arg Phe Val Ala Phe Ala Lys
                    405                 410                 415

Lys Trp Asn Leu Asn Tyr Lys Val Met Thr Tyr Ala Gly Ala Trp Lys
                420                 425                 430

Ala Thr Leu Gly Asn Leu Asp Asn Val Gly Lys His Tyr Tyr Val His
                    435                 440                 445

Gly Gln His Ser Gly Lys Thr Ala
        450                 455

<210> SEQ ID NO 39
<211> LENGTH: 819
<212> TYPE: DNA
<213> ORGANISM: Thalassiosira pseudonana

<400> SEQUENCE: 39
atggatgctt ataacgctgc tatggataag attggagctg ctatcatcga ttggagtgat      60
ccagatggaa agttcagagc tgatagggag gattggtggt tgtgcgattt cagatccgct     120
atcaccattg ctctcatcta catcgctttc gtgatcttgg gatctgctgt gatgcaatct     180
ctcccagcta tggacccata ccctatcaag ttcctctaca cgtgtctca aatcttcctc      240 tgcgcttaca tgactgttga ggctggattc ctcgcttata ggaacggata caccgttatg     300
ccatgcaacc acttcaacgt gaacgatcca ccagttgcta cttgctctg ctcttctac       360 atctccaaag tgtgggattt ctgggatacc atcttcattg tgctcggaaa gaagtggaga     420
caactctctt tcttgcacgt gtaccaccac accaccatct cctcttcta ctggttgaac      480 gctaacgtgc tctacgatgg agatatcttc ttgaccatcc cctcaacgg attcattcac      540 accgtgatgt acacctacta cttcatctgc atgcacacca aggattctaa gaccggaaag     600
tctttgccaa tctggtggaa gtcatctttg accgctttcc aactcttgca attcaccatc     660
atgatgtccc aagctaccta cttggttttc cacggatgcg ataaggtttc cctcagaatc     720
accatcgtgt acttcgtgta cattctctcc cttttcttcc tcttcgctca gttcttcgtg     780
caatcctaca tggctccaaa gaagaagaag tccgcttga                            819

<210> SEQ ID NO 40
<211> LENGTH: 272
<212> TYPE: PRT
<213> ORGANISM: Thalassiosira pseudonana

<400> SEQUENCE: 40

Met Asp Ala Tyr Asn Ala Ala Met Asp Lys Ile Gly Ala Ala Ile Ile
1               5                   10                  15

Asp Trp Ser Asp Pro Asp Gly Lys Phe Arg Ala Asp Arg Glu Asp Trp
                20                  25                  30

Trp Leu Cys Asp Phe Arg Ser Ala Ile Thr Ile Ala Leu Ile Tyr Ile
            35                  40                  45

Ala Phe Val Ile Leu Gly Ser Ala Val Met Gln Ser Leu Pro Ala Met
        50                  55                  60

Asp Pro Tyr Pro Ile Lys Phe Leu Tyr Asn Val Ser Gln Ile Phe Leu
65                  70                  75                  80

Cys Ala Tyr Met Thr Val Glu Ala Gly Phe Leu Ala Tyr Arg Asn Gly
                85                  90                  95

Tyr Thr Val Met Pro Cys Asn His Phe Asn Val Asn Asp Pro Pro Val
                100                 105                 110
```

Ala Asn Leu Leu Trp Leu Phe Tyr Ile Ser Lys Val Trp Asp Phe Trp
            115                 120                 125

Asp Thr Ile Phe Ile Val Leu Gly Lys Lys Trp Arg Gln Leu Ser Phe
        130                 135                 140

Leu His Val Tyr His His Thr Thr Ile Phe Leu Phe Tyr Trp Leu Asn
145                 150                 155                 160

Ala Asn Val Leu Tyr Asp Gly Asp Ile Phe Leu Thr Ile Leu Leu Asn
                165                 170                 175

Gly Phe Ile His Thr Val Met Tyr Thr Tyr Tyr Phe Ile Cys Met His
            180                 185                 190

Thr Lys Asp Ser Lys Thr Gly Lys Ser Leu Pro Ile Trp Trp Lys Ser
        195                 200                 205

Ser Leu Thr Ala Phe Gln Leu Leu Gln Phe Thr Ile Met Met Ser Gln
    210                 215                 220

Ala Thr Tyr Leu Val Phe His Gly Cys Asp Lys Val Ser Leu Arg Ile
225                 230                 235                 240

Thr Ile Val Tyr Phe Val Tyr Ile Leu Ser Leu Phe Leu Phe Leu Ala
                245                 250                 255

Gln Phe Phe Val Gln Ser Tyr Met Ala Pro Lys Lys Lys Lys Ser Ala
            260                 265                 270

<210> SEQ ID NO 41
<211> LENGTH: 1086
<212> TYPE: DNA
<213> ORGANISM: Phytophtora infestans

<400> SEQUENCE: 41
atggcgacga aggaggcgta tgtgttcccc actctgacgg agatcaagcg gtcgctacct      60
aaagactgtt tcgaggcttc ggtgcctctg tcgctctact acaccgtgcg ttgtctggtg     120
atcgcggtgg ctctaacctt cggtctcaac tacgctcgcg ctctgcccga ggtcgagagc     180
ttctgggctc tggacgccgc actctgcacg ggctacatct gctgcagggc atcgtgttc     240 tggggcttct tcacggtggg ccacgatgcc ggccacggcg ccttctcgcg ctaccacctg     300
cttaacttcg tggtgggcac tttcatgcac tcgctcatcc tcacgccctt cgagtcgtgg     360
aagctcacgc accgtcacca ccacaagaac acgggcaaca ttgaccgtga cgaggtcttc     420
tacccgcaac gcaaggccga cgaccacccg ctgtctcgca acctgattct ggcgctcggg     480
gcagcgtggc tcgcctattt ggtcgagggc ttccctcctc gtaaggtcaa ccacttcaac     540
ccgttcgagc tctgttcgt gcgtcaggtg tcagctgtgg taatctctct tctcgcccac     600
ttcttcgtgg ccggactctc catctatctg agcctccagc tgggccttaa gacgatggca     660
atctactact atggacctgt ttttgtgttc ggcagcatgc tggtcattac caccttccta     720
caccacaatg atgaggagac cccatggtac gccgactcgg agtggacgta cgtcaagggc     780
aacctctcgt ccgtggaccg atcgtacggc gcgctcattg caacctgag ccacaacatc     840 ggcacgcacc agatccacca cctttccct atcattccgc actacaaact caagaaagcc     900
actgcggcct tccaccaggc tttccctgag ctcgtgcgca agagcgacga gccaattatc     960 aaggcttct tccgggttgg acgtctctac gcaaactacg gcgttgtgga ccaggaggcg    1020
aagctcttca cgctaaagga agccaaggcg gcgaccgagg cggcggccaa gaccaagtcc    1080
acgtaa                                                              1086

<210> SEQ ID NO 42
<211> LENGTH: 361

<212> TYPE: PRT
<213> ORGANISM: Phytophtora infestans

<400> SEQUENCE: 42

Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Val Phe Tyr Pro Gln Arg
130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
        355                 360

<210> SEQ ID NO 43
<211> LENGTH: 1560
<212> TYPE: DNA
<213> ORGANISM: Thraustochytrium ssp.

<400> SEQUENCE: 43

```
atgactgttg gatacgacga ggagatccca ttcgagcaag ttagggctca taacaagcca        60
gacgacgctt ggtgtgctat tcacggacac gtgtacgacg ttaccaagtt cgcttcagtt       120
cacccaggag agatattat cttgctcgct gctggaaagg aagctactgt cctctacgag        180
acctaccatg ttagaggagt gtctgacgct gtgctcagaa agtacagaat aggaaagttg       240
ccagacggac aaggaggagc taacgagaag gagaagagaa ccttgtctgg attgtcctct       300
gcttcttact acacctggaa ctccgatttc tacagagtga tgagggagag agttgtggct       360
agattgaagg agagaggaaa ggctagaaga ggaggatacg aactctggat caaggctttc       420
ttgctccttg ttggattctg gtcctctctt tactggatgt gcaccctcga tccatctttc       480
ggagctatct ggctgctat gtcttttggga gtgttcgctg cttttgttgg aacctgcatc       540
caacacgatg aaaccacgg agctttcgct caatctagat gggttaacaa ggtggcagga       600
tggactttgg atatgatcgg agcttctgga atgacttggg agttccaaca cgtgttggga       660
caccacccat acactaactt gatcgaggag gagaacggat gcaaaaggt gtccggaaag        720
aagatggata ccaagttggc tgatcaagag tctgatccag atgtgttctc cacctaccca       780
atgatgagat tgcaccttg caccagaag aggtggtatc acaggttcca gcacatctac        840
ggaccttca tcttcggatt catgaccatc aacaaggtgg tgactcaaga tgttggagtg       900
gtgttgagaa agagactctt ccaaatcgat gctgagtgca gatatgcttc cccaatgtac      960
gttgctaggt tctggattat gaaggctttg accgtgttgt atatggttgc tttgccttgt     1020
tatatgcaag gaccttggca cggattgaaa ctcttcgcta tcgctcactt cacttgcgga     1080
gaggttttgg ctaccatgtt catcgtgaac acacattatcg agggagtgtc ttacgcttct    1140
aaggatgctg ttaagggaac tatggctcca ccaaagacta tgcacggagt gaccccaatg     1200
aacaacacta gaaaggaggt tgaggctgag gcttctaagt ctggagctgt ggttaagtct      1260
gtgccattgg atgattgggc tgctgttcag tgccaaacct ctgtgaactg gtctgttgga    1320
tcttggtttt ggaaccactt ctctggagga ctcaaccacc aaatcgagca ccacctcttc     1380
ccaggattgt ctcacgagac ctactaccac atccaagacg tggttcaatc tacctgtgct    1440
gagtacggag ttccatacca acacgagcca tctttgtgga ctgcttactg aagatgctc     1500
gaacaccta gacaattggg aaacgaggag actcacgagt catggcagag agctgcttga     1560
```

<210> SEQ ID NO 44
<211> LENGTH: 519
<212> TYPE: PRT
<213> ORGANISM: Thraustochytrium ssp.

<400> SEQUENCE: 44

```
Met Thr Val Gly Tyr Asp Glu Glu Ile Pro Phe Glu Gln Val Arg Ala
1               5                   10                  15

His Asn Lys Pro Asp Asp Ala Trp Cys Ala Ile His Gly His Val Tyr
            20                  25                  30

Asp Val Thr Lys Phe Ala Ser Val His Pro Gly Gly Asp Ile Ile Leu
        35                  40                  45

Leu Ala Ala Gly Lys Glu Ala Thr Val Leu Tyr Glu Thr Tyr His Val
    50                  55                  60

Arg Gly Val Ser Asp Ala Val Leu Arg Lys Tyr Arg Ile Gly Lys Leu
65                  70                  75                  80

Pro Asp Gly Gln Gly Gly Ala Asn Glu Lys Glu Lys Arg Thr Leu Ser
```

```
                     85                  90                  95
Gly Leu Ser Ser Ala Ser Tyr Tyr Thr Trp Asn Ser Asp Phe Tyr Arg
            100                 105                 110

Val Met Arg Glu Arg Val Val Ala Arg Leu Lys Glu Arg Gly Lys Ala
            115                 120                 125

Arg Arg Gly Gly Tyr Glu Leu Trp Ile Lys Ala Phe Leu Leu Leu Val
        130                 135                 140

Gly Phe Trp Ser Ser Leu Tyr Trp Met Cys Thr Leu Asp Pro Ser Phe
145                 150                 155                 160

Gly Ala Ile Leu Ala Ala Met Ser Leu Gly Val Phe Ala Ala Phe Val
                165                 170                 175

Gly Thr Cys Ile Gln His Asp Gly Asn His Gly Ala Phe Ala Gln Ser
            180                 185                 190

Arg Trp Val Asn Lys Val Ala Gly Trp Thr Leu Asp Met Ile Gly Ala
        195                 200                 205

Ser Gly Met Thr Trp Glu Phe Gln His Val Leu Gly His His Pro Tyr
    210                 215                 220

Thr Asn Leu Ile Glu Glu Asn Gly Leu Gln Lys Val Ser Gly Lys
225                 230                 235                 240

Lys Met Asp Thr Lys Leu Ala Asp Gln Glu Ser Asp Pro Asp Val Phe
                245                 250                 255

Ser Thr Tyr Pro Met Met Arg Leu His Pro Trp His Gln Lys Arg Trp
            260                 265                 270

Tyr His Arg Phe Gln His Ile Tyr Gly Pro Phe Ile Phe Gly Phe Met
        275                 280                 285

Thr Ile Asn Lys Val Val Thr Gln Asp Val Gly Val Val Leu Arg Lys
    290                 295                 300

Arg Leu Phe Gln Ile Asp Ala Glu Cys Arg Tyr Ala Ser Pro Met Tyr
305                 310                 315                 320

Val Ala Arg Phe Trp Ile Met Lys Ala Leu Thr Val Leu Tyr Met Val
                325                 330                 335

Ala Leu Pro Cys Tyr Met Gln Gly Pro Trp His Gly Leu Lys Leu Phe
            340                 345                 350

Ala Ile Ala His Phe Thr Cys Gly Glu Val Leu Ala Thr Met Phe Ile
        355                 360                 365

Val Asn His Ile Ile Glu Gly Val Ser Tyr Ala Ser Lys Asp Ala Val
    370                 375                 380

Lys Gly Thr Met Ala Pro Pro Lys Thr Met His Gly Val Thr Pro Met
385                 390                 395                 400

Asn Asn Thr Arg Lys Glu Val Glu Ala Glu Ser Lys Ser Gly Ala
                405                 410                 415

Val Val Lys Ser Val Pro Leu Asp Asp Trp Ala Ala Val Gln Cys Gln
            420                 425                 430

Thr Ser Val Asn Trp Ser Val Gly Ser Trp Phe Trp Asn His Phe Ser
        435                 440                 445

Gly Gly Leu Asn His Gln Ile Glu His His Leu Phe Pro Gly Leu Ser
    450                 455                 460

His Glu Thr Tyr Tyr His Ile Gln Asp Val Val Gln Ser Thr Cys Ala
465                 470                 475                 480

Glu Tyr Gly Val Pro Tyr Gln His Glu Pro Ser Leu Trp Thr Ala Tyr
                485                 490                 495

Trp Lys Met Leu Glu His Leu Arg Gln Leu Gly Asn Glu Glu Thr His
            500                 505                 510
```

Glu Ser Trp Gln Arg Ala Ala
        515

<210> SEQ ID NO 45
<211> LENGTH: 1179
<212> TYPE: DNA
<213> ORGANISM: Sphaeroforma arctica

<400> SEQUENCE: 45

```
atgccaccca atgcgttaaa agagcgtgct atagacacca cctgcgagta tgaagaagat      60
cacactatta ccagcaacca gcagatcgat tatttaaagg ctcaacaaaa aaagttacca     120
actgacctag tcgaggtctg ccggcacctc cctaaagata tcttccaaat taggccattc     180
agagcgtatc ttgctgcctt tcaggctgta ggaatgacag ctttgtcgtt gtaccttttg     240
acattttgtc actcttggtg gtccctctgc attggctggg cttttgccgg tacttgtgct     300
actggaatgt ttatcatcgg acatgaatgc gcacatggtg ctttcagcaa atcatcactg     360
gagaacgcat tcgttggaac aatagtgatg gcgccactcg gatggacata tcatggttgg     420
aggataacac acaaccacca ccacgcatat cgaaccagaa taaacaagga ccacttgtgg     480
agtcccttgg accacgaaat ggttgcaaat acatcaaatg ccgtgttgaa agtactcgag     540
tattttatg ttgggcctct gttcttcgag agtagtattt tgcaccattt tgcaaatctg     600
aatatcttca tattcccaaa aaggcactgg aagaacctaa tttcgagtaa tttattcgct     660
ttggctgcta cattaggttt atggtaccac ttctactata atcttgacaa tggcgacagt     720
ggctggtggg ccgtgttcaa gtattggggt gcaccatatc tttgcttcaa tttttggctg     780
tccacacata cgtatttcca ccacaagtcg agggatattg ctggattga aaagcgaat      840
tggaataaag cacaagccca gcttttccat acagcccacg tggactatca ccccatagtc     900
gaaatgctac acttcgacat caattggcat gtgcctcacc atgtgtcgac acgaattcca     960
tggtacaatt tcgacgtgc gactttcgca cttattaagg catatggtga caagatccat    1020
acctacgaga tgagccccac gtactggatg gaagtgactt ctgaatgcca cgtgcatgat    1080
gacgtgtcta aatatgtgag tgtgggagag tcaaaggaac gctcggaacg tgagaaacaa    1140
atagctagca tggaagctag gaaaacaaaa acaaattag                           1179
```

<210> SEQ ID NO 46
<211> LENGTH: 392
<212> TYPE: PRT
<213> ORGANISM: Sphaeroforma arctica

<400> SEQUENCE: 46

Met Pro Pro Asn Ala Leu Lys Glu Arg Ala Ile Asp Thr Thr Cys Glu
1               5                   10                  15

Tyr Glu Glu Asp His Thr Ile Thr Ser Asn Gln Gln Ile Asp Tyr Leu
            20                  25                  30

Lys Ala Gln Gln Lys Lys Leu Pro Thr Asp Leu Val Glu Val Cys Arg
        35                  40                  45

His Leu Pro Lys Asp Ile Phe Gln Ile Arg Pro Phe Arg Ala Tyr Leu
    50                  55                  60

Ala Ala Phe Gln Ala Val Gly Met Thr Ala Leu Ser Leu Tyr Leu Leu
65                  70                  75                  80

Thr Phe Cys His Ser Trp Trp Ser Leu Cys Ile Gly Trp Ala Phe Ala
                85                  90                  95

Gly Thr Cys Ala Thr Gly Met Phe Ile Ile Gly His Glu Cys Ala His

```
            100                 105                  110
Gly Ala Phe Ser Lys Ser Leu Glu Asn Ala Phe Val Gly Thr Ile
        115                 120                 125
Val Met Ala Pro Leu Gly Trp Thr Tyr His Gly Trp Arg Ile Thr His
    130                 135                 140
Asn His His Ala Tyr Thr Asn Gln Ile Asn Lys Asp His Leu Trp
145                 150                 155                 160
Ser Pro Leu Asp His Glu Met Val Ala Asn Thr Ser Asn Ala Val Leu
                165                 170                 175
Lys Val Leu Glu Tyr Phe Tyr Val Gly Pro Leu Phe Phe Glu Ser Ser
            180                 185                 190
Ile Leu His His Phe Ala Asn Leu Asn Ile Phe Ile Phe Pro Lys Arg
        195                 200                 205
His Trp Lys Asn Leu Ile Ser Ser Asn Leu Phe Ala Leu Ala Ala Thr
    210                 215                 220
Leu Gly Leu Trp Tyr His Phe Tyr Tyr Asn Leu Asp Asn Gly Asp Ser
225                 230                 235                 240
Gly Trp Trp Ala Val Phe Lys Tyr Trp Gly Ala Pro Tyr Leu Cys Phe
                245                 250                 255
Asn Phe Trp Leu Ser Thr His Thr Tyr Phe His His Lys Ser Arg Asp
            260                 265                 270
Ile Gly Trp Ile Glu Lys Ala Asn Trp Asn Lys Ala Gln Ala Gln Leu
        275                 280                 285
Phe His Thr Ala His Val Asp Tyr His Pro Ile Val Glu Met Leu His
    290                 295                 300
Phe Asp Ile Asn Trp His Val Pro His His Val Ser Thr Arg Ile Pro
305                 310                 315                 320
Trp Tyr Asn Leu Arg Arg Ala Thr Phe Ala Leu Ile Lys Ala Tyr Gly
                325                 330                 335
Asp Lys Ile His Thr Tyr Glu Met Ser Pro Thr Tyr Trp Met Glu Val
            340                 345                 350
Thr Ser Glu Cys His Val His Asp Asp Val Ser Lys Tyr Val Ser Val
        355                 360                 365
Gly Glu Ser Lys Glu Arg Ser Glu Arg Glu Lys Gln Ile Ala Ser Met
    370                 375                 380
Glu Ala Arg Lys Thr Lys Thr Asn
385                 390

<210> SEQ ID NO 47
<211> LENGTH: 25
<212> TYPE: DNA
<213> ORGANISM: Artificial sequence
<220> FEATURE:
<223> OTHER INFORMATION: Primer

<400> SEQUENCE: 47
atgccaccca atgcgttaaa agagc                                           25

<210> SEQ ID NO 48
<211> LENGTH: 32
<212> TYPE: DNA
<213> ORGANISM: Artificial sequence
<220> FEATURE:
<223> OTHER INFORMATION: Primer

<400> SEQUENCE: 48
ctaatttgtt tttgttttcc tagcttccat gc                                   32
```

<210> SEQ ID NO 49
<211> LENGTH: 1446
<212> TYPE: DNA
<213> ORGANISM: Verticullium dahliae

<400> SEQUENCE: 49
atggctgcga ccacatcctc gttgccggcc aaggccaacc ctcagcttcg ccgcaccgcc 60
aattctaccg aggctgatct ctcctccccc tctactgcag tggcttcgcc caacgactcg 120
ccccgaccct cagcttcgtc gacttcgctg tcttcgctct cctccatcga tgcttctggc 180
gagaaaccca actacggcgt cctcctcgac acgtacggca acgagttcac cccgcccgac 240
tttaccatca aggacatccg cgatgccatc cccaagcact gcttcgagcg ctctgcgctc 300
aggggctacg gctacatcgc ccgtgacatg gttctcctcg ccaccacgtt caccgtctgg 360
cacaactttg tgacgccgca tcacattccc tcgtaccctc tccgtgtcgc tctttgggcc 420
gtgtacactg ttctccaggg tcttttcgcc accggtctct gggtcattgc ccacgagtgc 480
ggccacggcg ccttctccga ttcaactcgc gtcaacaacg tcaccggctg gttcctccat 540
tccgcactcc ttgtgcccta ctacagctgg caaatgtccc acagcaagca ccacaaggcc 600
accggcaaca tggagcgcga catggtcttc gtgccccgca ctcgtgagga gcacgccacc 660
cgcctcggca ccatggccca cgagcttgct gagctgactg aagagactcc tatcgccacc 720
ctgcttcacc tcgtcggcca gcagctcgtc ggctggccca gttacctcat caacaacgtt 780
accggccaca actaccacga gcgtcaccgc gagggccgtg gcaagggcaa gcgcaacggt 840
ttcggcggcg gcgtcaacca ctttgatccc cgcagccccc tgtttgagaa ccgcgatgct 900
tggagggtca tcatgtctga tgtcggtctt gctcttgcct ttgccggcct cttctacctc 960
ggcaacacct ttggctggaa gaacttggct gtctggtact tcatccccta cttgtgggtg 1020
aaccactggc ttgttgccat tactttcctt cagcacaccg acccctcgct tccccactac 1080
accggtgagc agtggaattt cgtccgcggt gctgccgcta ccattgaccg agagatgggc 1140
tttgtcggtc gccacctgct ccacggcatt gttgagacgc acgtccttca ccactacatc 1200
agctccatcc ccttctacaa tgccgacgag gccaccgagg ccatcaagcc cgtcatgggc 1260
aagcactacc gtgctgatgt ccgcgacggt ccctggggct tcatccgctc gctttggacc 1320
tcagcacgct cgtgccagtg ggttgagccc agcgtgggtg ctgagggtgc cggcaagggc 1380
atcctgttct tccgcaaccg caaccacatt ggtgtgccgc ccatgggccg tacggatgag 1440
cagtag 1446

<210> SEQ ID NO 50
<211> LENGTH: 481
<212> TYPE: PRT
<213> ORGANISM: Verticullium dahliae

<400> SEQUENCE: 50

Met Ala Ala Thr Thr Ser Ser Leu Pro Ala Lys Ala Asn Pro Gln Leu
1 5 10 15

Arg Arg Thr Ala Asn Ser Thr Glu Ala Asp Leu Ser Ser Pro Ser Thr
20 25 30

Ala Val Ala Ser Pro Asn Asp Ser Pro Arg Pro Ser Ala Ser Ser Thr
35 40 45

Ser Leu Ser Ser Leu Ser Ser Ile Asp Ala Ser Gly Glu Lys Pro Asn
50 55 60

```
Tyr Gly Val Leu Leu Asp Thr Tyr Gly Asn Glu Phe Thr Pro Pro Asp
 65                  70                  75                  80

Phe Thr Ile Lys Asp Ile Arg Asp Ala Ile Pro Lys His Cys Phe Glu
                 85                  90                  95

Arg Ser Ala Leu Arg Gly Tyr Gly Tyr Ile Ala Arg Asp Met Val Leu
            100                 105                 110

Leu Ala Thr Thr Phe Thr Val Trp His Asn Phe Val Thr Pro His His
        115                 120                 125

Ile Pro Ser Tyr Pro Leu Arg Val Ala Leu Trp Ala Val Tyr Thr Val
    130                 135                 140

Leu Gln Gly Leu Phe Ala Thr Gly Leu Trp Val Ile Ala His Glu Cys
145                 150                 155                 160

Gly His Gly Ala Phe Ser Asp Ser Thr Arg Val Asn Asn Val Thr Gly
                165                 170                 175

Trp Phe Leu His Ser Ala Leu Leu Val Pro Tyr Tyr Ser Trp Gln Met
                180                 185                 190

Ser His Ser Lys His His Lys Ala Thr Gly Asn Met Glu Arg Asp Met
            195                 200                 205

Val Phe Val Pro Arg Thr Arg Glu Glu His Ala Thr Arg Leu Gly Thr
210                 215                 220

Met Ala His Glu Leu Ala Glu Leu Thr Glu Glu Thr Pro Ile Ala Thr
225                 230                 235                 240

Leu Leu His Leu Val Gly Gln Gln Leu Gly Trp Pro Ser Tyr Leu
                245                 250                 255

Ile Asn Asn Val Thr Gly His Asn Tyr His Glu Arg His Arg Glu Gly
            260                 265                 270

Arg Gly Lys Gly Lys Arg Asn Gly Phe Gly Gly Val Asn His Phe
        275                 280                 285

Asp Pro Arg Ser Pro Leu Phe Glu Asn Arg Asp Ala Trp Arg Val Ile
    290                 295                 300

Met Ser Asp Val Gly Leu Ala Leu Ala Phe Ala Gly Leu Phe Tyr Leu
305                 310                 315                 320

Gly Asn Thr Phe Gly Trp Lys Asn Leu Ala Val Trp Tyr Phe Ile Pro
                325                 330                 335

Tyr Leu Trp Val Asn His Trp Leu Val Ala Ile Thr Phe Leu Gln His
            340                 345                 350

Thr Asp Pro Ser Leu Pro His Tyr Thr Gly Glu Gln Trp Asn Phe Val
        355                 360                 365

Arg Gly Ala Ala Ala Thr Ile Asp Arg Glu Met Gly Phe Val Gly Arg
    370                 375                 380

His Leu Leu His Gly Ile Val Glu Thr His Val Leu His His Tyr Ile
385                 390                 395                 400

Ser Ser Ile Pro Phe Tyr Asn Ala Asp Glu Ala Thr Glu Ala Ile Lys
                405                 410                 415

Pro Val Met Gly Lys His Tyr Arg Ala Asp Val Arg Asp Gly Pro Trp
            420                 425                 430

Gly Phe Ile Arg Ser Leu Trp Thr Ser Ala Arg Ser Cys Gln Trp Val
        435                 440                 445

Glu Pro Ser Val Gly Ala Glu Gly Ala Gly Lys Gly Ile Leu Phe Phe
    450                 455                 460

Arg Asn Arg Asn His Ile Gly Val Pro Pro Met Gly Arg Thr Asp Glu
465                 470                 475                 480

Gln
```

<210> SEQ ID NO 51
<211> LENGTH: 26
<212> TYPE: DNA
<213> ORGANISM: Artificial sequence
<220> FEATURE:
<223> OTHER INFORMATION: Primer

<400> SEQUENCE: 51
atggctgcga ccacatcctc gttgcc                                          26

<210> SEQ ID NO 52
<211> LENGTH: 31
<212> TYPE: DNA
<213> ORGANISM: Artificial sequence
<220> FEATURE:
<223> OTHER INFORMATION: Primer

<400> SEQUENCE: 52
ctactgctca tccgtacggc ccatgggcgg c                                    31

<210> SEQ ID NO 53
<211> LENGTH: 24
<212> TYPE: DNA
<213> ORGANISM: Artificial sequence
<220> FEATURE:
<223> OTHER INFORMATION: Primer sequence (IUPAC standard nomenclature)
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is inosine
<220> FEATURE:
<221> NAME/KEY: misc_feature
<222> LOCATION: (21)..(21)
<223> OTHER INFORMATION: n is inosine

<400> SEQUENCE: 53
acnggnbtnt ggrtnbtngs ncay                                            24

<210> SEQ ID NO 54
<211> LENGTH: 21
<212> TYPE: DNA
<213> ORGANISM: Artificial sequence
<220> FEATURE:
<223> OTHER INFORMATION: Primer sequence (IUPAC standard nomenclature)
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)

```
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (21)..(21)
<223> OTHER INFORMATION: n is inosine

<400> SEQUENCE: 54
sangarytnk bnggntggsm n                                          21

<210> SEQ ID NO 55
<211> LENGTH: 21
<212> TYPE: DNA
<213> ORGANISM: Artificial sequence
<220> FEATURE:
<223> OTHER INFORMATION: Primer sequence (IUPAC standard nomenclature)
<220> FEATURE:
<221> NAME/KEY: misc_feature
<222> LOCATION: (1)..(1)
<223> OTHER INFORMATION: n is inosine
<220> FEATURE:
<221> NAME/KEY: misc_feature
<222> LOCATION: (7)..(7)
<223> OTHER INFORMATION: n is inosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (13)..(13)
<223> OTHER INFORMATION: n is inosine

<400> SEQUENCE: 55
ngtdatnrvn acnarccart g                                          21

<210> SEQ ID NO 56
<211> LENGTH: 21
<212> TYPE: DNA
<213> ORGANISM: Artificial sequence
<220> FEATURE:
<223> OTHER INFORMATION: Primer sequence (IUPAC standard nomenclature)
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (7)..(7)
<223> OTHER INFORMATION: n is inosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (16)..(16)
<223> OTHER INFORMATION: n is inosine

<400> SEQUENCE: 56
rtgndwnysn aydatnccrt g                                          21
```

FATTY ACID DESATURASE AND USES THEREOF

RELATED APPLICATIONS

This application is a national stage application (under 35 U.S.C. §371) of PCT/EP2010/067969, filed Nov. 23, 2010, which claims benefit of U.S. Provisional Application 61/263, 838, filed Nov. 24, 2009, and European application 09176869.7, filed Nov. 24, 2009.

The Sequence Listing associated with this application is filed in electronic format via EFS-Web and hereby incorporated by reference into the specification in its entirety. The name of the text file containing the Sequence Listing is Sequence_Listing_13987_00186. The size of the text file is 82 KB, and the text file was created on Apr. 11, 2013.

The invention in principle pertains to the field of recombinant manufacture of fatty acids. It provides nucleic acid molecules which encode novel fatty acid desaturase. The invention also provides recombinant expression vectors containing desaturase and also elongase nucleic acid molecules, host cells into which the expression vectors have been introduced, and methods for large-scale production of long chain polyunsaturated fatty acids (LCPUFAs), e.g. ARA, EPA and DHA.

Fatty acids are carboxylic acids with long-chain hydrocarbon side groups that play a fundamental role in many biological processes. Fatty acids are rarely found free in nature but, rather, occur in esterified form as the major component of lipids. As such, lipids/fatty acids are sources of energy (e.g., beta-oxidation). In addition, lipids/fatty acids are an integral part of cell membranes and, therefore, are indispensable for processing biological or biochemical information.

Fatty acids can be divided into two groups: saturated fatty acids formed of single carbon bonds and the unsaturated fatty acids which contain one or more carbon double bonds in cis-configuration. Unsaturated fatty acids are produced by terminal desaturases that belong to the class of nonheme-iron enzymes. Each of these enzymes are part of an electron-transport system that contains two other proteins, namely cytochrome $b_5$ and NADH-cytochrome $b_5$ reductase. Specifically, such enzymes catalyze the formation of double bonds between the carbon atoms of a fatty acid molecule, for example, by catalyzing the oxygen-dependent dehydrogenation of fatty acids (Sperling et al., 2003). Human and other mammals have a limited spectrum of desaturases that are required for the formation of particular double bonds in unsaturated fatty acids and thus, have a limited capacity for synthesizing essential fatty acids, e.g., long chain polyunsaturated fatty acids (LCPUFAs). Thus, humans have to take up some fatty acids through their diet. Such essential fatty acids include, for example, linoleic acid (C18:2), linolenic acid (C18:3). In contrast, insects, microorganisms and plants are able to synthesize a much larger variety of unsaturated fatty acids and their derivatives. Indeed, the biosynthesis of fatty acids is a major activity of plants and microorganisms.

Long chain polyunsaturated fatty acids (LCPUFAs) such as docosahexaenoic acid (DHA, 22:6(4,7,10,13,16,19)) are essential components of cell membranes of various tissues and organelles in mammals (nerve, retina, brain and immune cells). For example, over 30% of fatty acids in brain phospholipid are 22:6 (n-3) and 20:4 (n-6) (Crawford, M. A., et al., (1997) Am. J. Clin. Nutr. 66:1032 S-1041S). In retina, DHA accounts for more than 60% of the total fatty acids in the rod outer segment, the photosensitive part of the photoreceptor cell (Giusto, N. M., et al. (2000) Prog. Lipid Res. 39:315-391). Clinical studies have shown that DHA is essential for the growth and development of the brain in infants, and for maintenance of normal brain function in adults (Martinetz, M. (1992) J. Pediatr. 120:S129-S138). DHA also has significant effects on photoreceptor function involved in the signal transduction process, rhodopsin activation, and rod and cone development (Giusto, N. M., et al. (2000) Prog. Lipid Res. 39:315-391). In addition, some positive effects of DHA were also found on diseases such as hypertension, arthritis, atherosclerosis, depression, thrombosis and cancers (Horrocks, L. A. and Yeo, Y. K. (1999) Pharmacol. Res. 40:211-215). Therefore, appropriate dietary supply of the fatty acid is important for human health. Because such fatty acids cannot be efficiently synthesized by infants, young children and senior citizens, it is particularly important for these individuals to adequately intake these fatty acids from the diet (Spector, A. A. (1999) Lipids 34:S1-S3).

Currently the major sources of DHA are oils from fish and algae. Fish oil is a major and traditional source for this fatty acid, however, it is usually oxidized by the time it is sold. In addition, the supply of fish oil is highly variable, particularly in view of the shrinking fish populations. Moreover, the algal source of oil is expensive due to low yield and the high costs of extraction.

EPA and ARA are both Δ5 essential fatty acids. They form a unique class of food and feed constituents for humans and animals. EPA belongs to the n-3 series with five double bonds in the acyl chain. EPA is found in marine food and is abundant in oily fish from North Atlantic. ARA belongs to the n-6 series with four double bonds. The lack of a double bond in the ω-3 position confers on ARA different properties than those found in EPA. The eicosanoids produced from AA have strong inflammatory and platelet aggregating properties, whereas those derived from EPA have anti-inflammatory and anti-platelet aggregating properties. ARA can be obtained from some foods such as meat, fish and eggs, but the concentration is low.

Gamma-linolenic acid (GLA) is another essential fatty acid found in mammals. GLA is the metabolic intermediate for very long chain n-6 fatty acids and for various active molecules. In mammals, formation of long chain polyunsaturated fatty acids is rate-limited by Δ6 desaturation. Many physiological and pathological conditions such as aging, stress, diabetes, eczema, and some infections have been shown to depress the Δ6 desaturation step. In addition, GLA is readily catabolized from the oxidation and rapid cell division associated with certain disorders, e.g., cancer or inflammation. Therefore, dietary supplementation with GLA can reduce the risks of these disorders. Clinical studies have shown that dietary supplementation with GLA is effective in treating some pathological conditions such as atopic eczema, premenstrual syndrome, diabetes, hypercholesterolemia, and inflammatory and cardiovascular disorders.

A large number of beneficial health effects have been shown for DHA or mixtures of EPA/DHA. DHA is a n-3 very long chain fatty acid with six double bonds.

Although biotechnology offers an attractive route for the production of specialty fatty acids, current techniques fail to provide an efficient means for the large scale production of unsaturated fatty acids. Accordingly, there exists a need for an improved and efficient method of producing unsaturated fatty acids, such as DHA, EPA and ARA.

Thus, the present invention relates to a polynucleotide comprising
a) a nucleotide sequence as shown in SEQ ID NO: 1,
b) a nucleic acid sequence encoding a polypeptide having an amino acid sequence as shown in SEQ ID NO: 2, c) a nucleic acid sequence being at least 70% identical to the nucleic acid sequence of a) or b), wherein said nucleic acid sequence encodes a polypeptide having Δ 15-desaturase activity;
d) a nucleic acid sequence encoding a polypeptide having Δ 15-desaturase activity and having an amino acid sequence which is at least 70% identical to the amino acid sequence of any one of a) to c); and
e) a nucleic acid sequence which is capable of hybridizing under stringent conditions to any one of a) to d), wherein said nucleic acid sequence encodes a polypeptide having Δ 15-desaturase activity.

The term "polynucleotide" as used in accordance with the present invention relates to a polynucleotide comprising a nucleic acid sequence which encodes a polypeptide having desaturase activity. Preferably, the polypeptide encoded by the polynucleotide of the present invention having desaturase activity upon expression in a plant shall be capable of increasing the amount of PUFA and, in particular, LCPUFA in, e.g., seed oils or the entire plant or parts thereof. Such an increase is, preferably, statistically significant when compared to a LCPUFA producing transgenic control plant which expresses the present state of the art set of desaturases and elongases required for LCPUFA synthesis but does not express the polynucleotide of the present invention. Whether an increase is significant can be determined by statistical tests well known in the art including, e.g., Student's t-test. More preferably, the increase is an increase of the amount of triglycerides containing LCPUFA of at least 5%, at least 10%, at least 15%, at least 20% or at least 30% compared to the said control. Preferably, the LCPUFA referred to before is a polyunsaturated fatty acid having a C-20, C-22 or C24 fatty acid body, more preferably, ARA, EPA or DHA. Suitable assays for measuring the activities mentioned before are described in the accompanying Examples.

The term "desaturase" but also the term "elongase" as used herein refers to the activity of a desaturase, introducing a double bond into the carbon chain of a fatty acid, preferably into fatty acids with 18, 20 or 22 carbon molecules, or an elongase, introducing two carbon molecules into the carbon chain of a fatty acid, preferably into fatty acids with 18, 20 or 22 carbon molecules More preferably, polynucleotides having a nucleic acid sequence as shown in SEQ ID NO: 1 encoding polypeptides having amino acid sequences as shown in SEQ ID NOs: 2 or variants thereof, preferably, exhibit desaturase activity, more preferably Δ 15-desaturase activity.

Polynucleotides encoding a polypeptide having desaturase activity obtained in accordance with the present invention, but also polynucleotides encoding a polypeptide having elongase activity as specified above has been preferably from *Limonomyces roseipellis, Sphaeroforma arctica, Laetisaria fuciformis, Thielaviopsis basicola, Verticullium dahliae*. However, orthologs, paralogs or other homologs may be identified from other species. Preferably, they are obtained from plants such as algae, for example *Isochrysis, Mantoniella, Ostreococcus* or *Crypthecodinium*, algae/diatoms such as *Phaeodactylum, Thalassiosira* or *Thraustochytrium*, mosses such as *Physcomitrella* or *Ceratodon*, or higher plants such as the *Primulaceae* such as *Aleuritia, Calendula stellata, Osteospermum spinescens* or *Osteospermum hyoseroides*, microorganisms such as fungi, such as *Aspergillus, Phytophthora, Entomophthora, Mucor* or *Mortierella*, bacteria such as *Shewanella*, yeasts or animals. Preferred animals are nematodes such as *Caenorhabditis*, insects or vertebrates. Among the vertebrates, the nucleic acid molecules may, preferably, be derived from *Euteleostomi, Actinopterygii; Neopterygii; Teleostei; Euteleostei, Protacanthopterygii, Salmoniformes; Salmonidae* or *Oncorhynchus*, more preferably, from the order of the Salmoniformes, most preferably, the family of the Salmonidae, such as the genus *Salmo*, for example from the genera and species *Oncorhynchus mykiss, Trutta trutta* or *Salmo trutta fario*. Moreover, the nucleic acid molecules may be obtained from the diatoms such as the genera *Thallasiosira* or *Phaeodactylum*.

Thus, the term "polynucleotide" as used in accordance with the present invention further encompasses variants of the aforementioned specific polynucleotides representing orthologs, paralogs or other homologs of the polynucleotide of the present invention. Moreover, variants of the polynucleotide of the present invention also include artificially generated muteins. Said muteins include, e.g., enzymes which are generated by mutagenesis techniques and which exhibit improved or altered substrate specificity, or codon optimized polynucleotides. The polynucleotide variants, preferably, comprise a nucleic acid sequence characterized in that the sequence can be derived from the aforementioned specific nucleic acid sequence shown in SEQ ID NO: 1 or by a polynucleotide encoding a polypeptide having an amino acid sequence as shown SEQ ID NO: 2 by at least one nucleotide substitution, addition and/or deletion, whereby the variant nucleic acid sequence shall still encode a polypeptide having a desaturase activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA: DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples. As a template, DNA or cDNA from bacteria, fungi, plants or animals may be used. Further, variants include polynucleotides comprising nucleic acid sequences which are at least 50%, at least 55%, at least 60%, at least 65%, at least 70%, at least 75%, at least 80%, at least 85%, at least 90%, at least 95%, at least 98% or at least 99% identical to the nucleic acid sequences shown in SEQ ID NO: 1 preferably, encoding polypeptides retaining a desaturase activity as specified above. Moreover, also encompassed are polynucleotides which comprise nucleic acid sequences encoding a polypeptide having an amino acid sequences which are at least at least 70%, at least 75%, at least 80%, at least 85%, at least 90%, at least 95%, at least 98% or at least 99% identical to the amino acid sequences shown in any one of SEQ ID NO: 2 wherein the polypeptide, preferably, retains desaturase activity as specified above. The percent identity values are, preferably, calculated over the entire amino acid or nucleic acid sequence region. A series of programs based on a variety of algorithms is available to the skilled worker for comparing different sequences. In a preferred embodiment, the percent identity between two amino acid sequences is determined using the Needleman and Wunsch algorithm (Needleman 1970, J. Mol. Biol. (48):444-453) which has been incorporated into the needle program in the EMBOSS software package (EMBOSS: The European Molecular Biology Open Software Suite, Rice, P., Longden, I., and Bleasby, A, Trends in Genetics 16(6), 276-277, 2000), using either a BLOSUM 45 or PAM250 scoring matrix for distantly related proteins, or either a BLOSUM 62 or PAM160 scoring matrix for closer related proteins, and a gap opening penalty of 16, 14, 12, 10, 8, 6, or 4 and a gap entension penalty of 0.5, 1, 2, 3, 4, 5, or 6. Guides for local installation of the EMBOSS package as well as links to WEB-Services can be found at http://emboss.sourceforge.net. A preferred, non-limiting example of parameters to be used for aligning two amino acid sequences using the needle program are the default parameters, including the EBLOSUM62 scoring matrix, a gap opening penalty of 10 and a gap extension penalty of 0.5. In yet another preferred embodiment, the percent identity between two nucleotide sequences is determined using the needle program in the EMBOSS software package (EMBOSS: The European Molecular Biology Open Software Suite, Rice, P., Longden, I., and Bleasby, A, Trends in Genetics 16(6), 276-277, 2000), using the EDNAFULL scoring matrix and a gap opening penalty of 16, 14, 12, 10, 8, 6, or 4 and a gap extension penalty of 0.5, 1, 2, 3, 4, 5, or 6. A preferred, non-limiting example of parameters to be used in conjunction for aligning two amino acid sequences using the needle program are the default parameters, including the EDNAFULL scoring matrix, a gap opening penalty of 10 and a gap extension penalty of 0.5. The nucleic acid and protein sequences of the present invention can further be used as a "query sequence" to perform a search against public databases to, for example, identify other family members or related sequences. Such searches can be performed using the BLAST series of programs (version 2.2) of Altschul et al. (Altschul 1990, J. Mol. Biol. 215:403-10). BLAST using nucleic acid sequences of the invention as query sequence can be performed with the BLASTn, BLASTx or the tBLASTx program using default parameters to obtain either nucleotide sequences (BLASTn, tBLASTx) or amino acid sequences (BLASTx) homologous to sequences of the invention. BLAST using protein sequences of the invention as query sequence can be performed with the BLASTp or the tBLASTn program using default parameters to obtain either amino acid sequences (BLASTp) or nucleic acid sequences (tBLASTn) homologous to sequences of the invention. To obtain gapped alignments for comparison purposes, Gapped BLAST using default parameters can be utilized as described in Altschul et al. (Altschul 1997, Nucleic Acids Res. 25(17):3389-3402).

TABLE 1

Relation of sequence types of querry and hit sequences for various BLASt programs

| Input query sequence | Converted Query | Algorithm | Converted Hit | Actual Database |
|---|---|---|---|---|
| DNA | | BLASTn | | DNA |
| PRT | | BLASTp | | PRT |
| DNA | PRT | BLASTx | | PRT |
| PRT | | tBLASTn | PRT | DNA |
| DNA | PRT | tBLASTx | PRT | DNA |

A polynucleotide comprising a fragment of the aforementioned nucleic acid sequence is also encompassed as a polynucleotide of the present invention. The fragment shall encode a polypeptide which still has desaturase activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The variant polynucleotides or fragments referred to above, preferably, encode polypeptides retaining desaturase activity to a significant extent, preferably, at least 10%, at least 20%, at least 30%, at least 40%, at least 50%, at least 60%, at least 70%, at least 80% or at least 90% of the desaturase activity exhibited by the polypeptide shown in any one of SEQ ID NO: 2. The activity may be tested as described in the accompanying Examples.

The polynucleotides of the present invention either essentially consist of the aforementioned nucleic acid sequence or comprise the aforementioned nucleic acid sequence. Thus, they may contain further nucleic acid sequences as well. Preferably, the polynucleotide of the present invention may comprise in addition to an open reading frame further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the polynucleotides of the present invention may encode fusion proteins wherein one partner of the fusion protein is a polypeptide being encoded by a nucleic acid sequence recited above. Such fusion proteins may comprise as additional part other enzymes of the fatty acid or PUFA biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

The polynucleotide of the present invention shall be provided, preferably, either as an isolated polynucleotide (i.e. purified or at least isolated from its natural context such as its natural gene locus) or in genetically modified or exogenously (i.e. artificially) manipulated form. An isolated polynucleotide can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The polynucleotide, preferably, is provided in the form of double or single stranded molecule. It will be understood that the present invention by referring to any of the aforementioned polynucleotides of the invention also refers to complementary or reverse complementary strands of the specific sequences or variants thereof referred to before. The polynucleotide encompasses DNA, including cDNA and genomic DNA, or RNA polynucleotides.

However, the present invention also pertains to polynucleotide variants which are derived from the polynucleotides of the present invention and are capable of intereferring with the transcription or translation of the polynucleotides of the present invention. Such variant polynucleotides include antisense nucleic acids, ribozymes, siRNA molecules, morpholino nucleic acids (phosphorodiamidate morpholino oligos), triple-helix forming oligonucleotides, inhibitory oligonucleotides, or micro RNA molecules all of which shall specifically recognize the polynucleotide of the invention due to the presence of complementary or substantially complementary sequences. These techniques are well known to the skilled artisan. Suitable variant polynucleotides of the aforementioned kind can be readily designed based on the structure of the polynucleotides of this invention.

Moreover, comprised are also chemically modified polynucleotides including naturally occurring modified polynucleotides such as glycosylated or methylated polynucleotides or artificial modified ones such as biotinylated polynucleotides.

In the studies underlying the present invention, advantageously, polynucleotides where identified encoding desaturase or elongases from *Limonomyces roseipellis, Sphaeoforma arctica, Latisaria fuciforma, Thielaviopsis basicola* or *Verticullium dahliae*. In particular, a Δ8-desaturase, Δ5-desaturase, Δ12-desaturases and Δ15-desaturases and a multifunctional elongase have been identified. Each of the desaturases are capable of introducing a double bond into fatty acids. For example, the expression of the Δ8-desaturase leads to introduction of a double bond at position eight into C20: 2n-6 fatty acid. The polynucleotides of the present invention are particularly suitable in combination for the recombinant manufacture of LCPUFAs and, in particular, ARA, EPA and/or DHA.

In a preferred embodiment of the polynucleotide of the present invention, said polynucleotide further comprises an expression control sequence operatively linked to the said nucleic acid sequence.

The term "expression control sequence" as used herein refers to a nucleic acid sequence which is capable of governing, i.e. initiating and controlling, transcription of a nucleic acid sequence of interest, in the present case the nucleic sequences recited above. Such a sequence usually comprises or consists of a promoter or a combination of a promoter and enhancer sequences. Expression of a polynucleotide comprises transcription of the nucleic acid molecule, preferably, into a translatable mRNA. Additional regulatory elements may include transcriptional as well as translational enhancers. The following promoters and expression control sequences may be, preferably, used in an expression vector according to the present invention. The cos, tac, trp, tet, trp-tet, lpp, lac, lpp-lac, lacIq, T7, T5, T3, gal, trc, ara, SP6, λ-PR or λ-PL promoters are, preferably, used in Gram-negative bacteria. For Gram-positive bacteria, promoters amy and SPO2 may be used. From yeast or fungal promoters ADC1, AOX1r, GAL1, MFα, AC, P-60, CYC1, GAPDH, TEF, rp28, ADH are, preferably, used. For animal cell or organism expression, the promoters CMV-, SV40-, RSV-promoter (Rous sarcoma virus), CMV-enhancer, SV40-enhancer are preferably used. From plants the promoters CaMV/35S [Franck 1980, Cell 21: 285-294], PRP1 (Ward 1993, Plant. Mol. Biol. 22), SSU, OCS, lib4, usp, STLS1, B33, nos or the ubiquitin or phaseolin promoter. Also preferred in this context are inducible promoters, such as the promoters described in EP 0 388 186 A1 (i.e. a benzylsulfonamide-inducible promoter), Gatz 1992, Plant J. 2:397-404 (i.e. a tetracyclin-inducible promoter), EP 0 335 528 A1 (i.e. a abscisic-acid-inducible promoter) or WO 93/21334 (i.e. a ethanol- or cyclohexenol-inducible promoter). Further suitable plant promoters are the promoter of cytosolic FBPase or the ST-LSI promoter from potato (Stockhaus 1989, EMBO J. 8, 2445), the phosphoribosyl-pyrophosphate amidotransferase promoter from *Glycine max* (Genbank accession No. U87999) or the node-specific promoter described in EP 0 249 676 A1. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially preferred promoters are seed-specific promoters which can be used for monocotyledonous or dicotyledonous plants and which are described in U.S. Pat. No. 5,608,152 (napin promoter from oilseed rape), WO 98/45461 (oleosin promoter from *Arobidopsis*, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for monocots: lpt-2 or lpt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890. In a particular embodiment, seed-specific promoters are utilized to enhance the production of the desired PUFA or LCPUFA.

The term "operatively linked" as used herein means that the expression control sequence and the nucleic acid of interest are linked so that the expression of the said nucleic acid of interest can be governed by the said expression control sequence, i.e. the expression control sequence shall be functionally linked to the said nucleic acid sequence to be expressed. Accordingly, the expression control sequence and, the nucleic acid sequence to be expressed may be physically linked to each other, e.g., by inserting the expression control sequence at the 5"end of the nucleic acid sequence to be expressed. Alternatively, the expression control sequence and the nucleic acid to be expressed may be merely in physical proximity so that the expression control sequence is capable of governing the expression of at least one nucleic acid sequence of interest. The expression control sequence and the nucleic acid to be expressed are, preferably, separated by not more than 500 bp, 300 bp, 100 bp, 80 bp, 60 bp, 40 bp, 20 bp, 10 bp or 5 bp.

In a further preferred embodiment of the polynucleotide of the present invention, said polynucleotide further comprises a terminator sequence operatively linked to the nucleic acid sequence.

The term "terminator" as used herein refers to a nucleic acid sequence which is capable of terminating transcription. These sequences will cause dissociation of the transcription machinery from the nucleic acid sequence to be transcribed. Preferably, the terminator shall be active in plants and, in particular, in plant seeds. Suitable terminators are known in the art and, preferably, include polyadenylation signals such as the SV40-poly-A site or the tk-poly-A site or one of the plant specific signals indicated in Loke et al. (Loke 2005, Plant Physiol 138, pp. 1457-1468), downstream of the nucleic acid sequence to be expressed. The present invention also relates to a vector comprising the polynucleotide of the present invention.

The term "vector", preferably, encompasses phage, plasmid, viral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homolgous or heterologous recombination as described in detail below. The vector encompassing the polynucleotide of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pBI101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus 1991, Annu. Rev. Plant Physiol. Plant Molec. Biol. 42, 205-225.

More preferably, the vector of the present invention is an expression vector. In such an expression vector, i.e. a vector which comprises the polynucleotide of the invention having the nucleic acid sequence operatively linked to an expression control sequence (also called "expression cassette") allowing expression in prokaryotic or eukaryotic cells or isolated fractions thereof. Suitable expression vectors are known in the art such as Okayama-Berg cDNA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith 1988, Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the recombinant target protein. Examples of suitable inducible nonfusion *E. coli* expression vectors are, inter alia, pTrc (Amann 1988, Gene 69:301-315) and pET 11d (Studier 1990, Methods in Enzymology 185, 60-89). The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the lacUV 5 promoter. The skilled worker is familiar with other vectors which are suitable in prokaryotic organisms; these vectors are, for example, in *E. coli*, pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667. Examples of vectors for expression in the yeast *S. cerevisiae* comprise pYep Sec1 (Baldari 1987, Embo J. 6:229-234), pMFa (Kurjan 1982, Cell 30:933-943), pJRY 88 (Schultz 1987, Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith 1983, Mol. Cell. Biol. 3:2156-2165) and the pVL series (Lucklow 1989, Virology 170:31-39).

The polynucleotides of the present invention can be expressed in single-cell plant cells (such as algae), see Falciatore 1999, Marine Biotechnology 1 (3):239-251 and the references cited therein, and plant cells from higher plants (for example Spermatophytes, such as arable crops) by using plant expression vectors. Examples of plant expression vectors comprise those which are described in detail in: Becker 1992, Plant Mol. Biol. 20:1195-1197; Bevan 1984, Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTiACH5, which is known as octopine synthase (Gielen 1984, EMBO J. 3, 835) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie 1987, Nucl. Acids Research 15:8693-8711). As described above, plant gene expression must be functionally linked to a suitable promoter which performs the expression of the gene in a timely, cell-specific or tissue-specific manner. Promoters which can be used are constitutive promoters (Benfey 1989, EMBO J. 8:2195-2202) such as those which are derived from plant viruses such as 35S CAMV (Franck 1980, Cell 21:285-294), 19S CaMV (see U.S. Pat. No. 5,352,605 and WO 84/02913) or plant promoters such as the promoter of the Rubisco small subunit, which is described in U.S. Pat. No. 4,962,028. Other preferred sequences for the use in functional linkage in plant gene expression cassettes are targeting sequences which are required for targeting the gene product into its relevant cell compartment (for a review, see Kermode 1996, Crit. Rev. Plant Sci. 15, 4: 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (for a review, see Gatz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetracyclin-inducible promoter (Gatz 1992, Plant J. 2, 397-404) and an ethanol-inducible promoter. Promoters which respond to biotic or abiotic stress conditions are also suitable promoters, for example the pathogen-induced PRP1-gene promoter (Ward 1993, Plant Mol. Biol. 22:361-366), the heat-inducible hsp80 promoter from tomato (U.S. Pat. No. 5,187,267), the cold-inducible alpha-amylase promoter from potato (WO 96/12814) or the wound-inducible pinII promoter (EP 0 375 091 A). The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from *Vicia faba* (Baeumlein 1991, Mol. Gen. Genet. 225 (3):459-67), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the legumin B4 promoter (LeB4; Baeumlein 1992, Plant Journal, 2 (2):233-9), and promoters which bring about the seed-specific expression in monocotyledonous plants such as maize, barley, wheat, rye, rice and the like. Suitable promoters to be taken into consideration are the lpt2 or lpt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the sorghum kasirin gene, the rye secalin gene). Likewise, especially suitable are promoters which bring about the plastid-specific expression since plastids are the compartment in which the precursors and some end products of lipid biosynthesis are synthesized. Suitable promoters such as the viral RNA-polymerase promoter, are described in WO 95/16783 and WO 97/06250, and the clpP promoter from *Arabidopsis*, described in WO 99/46394.

The abovementioned vectors are only a small overview of vectors to be used in accordance with the present invention. Further vectors are known to the skilled worker and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells see the chapters 16 and 17 of Sambrook, loc cit.

It follows from the above that, preferably, said vector is an expression vector. More preferably, the said polynucleotide of the present invention is under the control of a seed-specific promoter in the vector of the present invention. A preferred seed-specific promoter as meant herein is selected from the group consisting of Conlinin 1, Conlinin 2, napin, LuFad3, USP, LeB4, Arc, Fae, ACP, LuPXR, and SBP. For details, see, e.g., US 2003-0159174.

Moreover, the present invention relates to a host cell comprising the polynucleotide or the vector of the present invention.

Preferably, said host cell is a plant cell and, more preferably, a plant cell obtained from an oilseed crop. More preferably, said oilseed crop is selected from the group consisting of flax (*Linum* sp.), rapeseed (*Brassica* sp.), soybean (*Glycine* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, *camelina, crambe*, oil palm, coconuts, groundnuts, sesame seed, castor bean, *lesquerella*, tallow tree, sheanuts, tungnuts, kapok fruit, poppy seed, jojoba seeds and perilla.

Also preferably, said host cell is a microorganism. More preferably, said microorganism is a bacterium, a fungus or algae. More preferably, it is selected from the group consisting of *Candida, Cryptococcus, Lipomyces, Rhodosporidium, Yarrowia* and *Schizochytrium*.

Moreover, a host cell according to the present invention may also be an animal cell. Preferably, said animal host cell is a host cell of a fish or a cell line obtained therefrom. More preferably, the fish host cell is from herring, salmon, sardine, redfish, eel, carp, trout, halibut, mackerel, zander or tuna.

Generally, the controlling steps in the production of LC-PUFAs, i.e., the long chain unsaturated fatty acid biosynthetic pathway, are catalyzed by membrane-associated fatty acid desaturases and elongases. Plants and most other eukaryotic organisms have specialized desaturase and elongase systems for the introduction of double bonds and the extension of fatty acids beyond C18 atoms. The elongase reactions have several important features in common with the fatty acid synthase complex (FAS). However, the elongase complex is different from the FAS complex as the complex is localized in the cytosol and membrane bound, ACP is not involved and the elongase 3-keto-acyl-CoA-synthase catalyzes the condensation of malonyl-CoA with an acyl primer. The elongase complex consists of four components with different catalytic functions, the keto-acyl-synthase (condensation reaction of malonyl-CoA to acyl-CoA, creation of a 2 C atom longer keto-acyl-CoA fatty acid), the keto-acyl-reductase (reduction of the 3-keto group to a 3-hydroxy-group), the dehydratase (dehydration results in a 3-enoyl-acyl-CoA fatty acid) and the enolyl-CoA-reductase (reduction of the double bond at position 3, release from the complex). For the production of LCPUFAs including ARA, EPA and/or DHA the elongation reactions, beside the desaturation reactions, are essential. Higher plants do not have the necessary enzyme set to produce LCPUFAs (4 or more double bonds, 20 or more C atoms). Therefore the catalytic activities have to be conferred to the plants or plant cells. The polynucleotides of the present invention catalyze the desaturation and elongation activities necessary for the formation of ARA, EPA and/or DHA. By delivering the novel desaturases and elongases increased levels of PUFAs and LCPUFAs are produced.

However, it will be understood that dependent on the host cell, further, enzymatic activities may be conferred to the host cells, e.g., by recombinant technologies. Accordingly, the present invention, preferably, envisages a host cell which in addition to the polynucleotide of the present invention comprises polynucleotides encoding such desaturases and/or elongases as required depending on the selected host cell. Preferred desaturases and/or elongases which shall be present in the host cell are at least one enzyme selected from the group consisting of: Δ-4-desaturase, Δ-5-desaturase, Δ-5-elongase, Δ-6-desaturase, Δ12-desaturase, Δ15-desaturase, ω3-desaturase and Δ-6-elongase. Especially preferred are the bifunctional d12d15-Desaturases d12d15Des(Ac) from *Acanthamoeba castellanii* (WO2007042510), d12d15Des(Cp) from *Claviceps purpurea* (WO2008006202) and d12d15Des (Lg)1 from *Lottia gigantea* (WO2009016202), the d12-Desaturases d12Des(Co) from *Calendula officinalis* (WO200185968), d12Des(Lb) from *Laccaria bicolor* (WO2009016202), d12Des(Mb) from *Monosiga brevicollis* (WO2009016202), d12Des(Mg) from *Mycosphaerella graminicola* (WO2009016202), d12Des(Nh) from *Nectria haematococca* (WO2009016202), d12Des(Ol) from *Ostreococcus lucimarinus* (WO2008040787), d12Des(Pb) from *Phycomyces blakesleeanus* (WO2009016202), d12Des(Ps) from *Phytophthora sojae* (WO2006100241) and d12Des(Tp) from *Thalassiosira pseudonana* (WO2006069710), the d15-Desaturases d15Des(Hr) from *Helobdella robusta* (WO2009016202), d15Des(Mc) from *Microcoleus chthonoplastes* (WO2009016202), d15Des(Mf) from *Mycosphaerella fijiensis* (WO2009016202), d15Des(Mg) from *Mycosphaerella graminicola* (WO2009016202) and d15Des (Nh)$_2$ from *Nectria haematococca* (WO2009016202), the d4-Desaturases d4Des(Eg) from *Euglena gracilis* (WO2004090123), d4Des(Tc) from *Thraustochytrium* sp. (WO2002026946) and d4Des(Tp) from *Thalassiosira pseudonana* (WO2006069710), the d5-Desaturases d5Des(Ol)$_2$ from *Ostreococcus lucimarinus* (WO2008040787), d5Des (Pp) from *Physcomitrella patens* (WO2004057001), d5Des (Pt) from *Phaeodactylum tricornutum* (WO2002057465), d5Des(Tc) from *Thraustochytrium* sp. (WO2002026946), d5Des(Tp) from *Thalassiosira pseudonana* (WO2006069710) and the d6-Desaturases d6Des(Cp) from *Ceratodon purpureus* (WO2000075341), d6Des(Ol) from *Ostreococcus lucimarinus* (WO2008040787), d6Des(Ot) from *Ostreococcus tauri* (WO2006069710), d6Des(Pf) from *Primula farinosa* (WO2003072784), d6Des(Pir)_BO from *Pythium irregulare* (WO2002026946), d6Des(Pir) from *Pythium irregulare* (WO2002026946), d6Des(Plu) from *Primula luteola* (WO2003072784), d6Des(Pp) from *Physcomitrella patens* (WO200102591), d6Des(Pt) from *Phaeodactylum tricornutum* (WO2002057465), d6Des(Pv) from *Primula vialii* (WO2003072784) and d6Des(Tp) from *Thalassiosira pseudonana* (WO2006069710), the d8-Desaturases d8Des(Ac) from *Acanthamoeba castellanii* (EP1790731), d8Des(Eg) from *Euglena gracilis* (WO200034439) and d8Des(Pm) from *Perkinsus marinus* (WO2007093776), the o3-Desaturases o3Des(Pi) from *Phytophthora infestans* (WO2005083053), o3Des(Pir) from *Pythium irregulare* (WO2008022963), o3Des(Pir)$_2$ from *Pythium irregulare* (WO2008022963) and o3Des(Ps) from *Phytophthora sojae* (WO2006100241), the bifunctional d5d6-elongases d5d6Elo(Om)2 from *Oncorhynchus mykiss* (WO2005012316), d5d6Elo(Ta) from *Thraustochytrium aureum* (WO2005012316) and d5d6Elo(Tc) from *Thraustochytrium* sp. (WO2005012316), the d5-elongases d5Elo (At) from *Arabidopsis thaliana* (WO2005012316), d5Elo (At)$_2$ from *Arabidopsis thaliana* (WO2005012316), d5Elo (Ci) from *Ciona intestinalis* (WO2005012316), d5Elo(Ol) from *Ostreococcus lucimarinus* (WO2008040787), d5Elo (Ot) from *Ostreococcus tauri* (WO2005012316), d5Elo(Tp) from *Thalassiosira pseudonana* (WO2005012316) and d5Elo(Xl) from *Xenopus laevis* (WO2005012316), the d6-elongases d6Elo(Ol) from *Ostreococcus lucimarinus* (WO2008040787), d6Elo(Ot) from *Ostreococcus tauri* (WO2005012316), d6Elo(Pi) from *Phytophthora infestans* (WO2003064638), d6Elo(Pir) from *Pythium irregulare* (WO2009016208), d6Elo(Pp) from *Physcomitrella patens* (WO2001059128), d6Elo(Ps) from *Phytophthora sojae* (WO2006100241), d6Elo(Ps)$_2$ from *Phytophthora sojae* (WO2006100241), d6Elo(Ps)$_3$ from *Phytophthora sojae* (WO2006100241), d6Elo(Pt) from *Phaeodactylum tricornutum* (WO2005012316), d6Elo(Tc) from *Thraustochytrium* sp. (WO2005012316) and d6Elo(Tp) from *Thalassiosira pseudonana* (WO2005012316), the d9-elongases d9Elo(Ig) from *Isochrysis galbana* (WO2002077213), d9Elo(Pm) from

*Perkinsus marinus* (WO2007093776) and d9Elo(Ro) from *Rhizopus oryzae* (WO2009016208). Particularly, if the manufacture of ARA is envisaged in higher plants, the enzymes, i.e. additionally a d6-desaturase, d6-elongase, d5-elongase, d5-desaturase, d12-desaturase, and d6-elongase or enzymes having essentially the same activity may be combined in a host cell. If the manufacture of EPA is envisaged in higher plants, the enzymes recited in Table 5 below (i.e. additionally a d6-desaturase, d6-elongase, d5-desaturase, d12-desaturase, d6-elongase, omega 3-desaturase and d15-desaturase), or enzymes having essentially the same activity may be combined in a host cell. If the manufacture of DHA is envisaged in higher plants, the enzymes recited in Table 6, below (i.e. additionally a d6-desaturase, d6-elongase, d5-desaturase, d12-desaturase, d6-elongase, omega 3-desaturase, d15-desaturase, d5-elongase, and d4-desaturase), or enzymes having essentially the same activity may be combined in a host cell.

The present invention also relates to a cell, preferably a host cell as specified above or a cell of a non-human organism specified elsewhere herein, said cell comprising a polynucleotide which is obtained from the polynucleotide of the present invention by a point mutation, a truncation, an inversion, a deletion, an addition, a substitution and homologous recombination. How to carry out such modifications to a polynucleotide is well known to the skilled artisan and has been described elsewhere in this specification in detail.

The present invention furthermore pertains to a method for the manufacture of a polypeptide encoded by a polynucleotide of any the present invention comprising
a) cultivating the host cell of the invention under conditions which allow for the production of the said polypeptide; and
b) obtaining the polypeptide from the host cell of step a).

Suitable conditions which allow for expression of the polynucleotide of the invention comprised by the host cell depend on the host cell as well as the expression control sequence used for governing expression of the said polynucleotide. These conditions and how to select them are very well known to those skilled in the art. The expressed polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. It is to be understood that depending on the host cell which is used for the aforementioned method, the polypeptides produced thereby may become posttranslationally modified or processed otherwise.

The present invention encompasses a polypeptide encoded by the polynucleotide of the present invention or which is obtainable by the aforementioned method.

The term "polypeptide" as used herein encompasses essentially purified polypeptides or polypeptide preparations comprising other proteins in addition. Further, the term also relates to the fusion proteins or polypeptide fragments being at least partially encoded by the polynucleotide of the present invention referred to above. Moreover, it includes chemically modified polypeptides. Such modifications may be artificial modifications or naturally occurring modifications such as phosphorylation, glycosylation, myristylation and the like (Review in Mann 2003, Nat. Biotechnol. 21, 255-261, review with focus on plants in Huber 2004, Curr. Opin. Plant Biol. 7, 318-322). Currently, more than 300 posttranslational modifications are known (see full ABFRC Delta mass list at http://www.abrf.org/index.cfm/dm.home). The polypeptide of the present invention shall exhibit the desaturase activity referred to above.

Encompassed by the present invention is, furthermore, an antibody which specifically recognizes the polypeptides of the invention.

Antibodies against the polypeptides of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the antibody of the present invention is a monoclonal antibody, a polyclonal antibody, a single chain antibody, a chimerized antibody or a fragment of any of these antibodies, such as Fab, Fv or scFv fragments etc. Also comprised as antibodies by the present invention are bispecific antibodies, synthetic antibodies or chemically modified derivatives of any of the aforementioned antibodies. The antibody of the present invention shall specifically bind (i.e. does significantly not cross react with other polypeptides or peptides) to the polypeptide of the invention. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth. Enzymol. 73, 3, which comprise the fusion of mouse myeloma cells to spleen cells derived from immunized mammals. The antibodies can be used, for example, for the immunoprecipitation, immunolocalization or purification (e.g., by affinity chromatography) of the polypeptides of the invention as well as for the monitoring of the presence of said variant polypeptides, for example, in recombinant organisms, and for the identification of proteins or compounds interacting with the proteins according to the invention.

Moreover, the present invention contemplates a non-human transgenic organism comprising the polynucleotide or the vector of the present invention.

Preferably, the non-human transgenic organism is a plant, plant part, or plant seed. Preferred plants to be used for introducing the polynucleotide or the vector of the invention are plants which are capable of synthesizing fatty acids, such as all dicotyledonous or monocotyledonous plants, algae or mosses. It is to be understood that host cells derived from a plant may also be used for producing a plant according to the present invention. Preferred plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as Tagetes. Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae such as the genera *Amphora, Cymbella, Okedenia, Phaeodactylum, Reimeria*, for example the genus and species *Phaeodactylum tricornutum*, Ditrichaceae such as the genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpureus, Ceratodon purpureus, Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [manihot] or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa], *Glycine max Dolichos soja, Glycine gracilis, Glycine hispida, Phaseolus max, Soja hispida* or *Soja max* [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans* major, *Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia [macadamia]*, Prasinophyceae such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae such as the genus *Cofea*, for example the genera and species *Cofea* spp., *Coffea arabica, Coffea canephora* or *Coffea liberica* [coffee], Scrophulariaceae such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, *macadamia*, avocado, bay, pumpkin/squash, linseed, soybean, pistachios, borage, trees (oil palm, coconut, walnut) or crops such as maize, wheat, rye, oats, triticale, rice, barley, cotton, cassava, pepper, Tagetes, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon*. Preferred algae are *Isochrysis, Mantoniella, Ostreococcus* or *Crypthecodinium*, and algae/diatoms such as *Phaeodactylum* or *Thraustochytrium*. More preferably, said algae or mosses are selected from the group consisting of: *Emiliana, Shewanella, Physcomitrella, Thraustochytrium, Fusarium, Phytophthora, Ceratodon, Isochrysis, Aleurita, Muscarioides, Mortierella, Phaeodactylum, Cryphthecodinium*, specifically from the genera and species *Thallasiosira pseudonona, Euglena gracilis, Physcomitrella patens, Phytophtora infestans, Fusarium graminaeum, Cryptocodinium cohnii, Ceratodon purpureus, Isochrysis galbana, Aleurita farinosa, Thraustochytrium* sp., *Muscarioides viallii, Mortierella alpina, Phaeodactylum tricornutum* or *Caenorhabditis elegans* or especially advantageously *Phytophtora infestans, Thallasiosira pseudonona* and *Cryptocodinium cohnii*.

Transgenic plants may be obtained by transformation techniques as elsewhere in this specification. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

Also encompassed are transgenic non-human animals comprising the vector or polynucleotide of the present invention. Preferred non-human transgenic animals envisaged by the present invention are fish, such as herring, salmon, sardine, redfish, eel, carp, trout, halibut, mackerel, zander or tuna.

However, it will be understood that dependent on the non-human transgenic organism specified above, further, enzymatic activities may be conferred to the said organism, e.g., by recombinant technologies. Accordingly, the present invention, preferably, envisages a non-human transgenic organism specified above which in addition to the polynucleotide of the present invention comprises polynucleotides encoding such desaturases and/or elongases as required depending on the selected host cell. Preferred desaturases and/or elongases which shall be present in the organism are at least one enzyme selected from the group of desaturases and/or elongases or the combinations specifically recited elsewhere in this specification (see above and Tables 5 and 6).

Furthermore, the present invention encompasses a method for the manufacture of polyunsaturated fatty acids comprising:
a) cultivating the host cell of the invention under conditions which allow for the production of polyunsaturated fatty acids in said host cell; and
b) obtaining said polyunsaturated fatty acids from the said host cell.

The term "polyunsaturated fatty acids (PUFA)" as used herein refers to fatty acids comprising at least two, preferably, three, four, five or six, double bonds. Moreover, it is to be understood that such fatty acids comprise, preferably from 18 to 24 carbon atoms in the fatty acid chain. More preferably, the term relates to long chain PUFA (LCPUFA) having from 20 to 24 carbon atoms in the fatty acid chain. Preferred unsaturated fatty acids in the sense of the present invention are selected from the group consisting of DGLA 20:3 (8,11,14), ARA 20:4 (5,8,11,14), iARA 20:4 (8,11,14,17), EPA 20:5 (5,8,11,14,17), DPA 22:5 (4,7,10,13,16), DHA 22:6 (4,7,10,13,16,19), 20:4 (8,11,14,17), more preferably, arachidonic acid (ARA) 20:4 (5,8,11,14), eicosapentaenoic acid (EPA) 20:5 (5,8,11,14,17), and docosahexaenoic acid (DHA) 22:6 (4,7,10,13,16,19). Thus, it will be understood that most preferably, the methods provided by the present invention pertaining to the manufacture of ARA, EPA or DHA. Moreover, also encompassed are the intermediates of LCPUFA which occur during synthesis. Such intermediates are, preferably, formed from substrates by the desaturase activity of the polypeptides of the present invention. Preferably, substrates encompass LA 18:2 (9,12), ALA 18:3 (9,12,15), Eicosadienoic acid 20:2 (11,14), Eicosatrienoic acid 20:3 (11,14,17)), DGLA 20:3 (8,11,14), ARA 20:4 (5,8,11,14), eicosatetraenoic acid 20:4 (8,11,14,17), Eicosapentaenoic acid 20:5 (5,8,11,14,17), Docosahexapentanoic acid 22:5 (7,10,13,16,19).

The term "cultivating" as used herein refers maintaining and growing the host cells under culture conditions which allow the cells to produce the said polyunsaturated fatty acid, i.e. the PUFA and/or LC-PUFA referred to above. This implies that the polynucleotide of the present invention is expressed in the host cell so that at least the desaturase activity is present. Suitable culture conditions for cultivating the host cell are described in more detail below.

The term "obtaining" as used herein encompasses the provision of the cell culture including the host cells and the culture medium as well as the provision of purified or partially purified preparations thereof comprising the polyunsaturated fatty acids, preferably, ARA, EPA, DHA, in free or in -CoA bound form, as membrane phospholipids or as triacylglyceride estres. More preferably, the PUFA and LC-PUFA are to be obtained as triglyceride esters, e.g., in form of an oil. More details on purification techniques can be found elsewhere herein below.

The host cells to be used in the method of the invention are grown or cultured in the manner with which the skilled worker is familiar, depending on the host organism. Usually, host cells are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C. under oxygen or anaerobic atmosphere dependent on the type of organism. The pH of the liquid medium can either be kept constant, that is to say regulated during the culturing period, or not. The cultures can be grown batchwise, semibatchwise or continuously. Nutrients can be provided at the beginning of the fermentation or administered semicontinuously or continuously: The produced PUFA or LC-PUFA can be isolated from the host cells as described above by processes known to the skilled worker, e.g., by extraction, distillation, crystallization, if appropriate precipitation with salt, and/or chromatography. It might be required to disrupt the host cells prior to purification. To this end, the host cells can be disrupted beforehand. The culture medium to be used must suitably meet the requirements of the host cells in question. Descriptions of culture media for various microorganisms which can be used as host cells according to the present invention can be found in the textbook "Manual of Methods for General Bacteriology" of the American Society for Bacteriology (Washington D.C., USA, 1981). Culture media can also be obtained from various commercial suppliers. All media components are sterilized, either by heat or by filter sterilization. All media components may be present at the start of the cultivation or added continuously or batchwise, as desired. If the polynucleotide or vector of the invention which has been introduced in the host cell further comprises an expressible selection marker, such as an antibiotic resistance gene, it might be necessary to add a selection agent to the culture, such as a antibiotic in order to maintain the stability of the introduced polynucleotide. The culture is continued until formation of the desired product is at a maximum. This is normally achieved within 10 to 160 hours. The fermentation broths can be used directly or can be processed further. The biomass may, according to requirement, be removed completely or partially from the fermentation broth by separation methods such as, for example, centrifugation, filtration, decanting or a combination of these methods or be left completely in said broth. The fatty acid preparations obtained by the method of the invention, e.g., oils, comprising the desired PUFA or LC-PUFA as triglyceride esters are also suitable as starting material for the chemical synthesis of further products of interest. For example, they can be used in combination with one another or alone for the preparation of pharmaceutical or cosmetic compositions, foodstuffs, or animal feeds. Chemically pure triglycerides comprising the desired PUFA or LC-PUFA can also be manufactured by the methods described above. To this end, the fatty acid preparations are further purified by extraction, distillation, crystallization, chromatography or combinations of these methods. In order to release the fatty acid moieties from the triglycerides, hydrolysis may be also required. The said chemically pure triglycerides or free fatty acids are, in particular, suitable for applications in the food industry or for cosmetic and pharmacological compositions.

Moreover, the present invention relates to a method for the manufacture of poly-unsaturated fatty acids comprising:
a) cultivating the non-human transgenic organism of the invention under conditions which allow for the production of poly-unsaturated fatty acids in said host cell; and
b) obtaining said poly-unsaturated fatty acids from the said non-human transgenic organism.

Further, it follows from the above that a method for the manufacture of an oil, lipid or fatty acid composition is also envisaged by the present invention comprising the steps of any one of the aforementioned methods and the further step of formulating PUFA or LC-PUFA as oil, lipid or fatty acid composition. Preferably, said oil, lipid or fatty acid composition is to be used for feed, foodstuffs, cosmetics or pharmaceuticals. Accordingly, the formulation of the PUFA or LC-PUFA shall be carried out according to the GMP standards for the individual envisaged products. For example, an oil may be obtained from plant seeds by an oil mill. However, for product safety reasons, sterilization may be required under the applicable GMP standard. Similar standards will apply for lipid or fatty acid compositions to be applied in cosmetic or pharmaceutical compositions. All these measures for formulating oil, lipid or fatty acid compositions as products are comprised by the aforementioned manufacture.

The present invention also relates to an oil comprising a polyunsaturated fatty acid obtainable by the aforementioned methods.

The term "oil" refers to a fatty acid mixture comprising unsaturated and/or saturated fatty acids which are esterified to triglycerides. Preferably, the triglycerides in the oil of the invention comprise PUFA or LC-PUFA as referred to above. The amount of esterified PUFA and/or LC-PUFA is, preferably, approximately 30%, a content of 50% is more preferred, a content of 60%, 70%, 80% or more is even more preferred. The oil may further comprise free fatty acids, preferably, the PUFA and LC-PUFA referred to above. For the analysis, the fatty acid content can be, e.g., determined by GC analysis after converting the fatty acids into the methyl esters by transesterification. The content of the various fatty acids in the oil or fat can vary, in particular depending on the source. The oil, however, shall have a non-naturally occurring composition with respect to the PUFA and/or LC-PUFA composition and content. It will be understood that such a unique oil composition and the unique esterification pattern of PUFA and LC-PUFA in the triglycerides of the oil shall only be obtainable by applying the methods of the present invention specified above. Moreover, the oil of the invention may comprise other molecular species as well. Specifically, it may comprise minor impurities of the polynucleotide or vector of the invention. Such impurities, however, can be detected only by highly sensitive techniques such as PCR.

The contents of all references cited throughout this application are herewith incorporated by reference in general and with respect to their specific disclosure content referred to above.

FIGURES

FIG. 1 shows a schematical overview of the different enzymatic activities leading to the production of ARA, EPA and DHA.

FIG. 2 shows the functionality of Δ15-desaturase from *L. roseipellis* in a yeast feeding experiment in the presence of 18:1 (A) and 18:2 (B).

FIG. 3 shows the functionality of multi-elongase Δ6Elo (Sa) from *S. arctica* in a yeast feeding experiment in the presence of no added fatty acids (A), GLA added (B), ALA added (C), ARA added (D) and EPA added (E).

FIG. 4 shows an overview of the activities of the Δ6Elo (Sa).

FIG. 5 shows the functionality of Δ15-desaturase from *S. arctica* in a yeast feeding experiment in the presence of 18:1 (A) and 18:2 (B).

FIG. 6 shows the functionality of Δ12/Δ15-desaturase from *L. fuciformis* in a yeast feeding experiment in the presence of 18:1 (A) and 18:2 (B).

FIG. 7 shows the functionality of Δ12-desaturase from *L. fuciformis* in a yeast feeding experiment in the presence of 18:1 (A) and 18:2 (B).

FIG. 8 shows the functionality of Δ12-desaturase from *T. brevicollis* in a yeast feeding experiment in the presence of 18:1 (A) and 18:2 (B).

Figure 9:
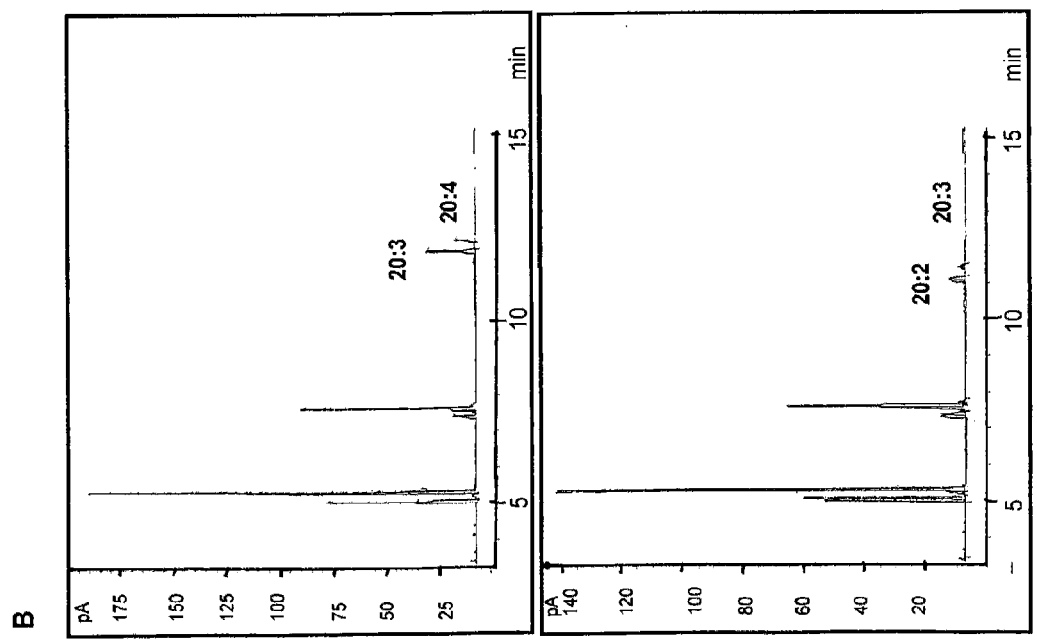

FIG. 9 shows the functionality of Δ8-desaturase from *S. arctica* in a yeast feeding experiment. The table (A) shows the used substrates and found products. The chromatograms (B) give the details for the found products.

FIG. 10 shows the functionality of Δ5-desaturase from *S. arctica* in a yeast feeding experiment. The table (A) shows the used substrates and found products. The chromatograms (B) give the details for the found products.

This invention is further illustrated by the following examples which should not be construed as limiting. The contents of all references, patents and published patent applications cited throughout this application, as well as the figures, are incorporated herein by reference.

EXAMPLES

Example 1

Cloning of Novel Desaturase and Elongase Sequences

RNA was extracted using the RNA-extraction Kit from Qiagen, a RACE-library was generated using the RACE-Kit from Clontech. From the RACE-library sequences for desaturase and elongases were amplified with PCR using following primer pairs (Table 2) and PCR conditions.

TABLE 2

Degenerated primers for amplification of desaturase genes.

| | | |
|---|---|---|
| Zan 348 (F) | SEQ ID NO: 53 | ACI GGI BTI TGG RTI BTI GSI CAY |
| Zan 349 (F) | SEQ ID NO: 54 | SAI GAR YTI KBI GGI TGG SMI |

TABLE 2-continued

Degenerated primers for amplification of desaturase genes.

| Zan 350 (R) | SEQ ID NO: 55 | IGT DAT IRV IAC IAR CCA RTG |
| Zan 351 (R) | SEQ ID NO: 56 | RTG IDW IYS IAY DAT ICC RTG |

Degenerated primers are in IUPAC standard nomenclature.
PCR reaction (50 µL):
5.00 µL Template cDNA
5.00 µL 10× Puffer (Advantage-Polymerase)+25 mM MgCl$_2$
5.00 µL 2 mM dNTP
1.25 µL je Primer (10 µmol/µL)
0.50 µL Advantage-Polymerase
Advantage polymerase mix from Clontech.
Reaction conditions of the PCR:
Annealing: 1 min 55° C.
Denaturation: 1 min 94° C.
Elongation: 2 min 72° C.
Cycles: 35

After 5'- and 3'-RACE full-length sequences were amplified with following primer pairs (Table 3).

TABLE 3

Primer pairs used in PCR to amplify full-length gene sequences

| Name | Primer pair (5' orientation) | SEQ ID NO. |
|---|---|---|
| D15Des(Lr)F | ATGGACACCACAGATGCACG | 21 |
| D15Des(Lr)R | TCAATCCGAATCCCTGTCCAC | 22 |
| D6Elo(Sa)F | ATGGCTCAAATACAAAATAT | 23 |
| D6Elo(Sa)R | TTACCTACTCTTCTTCTGCTC | 24 |
| D12Des(Lf)_1F | ATGGCCACCACGGATGCATC | 27 |
| D12 Des(Lf)_1R | TTAATCCGAATCCTTGTCAAC | 28 |
| D12Des(Lf)_2F | ATGGCCACTACTACCACCAC | 29 |
| D12Des(Lf)_2R | TTACTCCGAATCCCGATCAAC | 30 |
| D12Des(Tb)F | ATGACATCCACCGCTCTCCC | 31 |
| D12Des(Tb)R | TTAAGCTCGCCCTTTGCTTTC | 32 |
| D5Des(Sa)F | ATGTGTAAATCACAGAAACA | 33 |
| D5Des(Sa)R | TCATTCCTTTGTCTTATGGCCC | 34 |
| D8Des(Sa)F | TGGTACCCCGAGAGCGCTTG | 35 |
| D8Des(Sa)R | TTACGTGGTCATCTCCGGTGAAC | 36 |
| D12(Sa)F | ATGCCACCCAATGCGTTAAAAGAGC | 47 |
| D12(Sa)R | CTAATTTGTTTTTGTTTTCCTAGCTTCCATGC | 48 |
| D12(Vd)F | ATGGCTGCGACCACATCCTCGTTGCC | 51 |
| D12(Vd)R | CTACTGCTCATCCGTACGGCCCATGGCGGC | 52 |

The PCR reactions resulted in following polynucleotide sequences listed in Table 4.

TABLE 4

List of full-length coding sequences and deduced amino acid sequences

| SEQ ID NO: | Gene | Coding sequence (bp) | Amino acid sequence (length) | SEQ ID NO. |
|---|---|---|---|---|
| 1 | D15Des(Lr) | 1317 | 439 | 2 |
| 3 | D6Elo(Sa) | 867 | 289 | 4 |
| 5 | D15Des(Sa) | 1101 | 367 | 6 |
| 7 | D12Des(Lf)_1 | 1317 | 439 | 8 |
| 9 | D12Des(Lf)_2 | 1332 | 444 | 10 |
| 11 | D12Des(Tb) | 1434 | 478 | 12 |
| 13 | D5Des(Sa) | 1320 | 440 | 14 |
| 15 | D8Des(Sa) | 1428 | 476 | 16 |
| 45 | D12Des(Sa) | 1179 | 391 | 46 |
| 49 | D12Des(Vd) | 1446 | 481 | 50 |

Open reading frames as shown in Table 4 were cloned into the pYES2.1(Ura) vector from Invitrogen according to manufactures reaction conditions. Reactions were transformed into *E. coli* DH5α and plasmid DNA was isolated. The plasmids pYES-D15Des(Lr), pYES-D6Elo(Sa), pYES-D15Des(Sa), pYES-d12Des(Lf)_1, pYES-d12Des(Lf)_2, pYESd12Des(Tb), pYES-d5Des(Sa) and pYES-D8Des(Sa) were then used for yeast transformation.

Example 2

Yeast Transformation and Growth Conditions

*S. cerevisiae* strain INVSC from Invitrogen was transformed with the constructs pYES-D15Des(Lr), pYES-D6Elo(Sa), pYES-D15Des(Sa), pYES-d12Des(Lf)_1, pYES-d12Des(Lf)_2, pYESd12Des(Tb), pYES-d5Des(Sa) and pYES-D8Des(Sa) using the S.C. EasyComp Transformation Kit (Invitrogen, Carlsbad, Calif.) with selection on uracil-deficient medium.

Yeast were grown after transformation in complete medium containing all amino acids and nucleotides. Then yeast were plated on different medium containing either the complete medium (SD) or the complete medium lacking leucine (SD-Ura). Only yeast containing pYES-D15Des(Lr), pYES-D6Elo(Sa), pYES-D15Des(Sa), pYES-d12Des(Lf)_1, pYES-d12Des(Lf)_2, pYESd12Des(Tb), pYES-d5Des(Sa) and pYES-D8Des(Sa) vectors can grow on this medium.

Example 3

Functional Expression of Desaturases and Elongase in Yeast and Gas Chromatographic Analysis Yeast cells containing the respective pYES2.1 plasmids as prepared above were incubated 12 h in liquid DOB-U medium at 28° C., 200 rpm inkubiert and than additional 12 h in induction medium (DOB-U+2% (w/v) galactose+2% (w/v) raffinose). To the induction medium 250 µM of the respective fatty acids were added to check for enzyme activity and specificity.

Yeast cells were analyzed as following:

Yeast cells from induction medium were harvested by centrifugation (100×g, 5 min, 20° C.) and washed with 100 mM NaHCO$_3$, pH 8.0, to remove residual fatty acids. From the yeast pellet a total extract of fatty acid methylesters (FAME) was generated by adding 2 ml 1 N methanolic sulfuric acid and 2% (v/v) Dimethoxypropan for 1 h at 80° C. FAME were extracted two times with Petroletber (PE). Not derivated fatty acids were removed by washing with 2 ml 100 mM NaHCO$_3$, pH 8.0 and 2 ml Aqua dest. The PE-phases were dried with Na$_2$SO$_4$ and eluted in 100 μl PE. The samples were then separated with a DB-23-column (30 m, 0.25 mm, 0.25 μm, Agilent) in a Hewlett-Packard 6850-machine with FID using following conditions: oven temperature 50° C. to 250° C. with a rate of 5° C./min and finally 10 min at 250° C.

The identification of the fatty acids was done using the retention times of known fatty acid standards (Sigma). The method is described e.g. in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Example 4

Functional Characterization of D15Des(Lr)

As described above D15Des(Lr) was functionally characterized in yeast. The result of the analysis is shown in FIG. 2. Yeast transformed with pYES-D15Des(Lr) was tested under two conditions, A) feeding with 18:1 and B) feeding with 18:2. When feeding 18:1 no additional fatty acids beside the yeast endogenous ones were detected. The effect of feeding 18:1Δ9 is reflected in increased levels of 18:1. When feeding 18:2Δ9,12 one additional peak was observed. By using standards to determine the identity of the peak, it could be shown that the newly produced fatty acid is 18:3Δ9,12,15. Therefore the product of D15Des(Lr) has Δ15-desaturase activity. Based on the reads for 18:1, 18:2 and 18:3, a conversion rate of 68.4% could be calculated. The high conversion rate was unexpected. So far published enzymes with Δ15-desaturase activity show conversion rates in the rage of 50%.

Following formula is used to calculate conversion rates: [product]/[substrate+product]*100.

Example 5

Functional Characterization of D6Elo(Sa)

As described above D6Elo(Sa) was functionally characterized in yeast. The result of the analysis is shown in FIG. 3. Yeast transformed with pYES-D15Des(Lr) was tested under six conditions, A) no feeding and B) feeding with 18:3Δ6,9,12 and C) feeding with 18:4Δ6,9,12,15 and D) feeding with 18:3Δ9,12,15 and E) feeding with 20:4Δ5,8,11,14 and F) feeding with 20:5Δ5,8,11,14,17. When no feeding was done, an additional fatty acid beside the yeast endogenous was detected. In this experiment 20:1Δ9 was observed. This indicates that the product of the novel gene has elongase activity. In further experiments (B-F) the exact specificity of the product of D6Elo(Sa) was determined. Highest conversion rates were observed for Δ6-C18 fatty acids (γ18:3 and 18:4), followed by Δ9-C18 fatty acids and Δ5-C20 fatty acids. The specificity of the novel D6Elo(Sa) was unexpected as a combined activity of Δ9-elongase and Δ6/5-elongase has not been observed before. The described activities (Δ9-, Δ6/5-) have been associated with distinct enzymes either exhibiting Δ9- or Δ6/5-activity. FIG. 4 gives an overview of the activities of D6Elo(Sa). The bi-functionality of the elongase is beneficial for the synthesis of long-chain polyunsaturated fatty acids.

Example 6

Functional Characterization of D15Des(Sa)

As described above D15Des(Sa) was functionally characterized in yeast. The result of the analysis is shown in FIG. 5. Yeast transformed with pYES-D15Des(Sa) was tested under two conditions, A) feeding with 18:1 and B) feeding with 18:2. When feeding 18:1 no additional fatty acids beside the yeast endogenous ones were detected. The effect of feeding 18:1Δ9 is reflected in increased levels of 18:1. When feeding 18:2Δ9,12, one additional peak was observed. By using standards to determine the identity of the peak, it could be shown that the newly produced fatty acid is 18:3Δ9,12,15. Therefore the product of D15Des(Lr) has Δ15-desaturase activity. Based on the reads for 18:1, 18:2 and 18:3, a conversion rate of 55.5% could be calculated.

Example 7

Functional Characterization of D12Des(LF)_1, D12Des(Lf)_2 and D12Des(Tb)

As described above D12Des(Lf)_1, D12Des(Lf)_2 and D12Des(Tb) were functionally characterized in yeast. The result of the analysis is shown in FIGS. 6-8. Transformed yeast was tested under two conditions, A) feeding with 18:1 and B) feeding with 18:2. When feeding 18:1 no additional fatty acids beside the yeast endogenous ones were detected. The effect of feeding 18:1Δ9 is reflected in increased levels of 18:1. When feeding 18:2Δ9,12, one additional peak was observed. By using standards to determine the identity of the peak, it could be shown that the newly produced fatty acid is 18:3Δ9,12,15. Therefore the product of D15Des(Lr) has Δ15-desaturase activity. Based on the reads for 18:1, 18:2 and 18:3, a conversion rate of 55.5% could be calculated.

Example 8

Functional Characterization of D5Des(Sa) and D8Des(Sa)

As described above D5Des(Sa) and D8Des(Sa) were functionally characterized in yeast. The result of the analysis is shown in FIGS. 9 and 10. Transformed yeast was tested under a number of conditions as shown in the respective tables (A). The chromatograms (B) verify the findings. Based on the different substrates tested, the product of D5Des(Sa) has Δ5-desaturase activity. A conversion rate of 35% could be calculated. Based on the different substrates tested, the product of D8Des(Sa) has Δ8-desaturase activity. Conversion rates of 27% and 20% for the substrates 20:3Δ11,14,17 or 20:2Δ11,14 could be calculated, respectively.

Example 9

Expression of Novel Desaturases and Elongase in Plants

The novel desaturase and also elongases were cloned into a plant transformation vector as described in WO2003/093482, WO2005/083093 or WO2007/093776. Exemplary suitable combinations of genes are described in Table 5 and 6.

TABLE 5

Gene combinations for the production of EPA.

| Gene | Activity | SEQ ID NO: |
|---|---|---|
| D6Des(Ot) | Δ6-desaturase | 37 |
| D6Elo(Sa) | Δ5-elongase | 7 |
| D5Des(Sa) | Δ5-desaturase | 13 |
| D12Des(Lf)_1 | Δ12-desaturase | 7 |
| D6Elo(Tp) | Δ6-elongase | 39 |
| o3-Des(Pi) | omega 3-desaturase | 41 |
| D15Des(Lr) | Δ15-desaturase | 1 |
| D8Des(Sa) | Δ8-desaturase | 11 |

TABLE 6

Gene combinations for the production of DHA.

| Gene | Aktivität | SEQ ID NO: |
|---|---|---|
| D6Des(Ot) | Δ6-Desaturase | 37 |
| D6Elo(Sa) | Δ5-Elongase | 7 |
| D5Des(Sa) | Δ5-Desaturase | 13 |
| D12Des(Lf)_1 | Δ12-Desaturase | 7 |
| D6Elo(Tp) | Δ6-Elongase | 39 |
| o3-Des(Pi) | Omega 3-Desaturase | 41 |
| D15Des(Lr) | Δ15-Desaturase | 1 |
| D4Des(Tc) | Δ4-desaturase | 43 |
| D8Des(Sa) | Δ8-Desaturase | 11 |

As an additionally gene or substitutionally to the gene D12Des(Lf)_1 coding for a polypeptide having Δ12-Desaturase activity the gene D12Des(Lf)_2 coding for a polypeptide having Δ12-Desaturase activity could be combined with the genes of the Tables 5 or 6.

Additionally as an alternative gene or substitutionally to the genes D12Des(Lf)_1 and/or D12Des(Lf)_2 coding for polypeptides having Δ12-Desaturase activity the gene D12Des(Tb) coding for a polypeptide having Δ12-Desaturase activity also could be combined with the genes mentioned in Table 5 or Table 6, also.

Additionally or substitutionally to the gene D15Des(Lr) coding for a polypeptide having Δ15-desaturase activity another gene coding for a polypeptide having Δ15-desaturase activity also, i.e. D15Des(Sa) could be combined with the genes mentioned in the Tables 5 or 6.

Transgenic rapeseed lines were generated as described in Deblaere et al, 1984, Nucl. Acids. Res. 13, 4777-4788 and seeds of transgenic rapeseed plants are analyzed as described in Qiu et al. 2001, J. Biol. Chem. 276, 31561-31566.

Transgenic *Arabidopsis* plants were generated as described in Bechtholdt et al. 1993 C.R. Acad. Sci. Ser. III Sci. Vie., 316, 1194-1199.

Example 10

Functional Characterization of D12Des(Sa), D12Des(Vd)

As described above D12Des(Sa) and D12Des(Vd) were functionally characterized in yeast. The result of the analysis is shown in Table 7 and 8. Transformed yeast was tested under a number of conditions as shown in the respective tables. Based on these experiments, the product of D12Des(Sa) and d12Des(Vd) have Δ12-desaturase activity. For d12Des(Sa), an average conversion rate of 74% could be calculated for conversion of 18:1Δ9 to 18:2Δ9,12 when only endogenous 18:1Δ9 was available (table 7). When feeding 0.250 mM 18:1Δ9, the average conversion rate was found to be 69% for conversion of 18:1Δ9 to 18:2Δ9,12 (table 8). For d12Des (Vd), an average conversion rate of 55% could be calculated for conversion of 18:1Δ9 to 18:2Δ9,12 when feeding 0.250 mM 18:1Δ9 (table 9).

TABLE 7

Yeast was transformed with pYES-d12Des(Sa) and fatty acid profiles were recorded for three clones expressing d12Des(Sa).

| | 18:1Δ9 (area) | 18:2Δ9, 12 (area) | Conversion (%) | 16:1Δ9 (area) | 16:2Δ9, 12 (area) | Conversion (%) |
|---|---|---|---|---|---|---|
| pySA12-3-1 | 6.6 | 19.7 | 75 | 35.3 | 18.1 | 34 |
| pySA12-3-3 | 8.0 | 18.6 | 70 | 31.7 | 18.8 | 37 |
| pySA12-3-4 | 6.3 | 19.6 | 76 | 34.5 | 19.6 | 36 |
| average | | | 74 | | | 36 |

Endogenous oleic acid (18:1) was converted to linoleic acid (18:2) and endogenous palmitoleic acid (16:1) was converted to palmitolenic acid (16:2). Amount of fatty acid is given as peak area from the corresponding chromatograms (arbitrary unit).

TABLE 8

Yeast was transformed with pYES-d12Des(Sa) and feed with 0.250 mM oleic acid (18:1).

| | 18:1Δ9 (area) | 18:2Δ9, 12 (area) | Conversion (%) | 16:1Δ9 (area) | 16:2Δ9, 12 (area) | Conversion (%) |
|---|---|---|---|---|---|---|
| pySA12-3-1 | 11.6 | 24.3 | 68 | 30.5 | 10.8 | 26 |
| pySA12-3-3 | 12.2 | 24.0 | 66 | 30.9 | 10.7 | 26 |
| pySA12-3-4 | 10.1 | 2.0 | 73 | 28.6 | 11.9 | 29 |
| average | | | 69 | | | 27 |

Fatty acid profiles were recorded for three clones expressing d12Des(Sa). Fed oleic acid (18:1) was converted to linoleic acid (18:2) and endogenous palmitoleic acid (16:1) was converted to palmitolenic acid (16:2). Amount of fatty acid is given as peak area from the corresponding chromatograms (arbitrary unit).

TABLE 9

Yeast was transformed with pYES-d12Des(Vd)
and feed with 0.250 mM oleic acid (18:1).

| | 18:1Δ9 (area) | 18:2Δ9,12 (area) | Conversion (%) | 16:1Δ9 (area) | 16:2Δ9,12 (area) | Conversion (%) |
|---|---|---|---|---|---|---|
| pyVDni12-1 | 14.2 | 23.4 | 62 | 25.0 | 11.0 | 31 |
| pyVDni12-4 | 22.3 | 24.2 | 52 | 19.3 | 6.0 | 24 |
| pyVDni12-7 | 19.4 | 20.4 | 51 | 29.2 | 8.4 | 22 |
| average | | | 55 | | | 26 |

Fatty acid profiles were recorded for three clones expressing d12Des(Vd). Fed oleic acid (18:1) was converted to linoleic acid (18:2) and endogenous palmitoleic acid (16:1) was converted to palmitolenic acid (16:2). Amount of fatty acid is given as peak area from the corresponding chromatograms (arbitrary unit).

Example 11

Expression of d12Des(Vd) and d12Des(Sa) in Plants

The novel desaturase d12Des(Vd) and d12Des(Sa) were cloned into a plant transformation vector as described in WO2003/093482, WO2005/083093 or WO2007/093776. Exemplary suitable combinations of genes are described in Table 5 and 6.

TABLE 10

Gene combinations for the production of EPA.

| Gene | Activity | SEQ ID NO: |
|---|---|---|
| D6Des(Ot) | Δ6-desaturase | 37 |
| D6Elo(Sa) | Δ5-elongase | 7 |
| D5Des(Sa) | Δ5-desaturase | 13 |
| D12Des(Sa) | Δ12-desaturase | 45 |
| D6Elo(Tp) | Δ6-elongase | 39 |
| o3-Des(Pi) | omega 3-desaturase | 41 |
| D15Des(Lr) | Δ15-desaturase | 1 |
| D8Des(Sa) | Δ8-desaturase | 11 |

TABLE 11

Gene combinations for the production of DHA.

| Gene | Aktivity | SEQ ID NO: |
|---|---|---|
| D6Des(Ot) | Δ6-Desaturase | 37 |
| D6Elo(Sa) | Δ5-Elongase | 7 |
| D5Des(Sa) | Δ5-Desaturase | 13 |
| D12Des(Sa) | Δ12-Desaturase | 45 |
| D6Elo(Tp) | Δ6-Elongase | 39 |
| o3-Des(Pi) | Omega 3-Desaturase | 41 |
| D15Des(Lr) | Δ15-Desaturase | 1 |
| D4Des(Tc) | Δ4-desaturase | 43 |
| D8Des(Sa) | Δ8-Desaturase | 11 |

As an additionally gene or substitutionally to the gene D12Des(Sa) coding for a polypeptide having Δ12-Desaturase activity, the gene D12Des(Vd) (SEQ-ID No: 49) coding for a polypeptide having Δ12-Desaturase activity could be combined with the genes of the Tables 10 or 11.

Additionally as an alternative gene or substitutionally to the genes D12Des(Sa) or D12Des(Vd) coding for polypeptides having Δ12-Desaturase activity the gene D12Des(Tb) coding for a polypeptide having Δ12-Desaturase activity also could be combined with the genes mentioned in Table 10 or Table 11, also.

Additionally or substitutionally to the gene D15Des(Lr) coding for a polypeptide having Δ15-desaturase activity another gene coding for a polypeptide having Δ15-desaturase activity also, i.e. D15Des(Sa) could be combined with the genes mentioned in the Tables 10 or 11.

Transgenic rapeseed lines were generated as described in Deblaere et al, 1984, Nucl. Acids. Res. 13, 4777-4788 and seeds of transgenic rapeseed plants are analyzed as described in Qiu et al. 2001, J. Biol. Chem. 276, 31561-31566. Transgenic Arabidopsis plants were generated as described in Bechtholdt et al. 1993 C.R. Acad. Sci. Ser. III Sci. Vie., 316, 1194-1199.

REFERENCE LIST

Arondel, V., Lemieux, B., Hwang, I., Gibson, S., Goodman, H. M., and Somerville, C. R. (1992). Map-based cloning of a gene controlling omega-3 fatty acid desaturation in *Arabidopsis*. Science 258, 1353-1355.

Broadwater, J. A., Whittle, E., and Shanklin, J. (2002). Desaturation and hydroxylation. Residues 148 and 324 of *Arabidopsis* FAD2, in addition to substrate chain length, exert a major influence in partitioning of catalytic specificity. J. Biol. Chem. 277, 15613-15620.

Broun, P., Shanklin, J., Whittle, E., and Somerville, C. (1998b). Catalytic plasticity of fatty acid modification enzymes underlying chemical diversity of plant lipids. Science 282, 1315-1317.

Calvo, A. M., Gardner, H. W., and Keller, N. P. (2001). Genetic connection between fatty acid metabolism and sporulation in *Aspergillus nidulans*. J. Biol. Chem. 276, 25766-25774.

Knutzon, D. S., Thurmond, J. M., Huang, Y. S., Chaudhary, S., Bobik, E. G., Jr., Chan, G. M., Kirchner, S. J., and Mukerji, P. (1998). Identification of Delta5-dehydratase from *Mortierella alpina* by heterologous expression in Bakers' yeast and canola. J. Biol. Chem. 273, 29360-29366.

Mantle, P. G. and Nisbet, L. J. (1976). Differentiation of *Claviceps purpurea* in axenic culture. J. Gen. Microbiol. 93, 321-334.

Mey, G., Oeser, B., Lebrun, M. H., and Tudzynski, P. (2002). The biotrophic, non-appressorium-forming grass pathogen *Claviceps purpurea* needs a Fus3/Pmk1 homologous mitogen-activated protein kinase for colonization of rye ovarian tissue. Mol. Plant. Microbe Interact. 15, 303-312.

Okuley, J., Lightner, J., Feldmann, K., Yadav, N., Lark, E., and Browse, J. (1994). *Arabidopsis* FAD2 gene encodes the enzyme that is essential for polyunsaturated lipid synthesis. Plant Cell 6, 147-158.

Qi, B., Fraser, T., Mugford, S., Dobson, G., Sayanova, O., Butler, J., Napier, J. A., Stobart, A. K., and Lazarus, C. M. (2004). Production of very long chain polyunsaturated omega-3 and omega-6 fatty acids in plants. Nat. Biotechnol. 22, 739-745.

Qiu, X., Hong, H., and McKenzie, S L. (2001) Identification of a Delta 4 fatty acid desaturase from *Thraustochytrium* sp. involved in the biosynthesis of docosahexanoic acid by heterologous expression in *Saccharomyces cerevisiae* and *Brassica juncea*. J Biol Chem 276, 31561-6.

Shanklin, J. and Cahoon, E. B. (1998). DESATURATION AND RELATED MODIFICATIONS OF FATTY ACIDSI. Annu. Rev. Plant Physiol Plant Mol. Biol. 49, 611-641.

Tudzynski, P., Correia, T., and Keller, U. (2001). Biotechnology and genetics of ergot alkaloids. Appl. Microbiol. Biotechnol. 57, 593-605.

All references cited in this specification are herewith incorporated by reference with respect to their entire disclosure content and the disclosure content specifically mentioned in this specification.

The invention claimed is:

1. A polynucleotide comprising an expression control sequence operatively linked and heterologous to a nucleic acid sequence selected from the group consisting of:
   a) the nucleic acid sequence of SEQ ID NO: 1;
   b) a nucleic acid sequence encoding a polypeptide having the amino acid sequence of SEQ ID NO: 2;
   c) a nucleic acid sequence being at least 85% identical to the nucleic acid sequence of a), wherein said nucleic acid sequence encodes a polypeptide having 415-desaturase activity; and
   d) a nucleic acid sequence encoding a polypeptide having Δ15-desaturase activity and having an amino acid sequence which is at least 85% identical to the amino acid sequence of SEQ ID NO: 2.

2. The polynucleotide of claim 1, wherein said polynucleotide further comprises a terminator sequence operatively linked to the nucleic acid sequence.

3. A vector comprising the polynucleotide of claim 1, wherein said polynucleotide optionally further comprises a terminator sequence operatively linked to the nucleic acid sequence.

4. A host cell comprising the polynucleotide of claim 1 or a vector comprising said polynucleotide, wherein said polynucleotide optionally further comprises a terminator sequence operatively linked to the nucleic acid sequence.

5. A method for the manufacture of a polypeptide, comprising:
   a) cultivating the host cell of claim 4 under conditions which allow for the production of a polypeptide encoded by the polynucleotide; and
   b) obtaining said polypeptide from the host cell of step a).

6. A non-human transgenic organism comprising the polynucleotide of claim 1 or a vector comprising said polynucleotide.

7. The non-human transgenic organism of claim 6, wherein the organism is a plant, a plant part, a plant seed, a fish or a microorganism.

8. A method for the manufacture of polyunsaturated fatty acids, comprising:
   a) cultivating the host cell of claim 4 under conditions which allow for the production of polyunsaturated fatty acids in said host cell; and
   b) obtaining said polyunsaturated fatty acids from said host cell.

9. A method for the manufacture of polyunsaturated fatty acids, comprising:
   a) cultivating the non-human transgenic organism of claim 6 under conditions which allow for the production of polyunsaturated fatty acids in said non-human transgenic organism; and
   b) obtaining said polyunsaturated fatty acids from said non-human transgenic organism.

10. The method of claim 9, wherein the polyunsaturated fatty acid is arachidonic acid (ARA), eicosapentaenoic acid (EPA), and/or docosahexaenoic acid (DHA).

11. A method for the manufacture of an oil-, lipid- or fatty acid-composition, comprising obtaining polyunsaturated fatty acids according to the method of claim 9, and formulating the polyunsaturated fatty acids in an oil-, lipid- or fatty acid-composition.

12. The method of claim 11, wherein the oil-, lipid- or fatty acid-composition is to be used for feed, foodstuffs, cosmetics or pharmaceuticals.

13. A method for the manufacture of an oil-, lipid- or fatty acid-composition, comprising obtaining polyunsaturated fatty acids according to the method of claim 10, and formulating the polyunsaturated fatty acids in an oil-, lipid- or fatty acid-composition.

14. The polynucleotide of claim 1, wherein said nucleic acid sequence encodes a polypeptide having Δ15-desaturase activity and having a conversion rate more than 50%.

15. The polynucleotide of claim 1, wherein the nucleic acid sequence encodes a polypeptide having Δ15-desaturase activity and having at least 90% sequence identity to the amino acid sequence of SEQ ID NO: 2.

16. The polynucleotide of claim 1, wherein the nucleic acid sequence encodes a polypeptide having Δ15-desaturase activity and having at least 95% sequence identity to the amino acid sequence of SEQ ID NO: 2.

17. A method for the manufacture of polyunsaturated fatty acids, comprising:
   a) cultivating a plant comprising the polynucleotide of claim 1 or a vector comprising said polynucleotide under conditions which allow for the production of polyunsaturated fatty acids in said plant or seeds thereof; and
   b) obtaining said polyunsaturated fatty acids from said plant or seeds thereof.

18. The method of claim 17, comprising obtaining an oil-, lipid- or fatty acid-composition from said plant or seeds thereof, and obtaining the polyunsaturated fatty acids from said oil-, lipid- or fatty acid-composition.

19. A method for the manufacture of an oil-, lipid- or fatty acid-composition, comprising:
   a) cultivating a plant comprising the polynucleotide of claim 1 or a vector comprising said polynucleotide under conditions which allow for the production of polyunsaturated fatty acids in said plant or seeds thereof; and
   b) obtaining an oil-, lipid- or fatty acid-composition from said plant or seeds thereof.

20. The method of claim 17, wherein the polyunsaturated fatty acids are obtained from the seeds of said plant.

* * * * *